(12) United States Patent
Yokota et al.

(10) Patent No.: US 7,747,491 B2
(45) Date of Patent: Jun. 29, 2010

(54) ANONYMOUS INFORMATION SYSTEM, INFORMATION REGISTERING DEVICE AND INFORMATION STORING DEVICE

(75) Inventors: Kaoru Yokota, Ashiya (JP); Motoji Ohmori, Hirakata (JP); Akinobu Ito, Tokyo (JP)

(73) Assignee: Panasonic Corporation, Osaka (JP)

( * ) Notice: Subject to any disclaimer, the term of this patent is extended or adjusted under 35 U.S.C. 154(b) by 677 days.

(21) Appl. No.: 11/281,577

(22) Filed: Nov. 18, 2005

(65) Prior Publication Data

US 2006/0136253 A1    Jun. 22, 2006

(30) Foreign Application Priority Data

Nov. 19, 2004  (JP)  ............................. 2004-335642

(51) Int. Cl.
   *G06Q 40/00*    (2006.01)
(52) U.S. Cl. ............................................. 705/35; 705/3
(58) Field of Classification Search .................... 705/35
    See application file for complete search history.

(56) References Cited

U.S. PATENT DOCUMENTS 6,005,943 A * 12/1999 Cohen et al. .................. 380/30

7,181,017 B1 * 2/2007 Nagel et al. .................. 380/282

FOREIGN PATENT DOCUMENTS

JP    2002-312361    10/2002

* cited by examiner

*Primary Examiner*—James P Trammell
*Assistant Examiner*—John A Anderson
(74) *Attorney, Agent, or Firm*—Wenderoth, Lind & Ponack, L.L.P.

(57) ABSTRACT

An anonymous information system is capable of maintaining anonymity of data while improving safety with regard to loss of anonymity caused by hacking of secret information, or the like. Conversion processing for converting from individual specifying information to anonymous individual information is split between an information providing device and an anonymity server device. Further, the manner in which the conversion processing is split is varied for each information providing device. A parameter generating device calculates $X_{inv}$ to satisfy $X_i \times X_{inv} = 1 \bmod q$, a first characteristic parameter $KA_i = G^{\wedge} X_{inv} \bmod q$, and a second characteristic parameter $KB_i = X_i$. The information providing device generates a semi-anonymous individual identifier $C = (KA_i)^{\wedge} D \bmod P$. The anonymity server device calculates an anonymous individual identifier $E = (C)^{\wedge} KB_i \bmod P$.

17 Claims, 24 Drawing Sheets

FIG. 4

INDIVIDUAL SPECIFYING INFORMATION S —261

| NAME | —262 |
| DATE OF BIRTH | —263 |
| HOME ADDRESS | —264 |
| HOME TELEPHONE NUMBER | —265 |

INDIVIDUAL RELATED INFORMATION —271

| EXAMINATION DATE | —272 |
| DIAGNOSED MEDICAL PROBLEMS | —273 |
| PRESCRIPTION INFORMATON | —274 |
| TEST RESULTS | —275 |
| OBSERVATIONS | —276 |

FIG. 7

SERVER-USE CHARACTERISTIC PARAMETER LIST

| SERVER-USE PARAMETER INFORMATION ||
|---|---|
| CLIENT IDENTIFIER | SECOND CHARACTERISTIC PARAMETER |
| 1 | $KB_1$ |
| 2 | $KB_2$ |
| 3 | $KB_3$ |
| ⋮ | ⋮ |

FIG. 8

INFORMATION STORING UNIT (317)

ANONYMOUS INFORMATION (351)

| | | |
|---|---|---|
| ANONYMOUS INFORMATION IDENTIFIER (352) | 000001 | |
| ANONYMOUS INDIVIDUAL IDENTIFIER (353) | 0123456··· | |
| INDIVIDUAL RELATED INFORMATION (354) | EXAMINATION DATE | 1/1/2000 |
| | DIAGNOSED MEDICAL PROBLEM | APPENDICITIS |
| | PRESCRIPTION INFORMATION | DRUG XYZ |
| | TEST RESULTS | WHITE BLOOD CELL COUNT... |
| | OBSERVATIONS | SURGERY |

ANONYMOUS INFORMATION (361)

| | | |
|---|---|---|
| ANONYMOUS INFORMATION IDENTIFIER (362) | 000002 | |
| ANONYMOUS INDIVIDUAL IDENTIFIER (363) | 0325426··· | |
| INDIVIDUAL RELATED INFORMATION (364) | EXAMINATION DATE | 26/3/2000 |
| | DIAGNOSED MEDICAL PROBLEM | APPENDICITIS |
| | PRESCRIPTION INFORMATION | DRUG ABC |
| | TEST RESULTS | BLOOD PRESSURE... |
| | OBSERVATIONS | SURGERY |

ANONYMOUS INFORMATION (371)

| | | |
|---|---|---|
| ANONYMOUS INFORMATION IDENTIFIER (372) | 000003 | |
| ANONYMOUS INDIVIDUAL IDENTIFIER (373) | 0123456··· | |
| INDIVIDUAL RELATED INFORMATION (374) | EXAMINATION DATE | 21/3/2001 |
| | DIAGNOSED MEDICAL PROBLEM | PNEUMONIA |
| | PRESCRIPTION INFORMATION | DRUG P01 |
| | TEST RESULTS | BLOOD PRESSURE... |
| | OBSERVATIONS | HOSPITALIZATION REQUIRED |

ANONYMOUS INFORMATION SYSTEM, INFORMATION REGISTERING DEVICE AND INFORMATION STORING DEVICE

This application is based on an application No. 2004-335642 filed in Japan, the content of which is hereby incorporated by reference.

BACKGROUND OF THE INVENTION (1) Field of the Invention

The present invention relates to a technology for converting information of a highly private nature into an anonymous form such that it is impossible to specify to whom the information relates, and for storing and supplying the converted information.

(2) Description of the Related Art

Medical information such as the results from diagnoses and medical examinations which have taken place in hospitals is commonly recorded together with personal information capable of specifying the patient to whom the results belong, such as a name, a date of birth, and an address, and the like. Further, grade data from examinations and the like in schools or other institutions and personal assessment data in industry are commonly stored together with students' and employees' personal information respectively. Moreover, in the case of data resulting from various types of survey, respondents' survey responses are commonly stored together with personal information.

Since this information reveals information such as who has which medical history, who obtained which grade or personal assessment, and who gave which survey response, it bears strongly upon privacy, and from the point of view of privacy protection, strict confidentiality management is required.

On the other hand, in the case of medical information, for instance, in order that statistical information, such as the number of patients afflicted with particular disease in a given year, or the like, may be acquired, and that the medical histories of particular patients may be traced and put to use in establishing new medical treatments and in preventative medicine, it is desirable to enter the medical information into a database and thereby make it available to a large number of researchers. Similarly, in the case that the information is grades and results, it is desirable that it can be used for finding statistical information such as grade distributions and the like, and thereby be of use in providing students with academic guidance, and the like.

Thus, it is desirable that information of the type described above is disclosed in the kind database that enables statistical enquiries, tracing, and the like, while protecting the privacy of the patients, the students, or the like.

Here, protecting the privacy of the patients or students is used to mean disclosing the results of medical examinations or diagnoses, or the grades, but making it impossible to specify the patients or students to whom the data belong.

In one general method conceivable as a method to fulfill the type of demands described above, data is stored in the public database only after the personal information section specifying the individual patients, individual students, or the like has been removed. In the case of medical information, for instance, each hospital removes the section containing personal information from the examination data (medical records) of patients who have been examined, and stores the remaining information in the public database. The information in the public database is disclosed to researchers, but since data specifying the origins of the patients is not included, patient privacy is protected.

However, there is a problem with this method in that if the same patient is examined at different hospitals for each of a series of medical problems, it is impossible to tell from the public database that the various clinical information belongs to the same patient since it is stored in the database with the patient's personal information removed.

One method disclosed as a method to solve this problem is capable of distinguishing clinical information belonging to the same patient while protecting patient privacy (see Japanese Laid-open Application No. 2002-312361, for instance). According to this method, the patient information is converted into an anonymous patient ID and stored in a data base, and a code table showing correspondences between the patient information and anonymous patient IDs is stored and managed. Using this method, it is possible to distinguish whether clinical information belongs to the same patient by making reference to the anonymous patient ID attached to the clinical information.

However, with this prior art, a code table showing the correspondences between the patient information and the anonymous patient IDs must be stored at the apparatus recording onto the public database. Consequently, the prior art has the problem that, if in a worst case scenario the code table were stolen from the apparatus in which it had been stored, the original patient information would be exposed by way of the anonymous patient IDs, and the anonymity of the clinical information on the data base would be completely lost.

SUMMARY OF THE INVENTION

In order to solve the stated problems it is an object of the present invention to provide an anonymous information system, an information providing device, an information storing device, a method, and a program, which are capable of maintaining the anonymity of the data in the database and, at the same time, of improving resistance to loss of anonymity in secret information due to hacking or the like. In an information providing system, the anonymous information system, the information providing device, the information storing device, the method, and the program, the systems and devices put into searchable database form individual specifying information capable of specifying an individual's name, address, date of birth, and the like, and individual related information, such as medical information, various types of personal background information, private survey response results, or the like, and provide these as information.

In order to solve the stated problems, the present invention is an anonymous information system that performs anonymity conversion processing on original individual specifying information that specifies an individual, to generate anonymous individual specifying information, the anonymous information system including: a conversion splitting device operable to split the anonymity conversion processing into two portions to generate first conversion processing that is one of the portions and second conversion processing that is the other one of the portions; a first converting device operable to perform the first conversion processing on the original individual specifying information to generate semi-anonymous individual specifying information; and a second converting device operable to perform the second conversion processing on the generated semi-anonymous individual specifying information to generate the anonymous individual specifying information.

According to this construction, the anonymity conversion processing is split to generate the first conversion processing and the second conversion processing, the first converting device using the first conversion processing and the second converting device using the second conversion processing, and consequently, this construction has the advantage that, even if one of the first and second conversion processing is exposed, the anonymity of the anonymous individual specifying information will not be lost.

Here, the anonymity conversion processing may generate, from the original individual specifying information and based on a base parameter, the anonymous individual specifying information from which the individual cannot be specified, the conversion splitting device may include: a first parameter generating unit operable to randomly generate a first parameter; a second parameter generating unit operable to generate a second parameter that is complementary to the first parameter with respect to the base parameter; and a first transmission unit operable to transmit the first parameter to the first converting device, and transmit the second parameter to the second converting device, the first converting device may include: a first receiving unit operable to receive the first parameter, an acquiring unit operable to acquire the original individual specifying information; a first converting unit operable to perform, as the first conversion processing, a repetitive calculation using the received first parameter and the acquired original individual specifying information, to generate the semi-anonymous individual specifying information; a second transmission unit operable to transmit the generated semi-anonymous individual specifying information to the second converting unit, and the second converting device may include: a storing unit having a region for storing the anonymous individual specifying information; a second receiving unit operable to receive the second parameter and the semi-anonymous individual specifying information; and a second converting unit operable to perform, as the second conversion processing, a repetitive calculation using the received second parameter and the received semi-anonymous individual specifying information to generate the anonymous individual specifying information, and to write the generated anonymous individual specifying information into the storing unit.

According to this construction, the anonymous conversion processing involves generating, from the original individual specifying information and based on the base parameter, the anonymous individual specifying information that is incapable of specifying the individual; generating a first parameter and a second parameter that is complementary to the first parameter with respect the basic parameter; performing, as the first conversion processing, a repetitive calculation using the received first parameter and the acquired original individual specifying information to generate the semi-anonymous individual specifying information; and performing, as the second conversion processing, a repetitive calculation using the received second parameter and the received semi-anonymous individual specifying information to generate the anonymous individual specifying information. Thus, through these two conversions, anonymous individual specifying information identical to the anonymous individual specifying information obtained by performing the anonymous conversion processing is obtained.

Here, in addition to being an information providing device that provides the original individual specifying information, the first converting device may further provide individual related information relating to the individual, and in addition to being an information storing device that stores the anonymous individual specifying information, the second converting device may store the anonymous individual specifying information in correspondence with the individual related information.

According to this construction, the second converting device that is the information storing device for storing the anonymous individual specifying information stores the anonymous individual specifying information in correspondence with the individual related information, and individual related information that belongs to the same individual can therefore be distinguished.

Here, the anonymous information system may further include: an information searching device operable to acquire, from the second converting device that is the information storing device, the anonymous individual specifying information and the individual related information which are desired by an operator.

According to this construction, it is possible to search for desired information.

Here, the conversion splitting device may further split the anonymity conversion processing into two portions to generate third conversion processing that is one of the portions and different from the first conversion processing, and fourth conversion processing that is the other one of the portions and different from the second conversion processing, the anonymous information system may further include: a third converting device operable to perform the third conversion processing on the original individual specifying information to generate other semi-anonymous individual specifying information, and the second converting device may further perform the fourth conversion processing on the generated other semi-anonymous individual specifying information to generate the anonymous individual specifying information.

According to this construction, the anonymous conversion processing is split to generate the first conversion processing and the second conversion processing, and the anonymous conversion processing is split to generate third conversion processing and fourth conversion processing. Consequently, the anonymous individual specifying information generated from the original individual specifying information using the first and second conversion processing will be identical to the anonymous individual specifying information generated from the original individual specifying information using the third and fourth conversion processing.

Here, the conversion splitting device may further split other anonymity conversion processing that is different from the anonymity conversion processing into two portions to generate third conversion processing that is one of the portions and different from the first conversion processing and fourth conversion processing that is the other of the portions and different from the second conversion processing, instead of the first conversion processing, the first conversion device may perform the third conversion processing on the original individual specifying information to generate other semi-anonymous individual specifying information, and instead of the second conversion processing, the second conversion device may perform the fourth conversion processing on the generated other semi-anonymous individual specifying information to generate other anonymous individual specifying information.

According to this construction, it is possible, when either the first conversion processing or the second conversion processing has been exposed, to update each with different conversion processing.

Here, the conversion splitting device may further split other anonymity conversion processing that is different to the anonymity conversion processing into two portions to generate third conversion processing that is one of the portions and different from the first conversion processing and fourth conversion processing that is the other one of the portions and different from the second conversion processing, instead of performing the first conversion processing, the first conversion device may perform the anonymity conversion processing on the original individual specifying information to generate the anonymous individual specifying information, and perform the third conversion processing on the generated anonymous individual specifying information to generate other semi-anonymous individual specifying information, instead of performing the second conversion processing, and the second conversion device may perform the fourth conversion processing on the generated other semi-anonymous individual specifying information to generate other anonymous individual specifying information.

According to this construction, it is possible, when both the first conversion processing and the second conversion processing have been exposed, to update each with different conversion processing.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 4 shows an example data structure for individual specifying information S261 and individual related information R271;

FIG. 7 shows an example data structure for the server-use characteristic parameter list 331;

FIG. 8 shows an example data structure for the anonymous information 351, 361, 371, . . . stored in the information storing unit 317;

DESCRIPTION OF THE PREFERRED EMBODIMENTS

1. First Embodiment

An anonymous information system 1 is described as one embodiment of the present invention.

1.1 Construction of the Anonymous Information System 1

Figure 1:
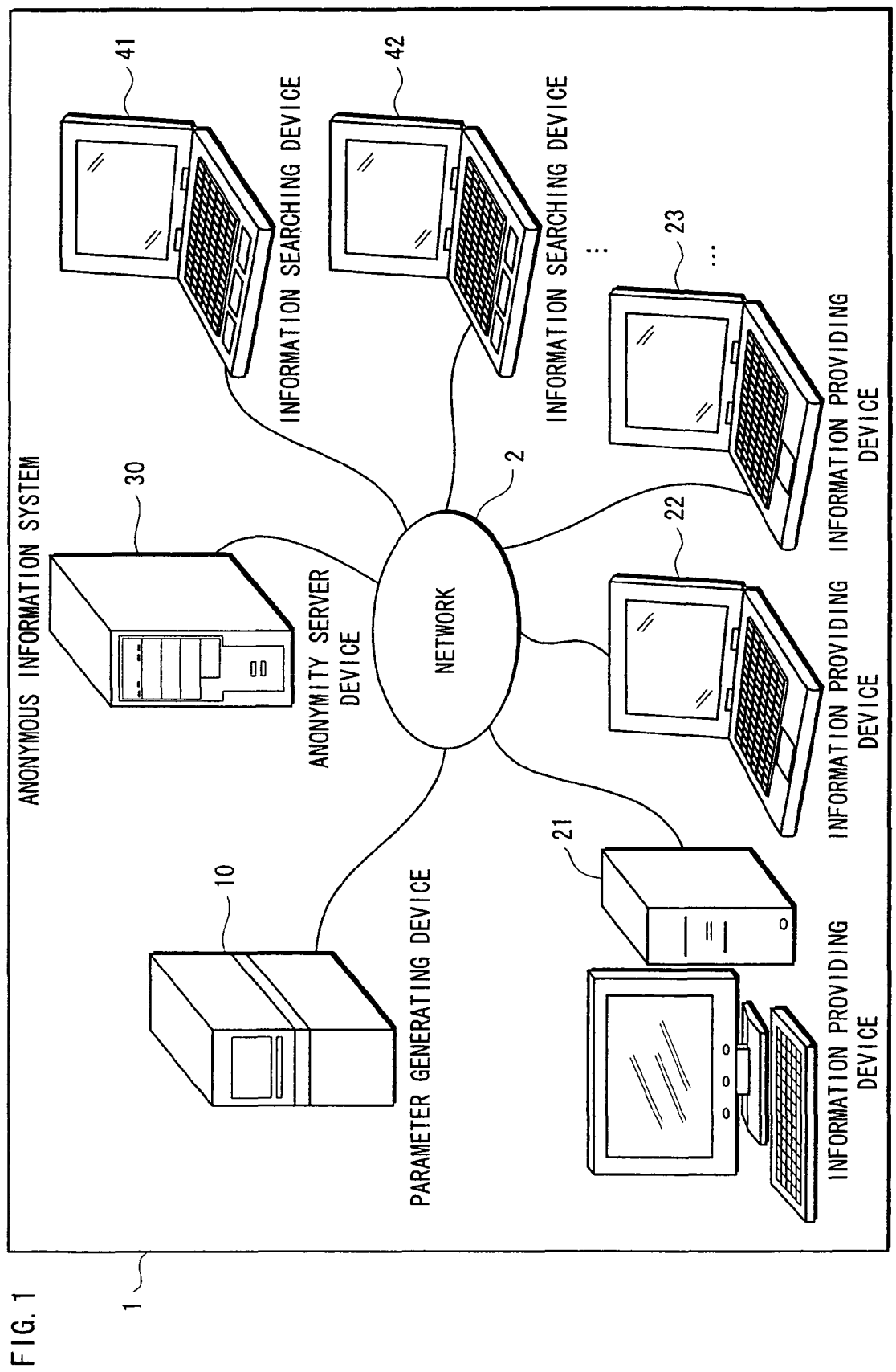
FIG. 1 shows the construction of an anonymous information system 1.

The anonymous information system 1 is, as shown in FIG. 1, constructed from a parameter generating device 10, information providing devices 21, 22, 23 . . . , an anonymity server device 30, and information searching devices 41, 42 . . . . The parameter generating device 10, the information providing devices 21, 22, 23 . . . , the anonymity server device 30, and the information searching devices 41, 42 . . . are interconnected via a network 2.

At system set-up, the parameter generating device 10 generates parameters used in semi-anonymity processing and anonymity processing which are described later, and transmits the generated parameters via the network 2 to the information providing devices 21, 22, 23 . . . and to the anonymity server device 30.

The information providing devices 21, 22, 23 . . . each receive input including individual specifying information that is to be made anonymous and individual related information that may be disclosed, and, according to a later described method, performs the semi-anonymity processing on the received individual specifying information to generate a semi-anonymous individual identifier, associates the semi-anonymous individual identifier and the individual related information in a one-to-one correspondence, and transmits the associated semi-anonymous individual identifier and individual related information to the anonymity server device 30.

The anonymity server device 30 receives the semi-anonymous individual identifier and the individual related information from each of the information providing devices 21, 22, 23, . . . , performs anonymity processing on the received semi-anonymous individual identifier to generate an anonymous individual identifier using a later-described method, and stores the anonymous individual identifier and the individual related information in a database.

The information searching devices 41, 42, . . . each transmit externally inputted search request information to the anonymity server device 30, and thereby perform search requests. The anonymity server 30 searches its internally stored database based on the search request information transmitted from the information searching devices 41, 42, . . . extracts the necessary individual related information, and transmits the extracted individual related information to the information searching devices 41, 42, . . . .

The anonymous information system 1 is, for example, applied in a medical information providing system which is run collaboratively by a plurality of related medical institutions, such as hospitals, and research and statistics institutes concerned with medical treatments. In such a case, the information providing devices 21, 22, 23 . . . would each be provided in a different hospital, and the information searching devices 41, 42 . . . each provided in a different research or statistics institute.

Here, an example of the individual specifying information that is to be made anonymous is information, such as a patient's name, date of birth, address, and telephone number, that specifies a patient examined in a hospital and that is capable of specifying individuals. On the other hand, examples of the individual related information include a date of the examination in a hospital, medical problems diagnosed by the doctor, prescription information relating to drugs used by the patient, results of tests taken by the patient, observations made by the doctor, and the like. Different examples of individual related information include exam results of individual students, income received and tax paid by individual employees, content of survey responses, and the like.

If it is supposed that a single patient undergoes examinations at a plurality of hospitals and for a different medical problem in each case, the content of the generated individual specifying information will be identical, but the individual related information will vary depending on the hospital.

In this case, an information providing device 21 installed in one of the hospitals receives as input first individual specifying information and first individual related information both of which relate to a certain patient, and in the manner described above, generates a first semi-anonymous individual identifier from the first piece of individual specifying information, and transmits the generated first semi-anonymous individual identifier and the first piece of individual related information to the anonymity server device 30.

In the manner described above, the anonymity server device 30 generates a first anonymous individual identifier from the first semi-anonymous individual identifier, associates the generated first anonymous individual identifier and the first individual related information and stores them in the database.

Further, the information providing device 22 installed in one of the other hospitals receives as input a second piece of individual specifying information identical in content to the first piece of individual specifying information, and a second piece of individual related information, both of which relate to the patient. In the manner described above, the information providing device 22 generates a second semi-anonymous identifier, and transmits the generated second semi-anonymous identifier and the second individual related information to the anonymity server 30.

In the manner described above, the anonymity server 30 generates a second anonymous individual identifier from the received second semi-anonymous identifier, associates the second anonymous identifier and the first individual related information and stores them in the database.

Here, the respective content of the first individual specifying information and the second individual specifying information is identical, the respective content of the first semi-anonymous individual identifier and the second semi-anonymous individual identifier differ, and the respective content of the first anonymous individual identifier and the second anonymous individual identifier is identical.

The information searching device 41 installed at the statistics institute transmits search request information including certain search conditions to the anonymity server device 30.

Since the respective content of the first and second anonymous individual identifiers is identical, on receiving the search request information, the anonymity server device 30 regards the first individual related information and the second individual related information associated with the first and second anonymous individual identifiers respectively as being information relating to the same patient. The anonymity server device 30 then associates the first and second individual related information, and transmits the associated first and second individual related information to the information searching device 41.

The information searching device 41 receives the associated first and second individual related information as information for a single patient, and performs statistical processing using the received first and second individual related information.

1.2 Parameter Generating Device 10

Figure 2:
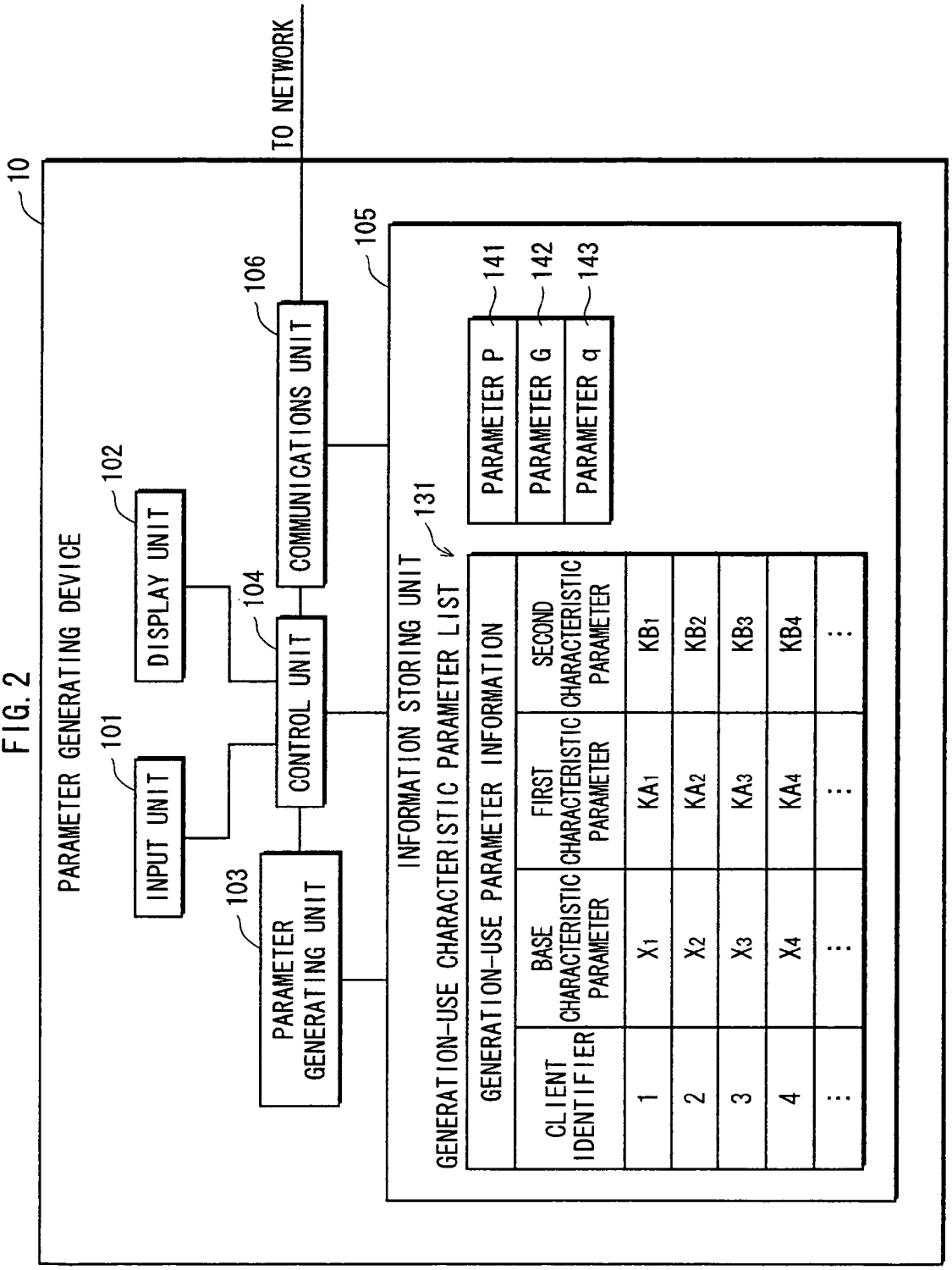
FIG. 2 is a block diagram showing the construction of a parameter generating device 10.

The parameter generating device 10 is, as shown in FIG. 2, constructed from an input unit 101, a display unit 102, a parameter generating unit 103, a control unit 104, an information storing unit 105, and a communications unit 106.

Specifically, the parameter generating device 10 is a computer system constructed from a microprocessor, ROM, RAM, a hard disk unit, a display unit, a keyboard, and the like. A computer program is stored in the RAM or the hard disk unit. The parameter generating device 10 achieves a portion of its functions by means of the microprocessor operating according to the computer program.

The parameter generating device 10 is possessed by a system setting organization.

(1) Information Storing Unit 105

As shown in FIG. 2, the information storing unit 105 includes regions for storing a parameter P 141, a parameter G 142, a parameter q 143, and a generation-use characteristic parameter list 131.

(Parameter P 141)

The parameter P 141 is a large prime number, such as a prime number that is 1024 bits in length. The following is one example of the parameter P 141:

"FFFFFFFF FFFFFFFF C90FDAA2 2168C234 C4C6628B 80DC1CD1 29024E08 8A67CC74 020BBEA6 3B139B22 514A0879 8E3404DD EF9519B3 CD3A431B 302B0A6D F25F1437 4FE1356D 6D51C245 E485B576 625E7EC6 F44C42E9 A637ED6B 0BFF5CB6 F406B7ED EE386BFB 5A899FA5 AE9F2411 7C4B1FE6 49286651 ECE65381 FFFFFFFF FFFFFFFF".

Note that this number is expressed in hexadecimal notation.

The parameter P 141 is a common parameter throughout the anonymous information system 1, and is transmitted to the information providing devices 21, 22, 23 . . . , and to the anonymity server device 30.

(Parameter G 142)

The parameter G 142 is an element in a Galois field GF(P) of order q, where the order q is large, and is selected such that the order q is a prime number and P−1 is divisible by q. An example of the parameter G 142, is an integer two bits in length, such as "2" (expressed using hexadecimal location).

Note that the values for the parameter P and the parameter G may be any values that make it very difficult, when an element β in GF(P) is given, to find an α that satisfies β=G^α mod P (this is known as a discrete logarithm problem).

In this specification, the symbol "^" indicates an exponential operation. For example, "a^b" indicates $a^b$.

The parameter G 142 is the base parameter in the conversion processing in which the semi-anonymity processing and the anonymity processing are performed consecutively.

(Parameter q 143)

Parameter q 143 is the order of parameter G 142. For example, the parameter G 142 is an integer 1024 bits in length, and the parameter q 134 may for instance be "P−1".

(Generation-Use Characteristic Parameter List 131)

As shown in FIG. 2, a generation-use characteristic parameter list 131 includes regions for storing a plurality of pieces of generation-use parameter information, each which is composed of a client identifier, a base characteristic parameter, a first characteristic parameter, and a second characteristic parameter.

Each of the pieces of plurality of generation-use parameter information corresponds to one of the information provision devices 21, 22, 23, . . . .

The client identifier is identifying information for uniquely identifying the corresponding information providing device. The client identifier has a fixed length, such as 32 bits, for instance. The client identifier may take any value provided that there is no overlap within the anonymous information system 1.

The base characteristic parameter is generated as a random number, and is used to generate the first characteristic parameter and the second characteristic parameter. The first characteristic parameter is used in the corresponding information providing device, and the second characteristic parameter is used in the anonymity server device 30. Note that the base characteristic parameter, the first characteristic parameter, and the second characteristic parameter are described later.

(2) Input Unit 101

The input unit 101 receives input including the parameter P, the parameter G, and the parameter q from an operator of the parameter generating device 10, and outputs the received parameter P, parameter G, and parameter q to the control unit 104.

Further, the input unit 101 receives, from the operator of the parameter generating device 10, a device designation indicating one of the information providing devices and a generation instruction to generate the characteristic parameters corresponding to the designated information providing device. The input unit 101 then outputs the received device designation and the generation instruction to the control unit 104.

(3) Control Unit 104

The control unit 104 receives, from the input unit 101, the parameter P, the parameter G, and the parameter q, and writes the received parameter P, parameter G, and parameter q into the storage unit 105 as the parameter P 141, the parameter G 142 and the parameter q 142 respectively.

Further, the control unit 104 receives the device designation and the generation instruction from the input unit 101. On receiving the device designation and the generation instruction, the control unit 104 outputs, to the parameter generating unit 103, a parameter generation instruction instructing that the characteristic parameters for the information providing device of the device designation is to be generated.

Next, the control unit 104 receives, from the parameter generating unit 103, a client identifier i, a first characteristic parameter $KA_i$, and a second characteristic parameter $KB_i$. On receiving the client identifier i, the first characteristic parameter $KA_i$, and the second characteristic parameter $KB_i$, the control unit 104 outputs the received the client identifier i, the first characteristic parameter $KA_i$, the second characteristic parameter $KB_i$, and the device designation to the communications unit 106. Further the control unit 104 outputs, to the communications unit 106, (a) a first transmission instruction indicating that the parameter P, the client identifier i, and the first characteristic parameter $KA_i$ are to be transmitted to the information providing device of the device designation, and (b) a second transmission instruction indicating that the client identifier i and the second characteristic parameter $KB_i$ are to be transmitted to the anonymity server 30.

(4) Parameter Generating Unit 103

The parameter generating unit 103 receives the parameter generating instruction from the control unit 104.

On receiving the parameter generating instruction, the parameter generating unit 103 generates a client identifier i that uniquely identifies the designated information providing device, and reads parameter P 141, parameter G 142 and parameter q 143 from the storage unit 105.

Next, the parameter generating unit 103 generates a random number that is greater than "1" but less than q. In other words it generates a random number that satisfies 2≦random number≦q−1. Next the parameter generating unit 103 judges whether or not the generated random number exists as a base characteristic parameter in the generation-use characteristic parameter list 131 of the information storing unit 105. If the generated random number does exist, the parameter generating unit 103 once again generates a random number. If the generated random number does not exist the parameter generating unit 103 sets the generated random number to be a base characteristic parameter $X_i$, and calculates $X_{inv}$ to satisfy:

$$X_i \times X_{inv} = 1 \bmod q \quad \text{(Expression 1).}$$

Next, the parameter generating unit 103 calculates a first characteristic parameter $KA_i$ according to:

$$KA_i = G^{\char`\^} X_{inv} \bmod q \quad \text{(Expression 2).}$$

Next, the parameter generating unit 103 calculates a second characteristic parameter $KB_i$ according to:

$$KB_i = X_i \quad \text{(Expression 3)}$$

Next, the parameter generating unit 103 writes the generation-use parameter information, which is composed of the generated client identifier i, base characteristic parameter $X_i$, first characteristic parameter $KA_i$, and second characteristic parameter $KB_i$, into the generation-use characteristic parameter list 131.

On completing the writing of the generation-use parameter information, the parameter generating unit 103 outputs, to the control unit 104, the generated client identifier i, first characteristic parameter $KA_i$, and second characteristic parameter $KB_i$.

Note that the generation of the above first and second characteristic parameters is performed separately for each information providing device. Thus, the first and second characteristic parameters take different values for each information providing device. The client identifiers identifying the information providing devices and the second characteristic parameters are stored as a list in the characteristic parameter list storing unit 312 in the anonymity server device 30.

Note that since $$KA_i \wedge KB_i \bmod q = (G \wedge X_{inv}) \wedge X_i \bmod q$$
$$= G \bmod q$$

the first characteristic parameter and the second characteristic parameter have a complementary relationship with respect to parameter G, the base parameter.

(5) Communications Unit 106

The communications unit 106 receives, from the control unit 104, the client identifier i, the first characteristic parameter $KA_i$, the second characteristic parameter $KB_i$, and the device designation, and further receives the first transmission instruction and the second transmission instruction.

On receiving the first transmission instruction and the second transmission instruction, the communications unit 106 reads the parameter P 141 from the information storing unit 105, and transmits the read parameter P, and the received client identifier i and first characteristic parameter $KA_i$ via the network 2 to the information providing device indicated by the device designation. Next, the communications unit 106 transmits the read parameter P and the received client identifier i and second characteristic parameter $KB_i$ via the network 2 to the anonymity server 30.

(6) Display Unit 102

The display unit 102 displays various information according to instructions from the control unit 104.

1.3 Construction of Information Providing Devices 21, 22, 23 . . . .

The information providing devices 21, 22, 23 . . . have identical constructions. Here, the construction of the information providing device 21 is described and descriptions of the other information providing devices 22, 23 . . . are omitted.

Figure 3:
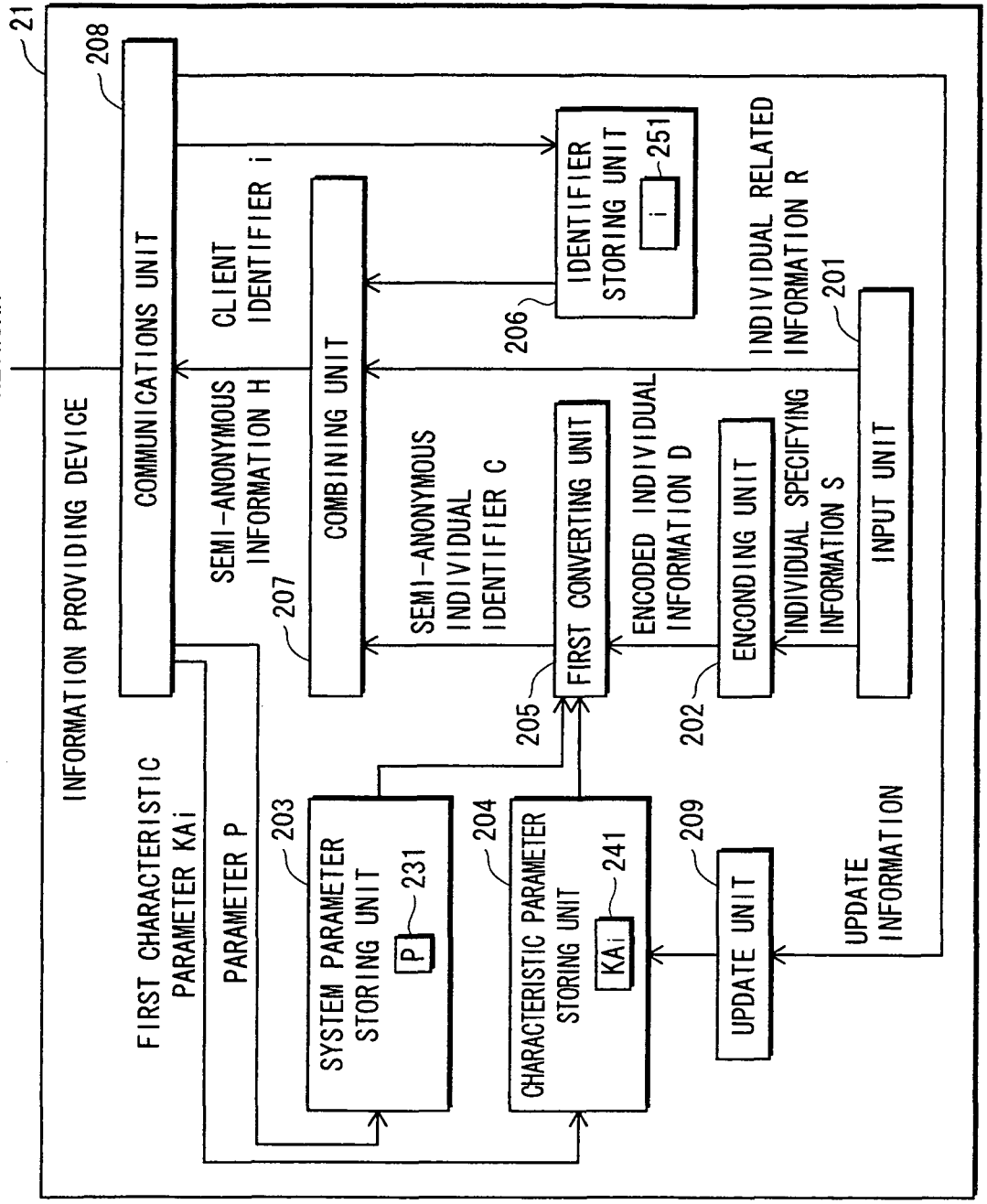
FIG. 3 is a block diagram showing the construction of an information providing device 21.

The information providing device 21 is, as shown in FIG. 3, constructed from an input unit 201, an encoder unit 202, a system parameter storing unit 203, a characteristic parameter storing unit 204, a first converting unit 205, an identifier storing unit 206, a combining unit 207, a communications unit 208, and an update unit 209.

Specifically, the information providing device 21, like the parameter generating device 10, is a computer system constructed from a microprocessor, ROM, RAM, a hard disk unit, and the like. A computer program is stored in the RAM. The information providing device 21 achieves a portion of its functions by means of the microprocessor operating according to the computer program.

(1) System Parameter Storing Unit 203, Characteristic Parameter Storing Unit 204, and Identifier Storing Unit 206

The system parameter storing unit 203 includes a region for storing a parameter P231. Here, parameter P231 is, as described above, a common parameter throughout the anonymous information system 1.

Further, the characteristic storing unit 204 includes a region for storing the first characteristic parameter $KA_i$ 241. Here, the first characteristic parameter $KA_i$ 241 has been generated, as described above, in such a way that it uniquely corresponds the information providing device 21.

Moreover, the identifier storing unit 206 includes a region for storing the client identifier i 206. Here, the client identifier is, as described above, identifying information for uniquely identifying the information providing device 21.

(2) Communications Unit 208

The communications unit 208 receives the parameter P, the first characteristic parameter $KA_i$, and the client identifier i via the network 2 from the parameter generating device 10. On receiving the parameter P, the first characteristic parameter $KA_i$, and the client identifier i, the communications unit 208 writes the received parameter P into the system parameter storing unit 203 as the parameter P 231, writes the received first characteristic parameter $KA_i$ into the characteristic parameter storing unit 204 as the first characteristic parameter $KA_i$ 241, and writes the received client identifier i into the identifier storing unit 206 as the client identifier i 251.

Further, the communications unit 208 receives semi-anonymous information H (described later) from the combining unit 208, and transmits the received semi-anonymous information H via the network 2 to the anonymity server device 30.

(3) Input Unit 201

The input unit 201 receives input including individual specifying information S and individual related information R from the operator of the information providing device 21. Here, the individual specifying information S is of a fixed length. Next, the input unit 201 outputs the received individual specifying information S to the encoder unit 202, and outputs the received individual related information to R to the combining unit 207.

An example of the individual specifying information S and the individual related information R is shown in FIG. 4.

Individual specifying information S 261 shown in FIG. 4 is composed of a name 262, a date of birth 263, a home address 264, and a home telephone number 265 of a patient examined at some hospital.

The name 262 is expressed using Japanese that includes kanji, is 10 characters long, and is expressed using a 2-byte system. This is to say that each character is expressed using 2 bytes (1 byte=8 bits). Consequently, the name 262 is 20 bytes in length (160 bits in length).

The date of birth 263 is composed of a year, a month, and a day, the year being expressed using a 4-figure number (the year "2000" for instance), the month using a 2-figure number (October being "10" for instance), and the day using a 2-figure number ("15" for instance). The date of birth 283 is expressed using an 8-figure number (15/10/2000, for instance). The date of birth is expressed in BCD (Binary Coded Decimal) in which each figure is 4-bits long, and consequently, the date of birth 263 has a total length of 32 bits.

The address 264 is expressed in Japanese, is 20 characters long, and is expressed using the 2-byte system. Consequently, the home address 264 is 40 bytes in length (320 bits in length).

The home telephone number 265 is composed of a 10-figure number, and is expressed using BCD. Since each figure is 4 bits long, the home telephone number has as total length of 40 bits.

According to the above, the individual specifying information S 261 is 552 bits in length (fixed length).

Further, the individual related information R 271 shown in FIG. 4 is composed of an examination date 272, diagnosed medical problems 273, prescription information 274, test results 275, and observations 276 for the examined patient. Like the data of birth 263, the examination date 272 is of a fixed length of 32 bits. The diagnosed medical problem 273, the prescription information 274, the test results 275, and the observations 276 are each of variable length.

(4) Encoder Unit 202

The encoder unit 202 includes a region for storing encoded individual information D that is 1024 bits in length. The encoded individual information D is treated as an integer 1024 bits in length.

The encoder unit 202 receives the individual specifying information S from the input unit 201. On receiving the individual specifying information S, the encoder unit 202 stores the received individual specifying information S in the 552 lower-order bit positions of the encoded individual information D, and stores NULL values in the remaining 472 higher-order bit positions.

As described above, the individual specifying information S is composed of a plurality of differing items each differing in its method of expression, including the name, the date of birth, the home address, and the home telephone number. However, these differing methods of expression, differing items and different lengths are ignored, and the various items are combined and treated as a single integer, which is expressed as a binary number.

Next, the encoding unit 202 outputs the encoded individual information D holding the individual specifying information S to the first converting unit 205.

Note that though in the above description all the individual specifying information S is used to generate the encoded individual information D, the present invention is not limited to this method.

For example, the name and date of birth alone, the name, date of birth, and telephone number alone, or some other combination may be used as the individual specifying information. Moreover, a postal code indicating a residential area may be used instead of the home address. Further, furigana for the patient's name may be used in addition to the name, date of birth, home address and home telephone number. "Furigana" is a means of showing a reading, in hiragana or katakana, for name that is written in kanji. "Hiragana" and "katakana" are alphabets used together with kanji in Japanese. Further, an individual identity number for uniquely identifying an individual may be added as part of the individual specifying information. An example of such an identify number is a social insurance number, such as any one of the identity numbers for specifying individuals used in health insurance, in disaster insurance, in employment insurance, in pension systems of various types, and in the like.

Further, when the bit length of the encoded individual information D is shorter than the bit length of the individual specifying information S, a one way function, such as a hash function, SHA-1 (Secure Hash Algorithm) for instance, may be performed on the individual specifying information S to generate a hash value of the same bit length as the encoded individual information D, and the generated hash value used as the encoded individual information D.

(5) First Converting Unit 205

The first converting unit 205 receives the encoded individual information D from the encoding unit 202. On receiving the encoded individual information D, the first converting unit 205 reads the parameter P 231 from the system parameter storing unit 203 and reads the first characteristic parameter $KA_i$ 241 from the characteristic parameter storing unit 204. Using the received encoded individual information D, the read parameter P 231 and the read first characteristic parameter $KA_i$ 241, the first converting unit 205 then performs semi-anonymity processing according to the following expression to generate the semi-anonymous individual identifier C.

$$C=(KA_i)^D \bmod P \qquad \text{(Expression 4)}$$

Expression 4 indicates a repetitive multiplication.

Here, the semi-anonymous individual identifier C is 1024 bits in length (fixed length).

Next, the first converting unit 205 outputs the generated semi-anonymous individual identifier C to the combining unit 207.

(6) Combining Unit 207

The combining unit 207 receives the individual related information R from the input unit 201, and receives the semi-anonymous individual identifier C from the first converting unit 205. On receiving the individual related information R and the semi-anonymous individual identifier C, the combining unit 207 reads the client identifier i 251 from the identifier storing unit 206, and as shown in FIG. 5, combines the read client identifier i, the received semi-anonymous individual identifier C, and the received individual related information R in the stated order to generate the semi-anonymous information H.

$$H=i\|C\|R \qquad \text{(Expression 5)}$$

where $A\|B$ indicates that "A" and "B" are combined in the stated order.

Figure 5:
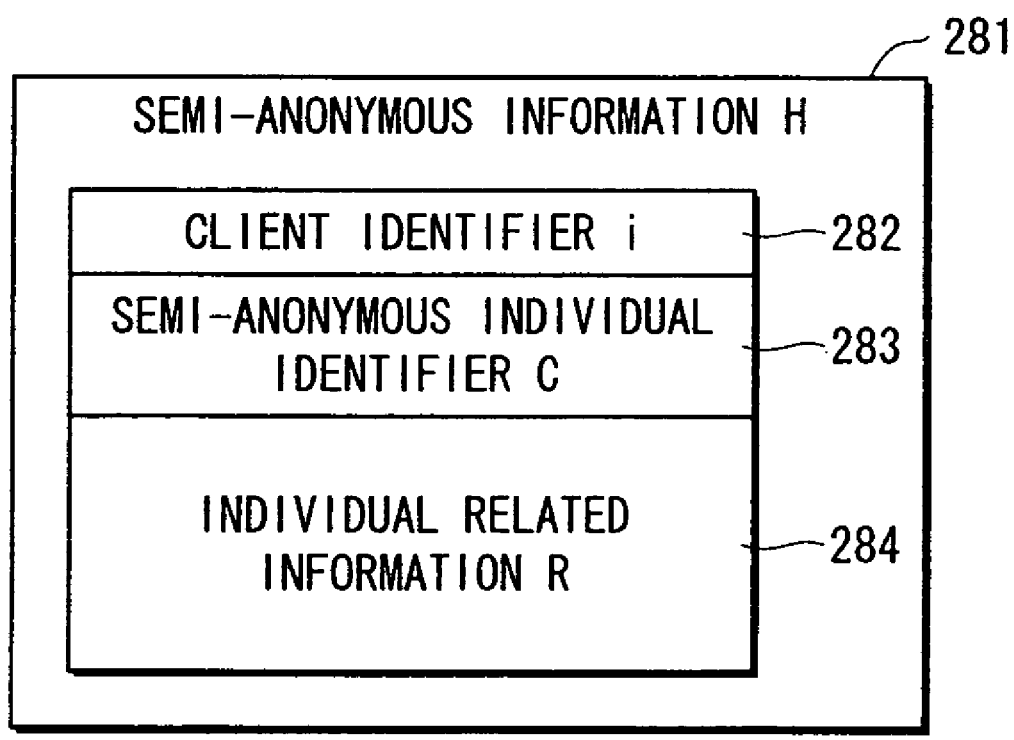
FIG. 5 shows an example data structure for semi-anonymous information H281.

As shown in FIG. 5, semi-anonymous information H 281, which is one example of the semi-anonymous information H, is composed of a client identifier i 282, a semi-anonymous individual identifier C 283, and individual related information R 284 combined in the stated order.

The combining unit 207 then outputs the generated semi-anonymous information H to the communications unit 208.

(7) Update Unit 209

The update unit 209 is described later.

1.4 Anonymity Server Device 30

Figure 6:
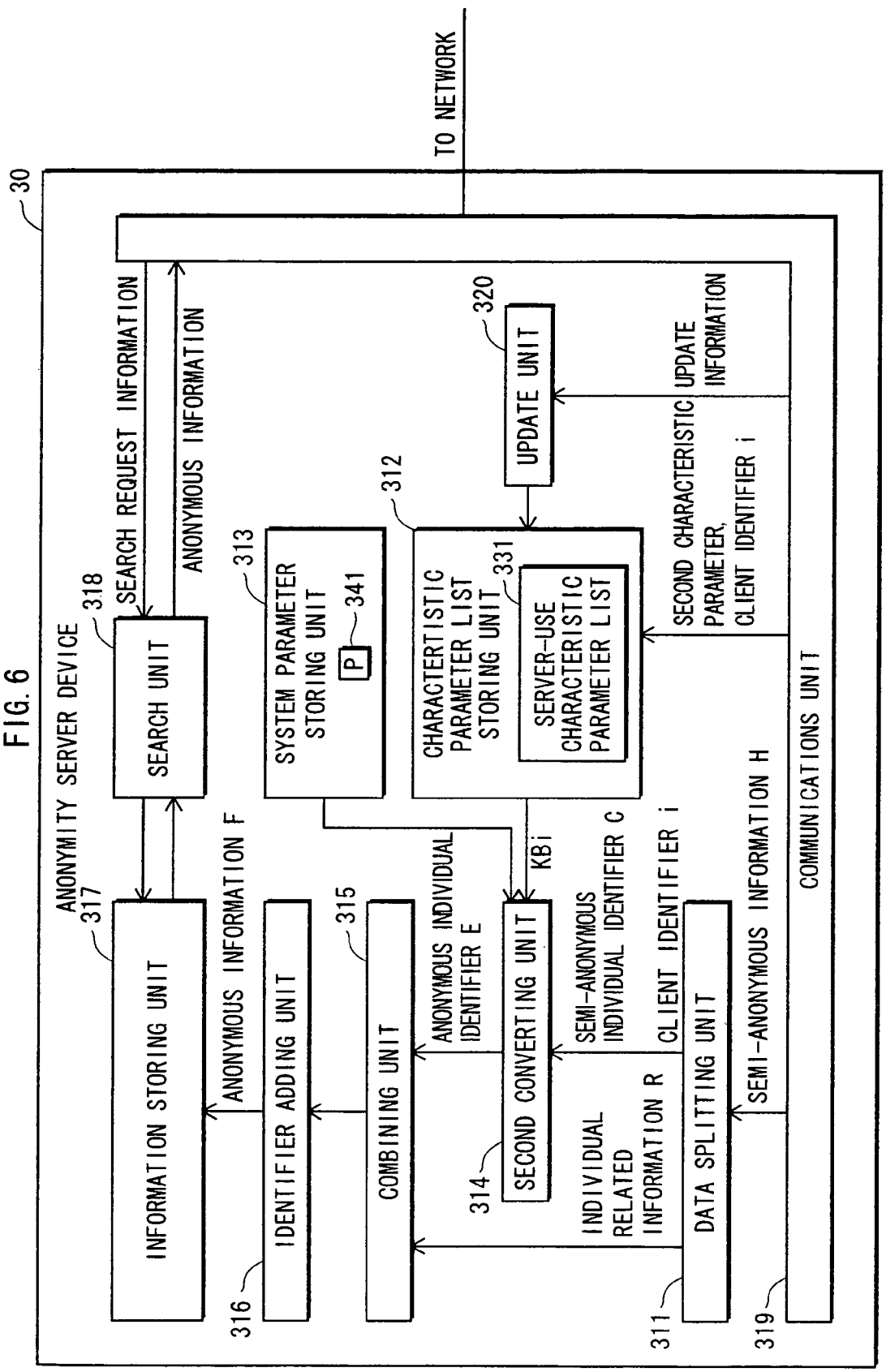
FIG. 6 is a block diagram showing the construction of the anonymity server device 30.

The anonymity server device 30 is, as shown in FIG. 6, constructed from a data splitting unit 311, a characteristic parameter list storing unit 312, a system parameter storing unit 313, a second converting unit 314, a combining unit 315, an identifier adding unit 316, an information storing unit 317, a search unit 318, a communications unit 319, and an update unit 320.

Specifically the anonymity server device 30, like the parameter generating device 10, is a computer system constructed from a microprocessor, ROM, RAM, a hard disk unit, and the like. A computer program is stored in the RAM. The anonymity server device 30 achieves a portion of its functions by means of the microprocessor operating according to the computer program.

(1) Characteristic Parameter List Storing Unit 312 and System Parameter Storing Unit 313

(Characteristic Parameter List Storing Unit 312)

The characteristic parameter list storing unit 312 stores a server-use characteristic parameter list 331.

The characteristic parameter list 331, includes, for example and as shown in FIG. 7, a region for storing a plurality of pieces server-use parameter information. Each of the plurality of pieces of server-use parameter information corresponds to a different one of the information providing devices 21, 22, 23 . . . .

Each piece of server-use parameter information includes a client identifier and a second characteristic parameter. The client identifier is identifying information for identifying the information providing device corresponding to the piece of server-use parameter information containing said client identifier. The second characteristic parameter is for use in the information providing device corresponding to the server-use parameter information containing said second characteristic parameter. Note that the client identifier and the second characteristic parameter are those described above.

The server-use characteristic parameter list 331 shown in FIG. 7 includes, for instance, pieces of server-use parameter information 332, 333, 334, . . . . The piece of server-use parameter information 332 includes the client identifier "1" and the second characteristic parameter "$KB_1$", the piece of server-use parameter information 333 includes the client identifier "2" and the second characteristic parameter "$KB_2$", and the piece of server-use parameter information 334 includes the client identifier "3" and the second characteristic parameter "$KB_3$".

Note that, though the characteristic parameter list storing unit 312 stores the pieces of server-use information corresponding to the information providing devices 21, 22, 23, . . . respectively in a list format, the pieces of server-use information may be managed using a different format providing that a target second characteristic parameter can be acquired based on the client identifier.

(System Parameter Storing Unit 313)

The system parameter storing unit 313 includes a region for storing a parameter P 341. The parameter P is that described above.

(2) Information Storing Unit 317

The information storing unit 317 includes a region for storing a plurality of pieces of anonymous information.

Each piece of anonymous information corresponds to a combination of the individual specifying information and the individual related information, and includes an anonymous information identifier, an anonymous individual identifier, and the individual related information.

The anonymous information identifier is identifying information for uniquely identifying the anonymous information containing said anonymous information identifier.

The anonymous individual identifier is generated by performing semi-anonymity processing according to Expression 4 and anonymity processing according to a later-described Expression 6 on the individual specifying information corresponding to the anonymous information containing said anonymous individual identifier.

The individual related information is the same as that described above.

The information storing unit 317, as shown in FIG. 8, stores, for instance, pieces of anonymous information 351, 361, 371, . . . .

The piece of anonymous information 351 includes an anonymous information identifier 352 "000001", an anonymous individual identifier 353 "0123456 . . .", and a piece of individual related information 354. The piece of individual related information 354 includes an examination date "1/1/2000", a diagnosed medical problem "appendicitis", prescription information "none", test results "white blood cell count . . . , blood pressure . . . ", and observations "surgery . . . ".

The piece of anonymous information 361 includes an anonymous information identifier 362 "000002", an anonymous individual identifier 363 "0325426 . . . ", and a piece of individual related information 364. The piece of individual related information 364 includes an examination date "26/3/2000", a diagnosed medical problem "appendicitis", prescription information "drug ABC", test results "white blood cell count . . . ", and observations "surgery".

The piece of anonymous information 371 includes an anonymous information identifier 372 "000003", an anonymous individual identifier 373 "0123456 . . . ", and a piece of individual related information 374. The piece of individual related information 374 includes an examination date "21/3/2001", a diagnosed medical problem "pneumonia", prescription information "drug P01", test results "blood pressure . . . ", and observations "hospitalization required".

In this way, the anonymous information identifiers 352, 362 and 372, which are included in the pieces of anonymous information 351, 361, and 371 respectively, are "000001", "000002" and "000003" respectively. Each of the anonymous information identifiers 352, 362 and 372 therefore differs from the others, and uniquely identifies one of the pieces of anonymous information 351, 361, or 371.

Further, the anonymous individual identifiers 353 and 373, which are respectively included the pieces of anonymous information 351 and 371, are "0123456 . . . " and "0123456 . . . " respectively, and are therefore identical in content. In other words, the pieces of anonymous information 351 and 371 both relate to a same patient A.

The anonymous individual identifier 363 included in the piece of anonymous information 361 differs from the anonymous individual identifiers 353 and 373. In other words, the piece of anonymous information 361 relates to a patient B, who will be different from the patient A.

(3) Communications Unit 319

The communications unit 319 receives the parameter P via the network 2 from the parameter generating device 10, and writes the received parameter P into the system parameter storing unit 313 as the parameter P 341.

Further, the communications unit 319 receives the client identifier i and the second characteristic parameter $KB_i$ via the network 2 from the parameter generating device 10, and adds the received client identifier i and second characteristic parameter $KB_i$, as a piece of server-use parameter information, to the server-use characteristic parameter list 331 that is held by the characteristic parameter list storing unit 312.

Further, the communications unit 319 receives the semi-anonymous information H from one of the information providing devices, and outputs the received semi-anonymous information H to the data splitting unit 311.

Moreover, the communications unit 319 receives the search request information from one of the information searching devices. Note that the search request information will be described later. Next the communications unit 319 outputs the received search request information to the search unit 318. Further, the communications unit 319 receives the anonymous information searched for on the basis of the received search request information, or alternatively, nonexistence information indicating the nonexistence of anonymous information that agrees with the search request information, and transmits the received anonymous information or nonexistence information via the network 2 to the information searching device that sourced the search request information.

(4) Data Splitting Unit 311

The data splitting unit 311 receives the semi-anonymous information H from the communications unit 319. On receiving the semi-anonymous information H, the data splitting unit 311 splits the received semi-anonymous information H to generate the client identifier i, the semi-anonymous individual identifier C and the individual related information R.

The splitting of the semi-anonymous information H is performed according to the lengths of the various data. In other words, since the client identifier i and the semi-anonymous individual identifier C have (fixed lengths of) 32 bits and 1024 bits respectively, the client identifier i is obtained by cutting a section data 32 bits in length from the head of the semi-anonymous information H, and the semi-anonymous individual identifier C is obtained by cutting, starting after the $32^{nd}$ bit, a further section of data 1024 bits in length. The remaining data is then the individual related information R.

The data splitting unit 311 then outputs the generated client identifier i and semi-anonymous individual identifier C to the second converting unit 314, and outputs the generated individual related information R to the combining unit 315.

(5) Second Converting Unit 314

The second converting unit 314 receives the client identifier i and the semi-anonymous individual identifier C from the data splitting unit 311. On receiving the client identifier i and the semi-anonymous individual identifier C, the second converting unit 314 extracts the piece of server-use information containing the received client identifier i from the server-use parameter list 331, and extracts the second characteristic parameter $KB_i$ from the extracted piece of server-use parameter information. Further, the second converting unit 314 reads the parameter P 341 from the system parameter storing unit 313.

Next, using the read parameter P, the extracted second characteristic parameter $KB_i$, and the received semi-anonymous individual identifier C, the second converting unit 314 calculates an anonymous individual identifier E by performing anonymity processing to according to the following expression:

$$E = (C)^{KB_i} \mod P \quad \text{(Expression 6)}$$

In other words Expression 6 indicates a repetitive multiplication.

Next, the second converting unit 314 outputs the generated anonymous individual identifier E to the combining unit 315.

(6) Combining Unit 315

The combining unit 315 receives the anonymous individual identifier E from the second converting unit 314, and receives the individual related information R from the data splitting unit 311. On receiving the anonymous individual identifier E and the individual related information R, the combining unit 315 combines the received anonymous individual identifier E and individual related information R in the stated order to obtain the combination E∥R. The combining unit 315 then outputs the combination E∥R to an identifier adding unit 316.

(7) Identifier Adding Unit 316

The identifier adding unit 316 receives the combination E∥R, and on receiving the combination E∥R, generates an anonymous information identifier J that uniquely identifies the received combination E∥R. Examples of anonymous information identifier J generated by the identifier adding unit 316 include "000001", "000002" and "000003", as described above.

Next, the identifier adding unit 316 combines the generated information identifier J and the received combination E∥R in the stated order to generate anonymous information F.

$$F = J \| E \| R \quad \text{(Expression 7)}$$

The identifier adding unit 316 then writes the generated anonymous information F into the information storing unit 317.

(8) Search Unit 18

The search unit 318 receives the search request information from the communications unit 318.

Here, the search request information includes conditions for specifying which piece of anonymous information among the plurality of pieces of anonymous information stored in the information storing unit 317 the user of the information searching device wishes to obtain.

Examples of the search request information is given below.

Example 1

"{Date of birth=1/1/2000} AND {diagnosed medical problem=appendicitis}"

Example 2

"Anonymous identifier=0123456 . . . "

The search request information shown in Example 1 indicates that anonymous information including an examination date in the individual related information of "1/1/2000" and a diagnosed medical problem of "appendicitis" is targeted by the search.

Further, the search request information shown in Example 1 indicates that anonymous information including an anonymous identifier of "0123456 . . . " is targeted.

Next, the search unit 318 searches for a piece of anonymous information that meets the conditions included in the received search request information from among the plurality of pieces of anonymous information stored in the information storing unit 317, and if one or more of such pieces of anonymous information are extracted, outputs the one or more pieces of extracted information to the communications unit 319. If none of the pieces of anonymous information meet the conditions, the search unit outputs nonexistence information indicating this fact to the communications unit 319.

(9) Update Unit 320

The update unit 320 is described later.

1.5 Information Searching Devices 41, 42, . . . .

The information searching devices 41, 42, . . . have identical constructions. Here, the construction of information searching device 41 is described and descriptions of the other information providing devices 42, . . . are omitted.

Figure 9:
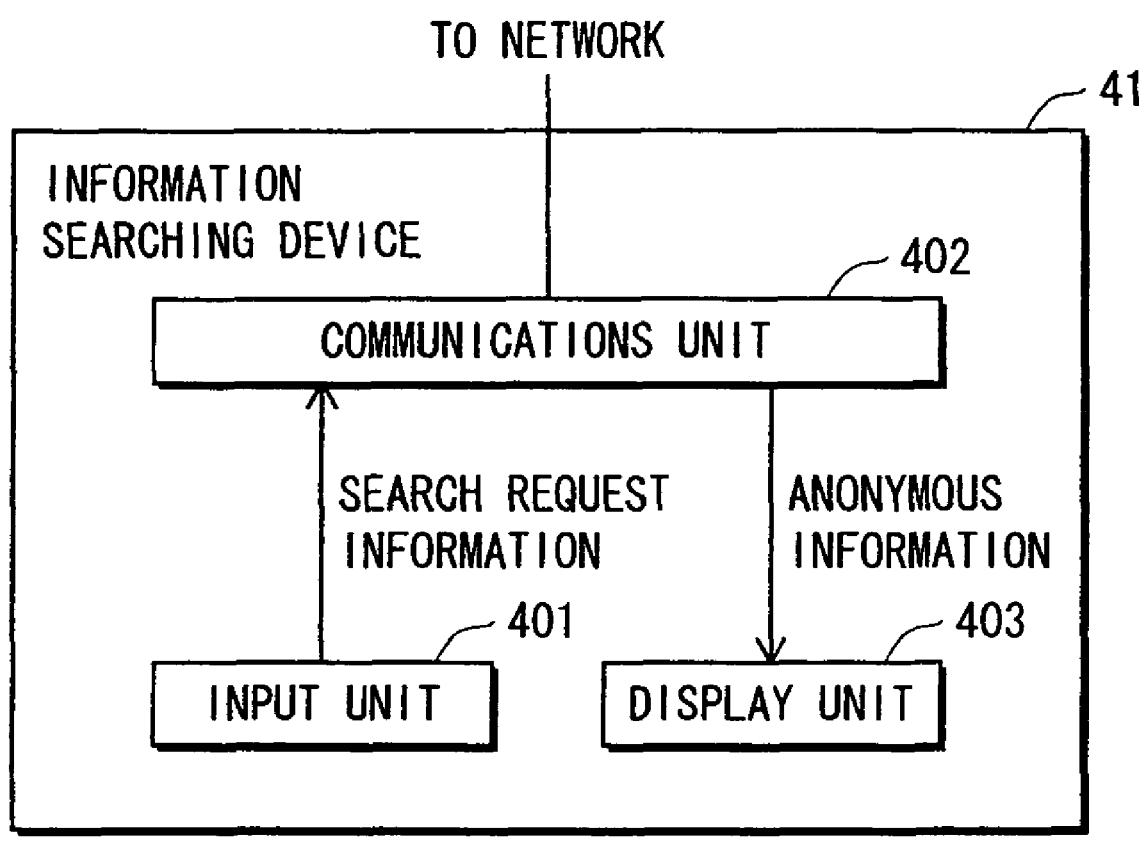
FIG. 9 is a block diagram showing the structure of the information searching device 41.

The information searching device 41 is, as shown in FIG. 9, constructed from an input unit 401, a communications unit 402 and a display unit 403.

Specifically, the information searching device 41 is a computer system constructed from a microprocessor, ROM, RAM, a hard disk unit. A computer program is stored in the RAM or the hard disk unit. The information searching device 41 achieves a portion of its functions by means of the microprocessor operating according to the computer program.

The input unit 401 receives input of the search request information from the operator of the information searching device 41, and outputs the received search request information to the communications unit 402. The search request information has the same format as that described above.

The communications unit 402 receives the search request information from the input unit 401, and transmits the received search request information via the network to the anonymity server 30. Further, the communications unit 402 receives either anonymous information or nonexistence information indicating the nonexistence of anonymous information that meets the conditions included in the search request information via the network 2 from the anonymity server 30.

The display unit 403 receives either the anonymous information or the nonexistence information from the communications unit 402, and displays whichever of the anonymous information and the nonexistence information it has received.

To be specific, the display unit 403 displays the received anonymous information or nonexistence information in a format that is perusable by the operator of the information searching device 41. For example, the display unit may display the anonymous information identifier, the anonymous individual identifier, and the individual related information on a display device such as a monitor.

At this point, the anonymous individual identifier may be displayed since the patient's individual information is not easily found from the anonymous individual identifier. However, to maintain anonymity more strictly it is acceptable not to display the anonymous individual identifier to the operator.

If this is the case, however, the operator will not be able to specify an anonymous individual identifier as a search condition in the manner of "anonymous individual identifier=0123456". Consequently, instead of accepting this type of search condition, the input unit 401 may be arranged to accept search request information that specifies the anonymous individual identifier in an indirect manner, such as the anonymous information having the same anonymous individual identifier as the anonymous information with an anonymous information identifier=98765.

1.5 Operations of Anonymous Information System 1

Here, the operations of the anonymous information system 1 are described.

(1) Operations of Parameter Generation and Distribution Using Anonymous Information System 1

Figure 10:
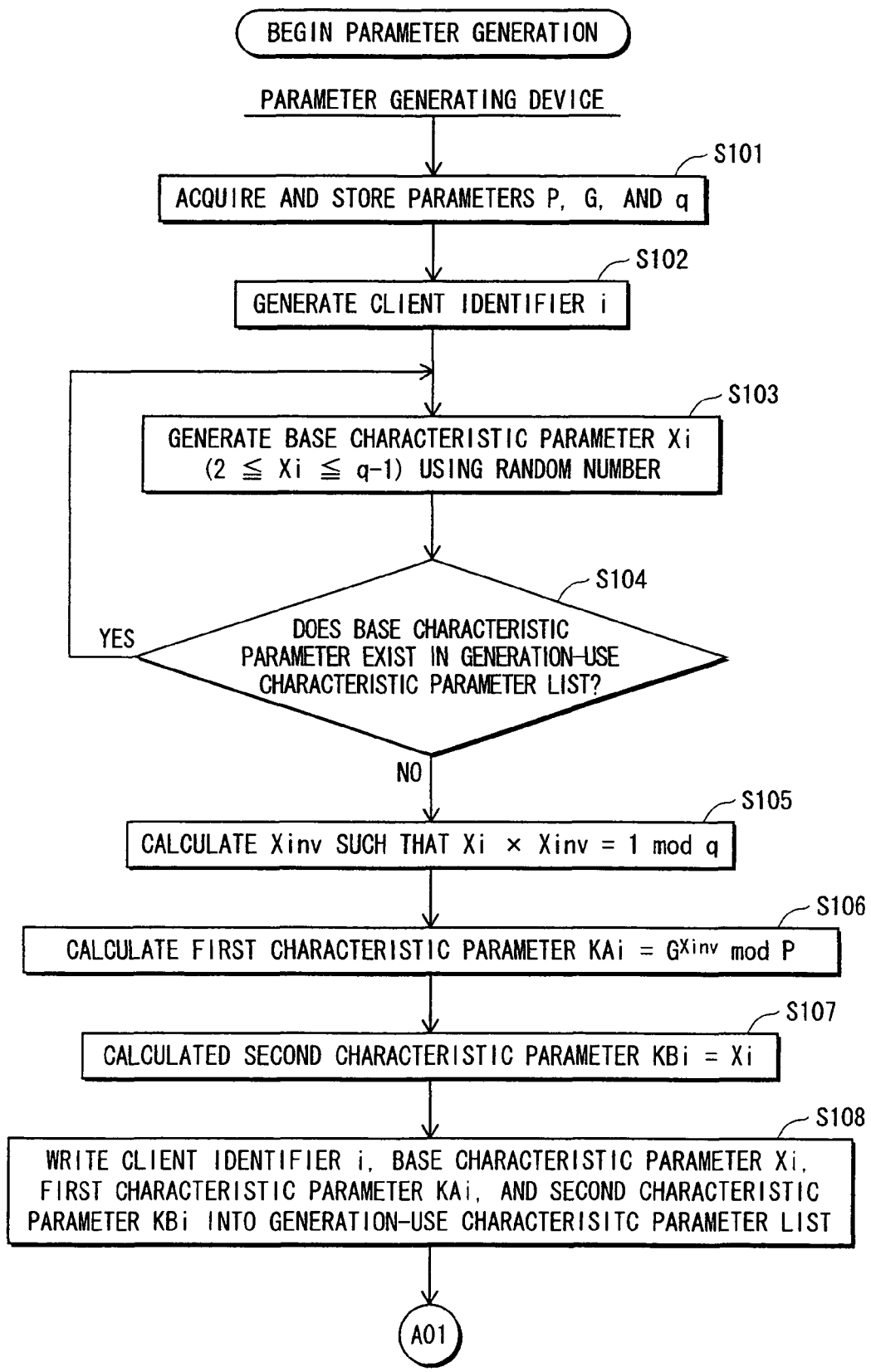
FIG. 10 is a flow-chart showing operations for the generation and distribution of parameters using the anonymous information system 1, the flow-chart being continued in FIG. 11.
Figure 11:
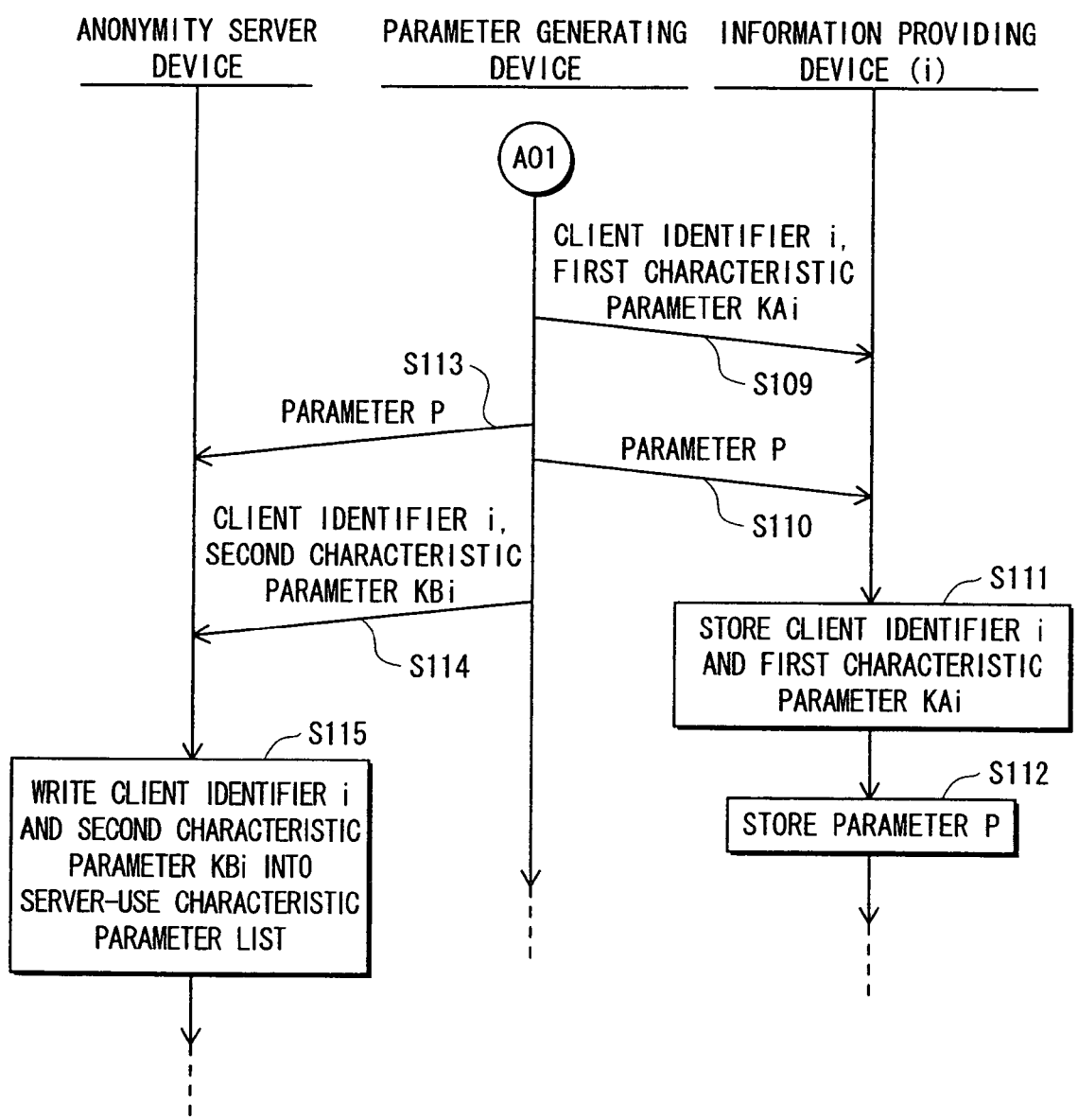
FIG. 11 is continued from FIG. 10, and is a flow-chart showing operations for the generation and distribution of parameters using anonymous information system 1.

The operations of parameter generation and distribution using the anonymous information system 1 are described with reference to the flow chart shown in FIG. 10 and FIG. 11.

The input unit 101 receives input, from the operator of the parameter generating device 10, the input consisting of the parameter P, the parameter G, and the parameter q, and the control unit 104 writes the parameter P, the parameter G, and the parameter q to the information storing unit 105 (Step S101).

Next, for a single information providing device, the parameter generating unit 103 generates a client identifier that uniquely identifies said information providing device (Step S102), generates a random number that satisfies: $2 \leq$ random number $\leq q-1$ (Step S103), and subsequently, judges whether or not the generated random number exists, as a base characteristic parameter, in the generation-use characteristic parameter list 131 of the information storing unit 105. If the generated random number does exist (YES in Step S104), the parameter generating unit 103 returns to Step S103 and once again generates a random number. If the generated random number does not exist (NO in Step S104), the parameter generating unit 103 sets the generated random number to be a base characteristic parameter $X_i$, calculates $X_{inv}$ to satisfy $X_i \times X_{inv} = 1 \mod q$ (Step S105), calculates a first characteristic parameter $KA_i$ according to $KA_i = G^{X_{inv}} \mod q$ (Step S106), and calculates a second characteristic parameter $KB_i$ according to $KB_i = X_i$ (Step S107).

Next, the parameter generating unit 103 writes a piece of generation-use parameter information, which is composed of the generated client identifier i, base characteristic parameter $X_i$, first characteristic parameter $KA_i$, and second characteristic parameter $KB_i$, into the generation-use characteristic parameter list 131 (Step S108).

Next, the communications unit 106 transmits the received client identifier i and the first characteristic parameter $KA_i$ via the network 2 to the information providing device indicated by the device designation (Step S109), and transmits the parameter P to the information providing device (Step S110). Further, the communications unit 106 transmits the parameter P via the network to the anonymity server 30 (Step S113), and transmits the client identifier i and the second characteristic parameter $KB_i$ via the network 2 to the anonymity server 30 (Step S114).

Next, the communications unit 208 of the information providing device, writes the received client identifier i into the identifier storing unit 206 and writes the first characteristic parameter $KA_i$ into the characteristic parameter storing unit 204 (Step S111), and writes the parameter P into the system parameter storing unit 203 (Step S112).

Further, the communications unit 319 of the anonymity server 30 writes the parameter P into the system parameter storing unit 313 as the parameter P 341, and writes the client identifier i and the second characteristic parameter $KB_i$ into the characteristic parameter list storing unit 312 (Step S115).

(2) Operations of Semi-Anonymous Information Generation Using Information Providing System 21

Figure 12:
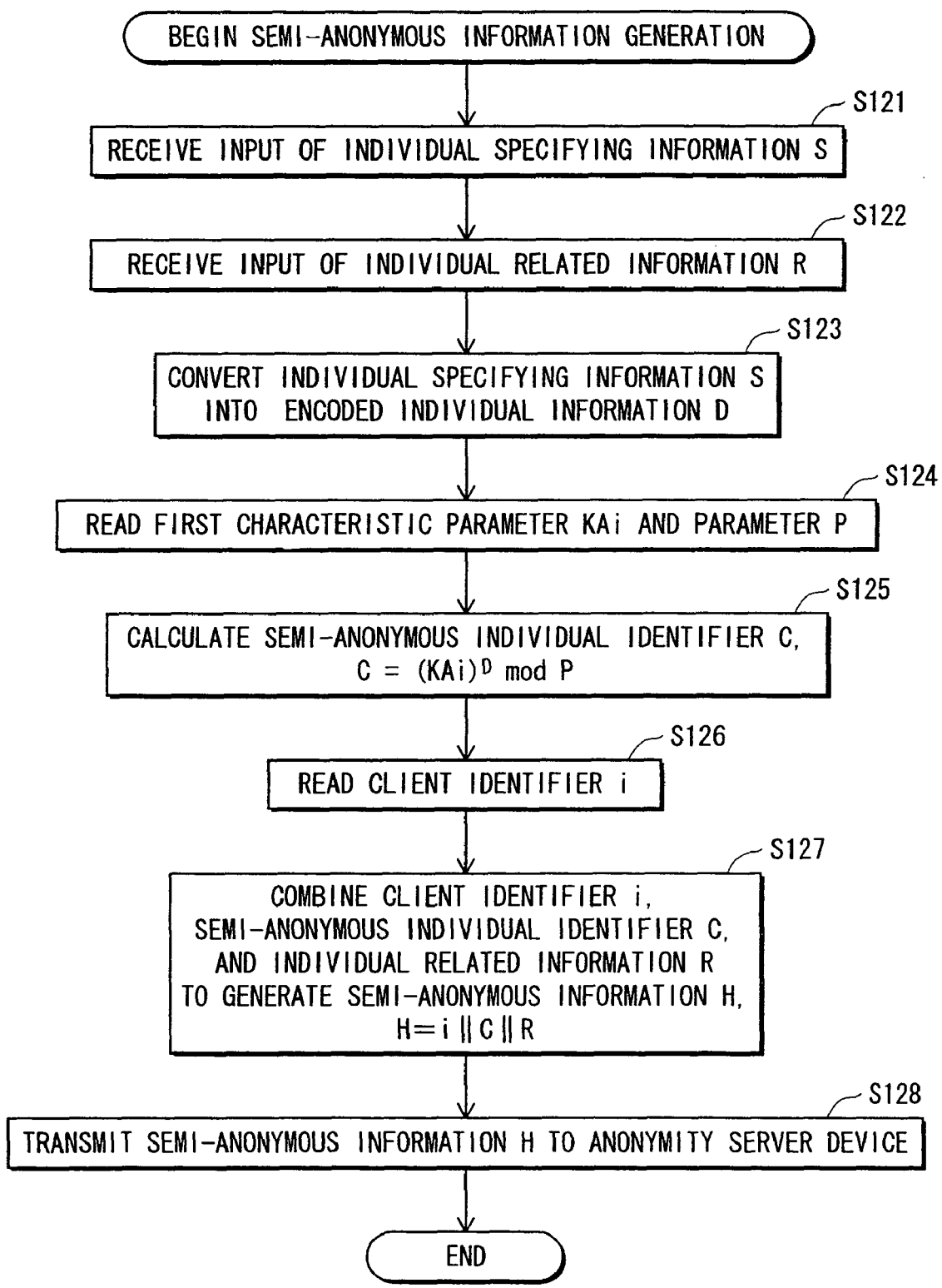
FIG. 12 is a flow-chart showing operations for generating semi-anonymous information using an information providing device 21.

The operations of semi-anonymous information generation using the information providing system 21 are described with reference to the flow chart shown in FIG. 12.

The input unit 201 receives input including the individual specifying information S (Step S121) and further receives individual related information R from the operator of the information providing device 21 (Step S122), and the encoder unit 202 generates the encoded individual information D from the individual specifying information S (Step S123).

Next, the first converting unit 205 reads the parameter P 231 from the system parameter storing unit 203 and reads the first characteristic parameter $KA_i$ 241 from the characteristic parameter storing unit 204 (Step S124), and using the encoded individual information D, and the read parameter P 231 and first characteristic parameter $KA_i$ 241, the first converting unit 205 generates the semi-anonymous individual identifier C according to the following expression: $C = (KA_i)^D \mod P$ (Step S125).

Next, the combining unit 207 reads the client identifier i 251 from the identifier storing unit 206 (Step S126), and combines the client identifier i 251, the semi-anonymous individual identifier C, and the individual related information R in the stated order to generate the semi-anonymous information H, such that $H = i \| C \| R$ (Step S127).

Next, the communications unit 208 transmits the semi-anonymous information H via the network 2 to the anonymity server device 30 (Step S128).

(3) Operations of Anonymous Information Generation Using Anonymity Server Device 30

Figure 13:
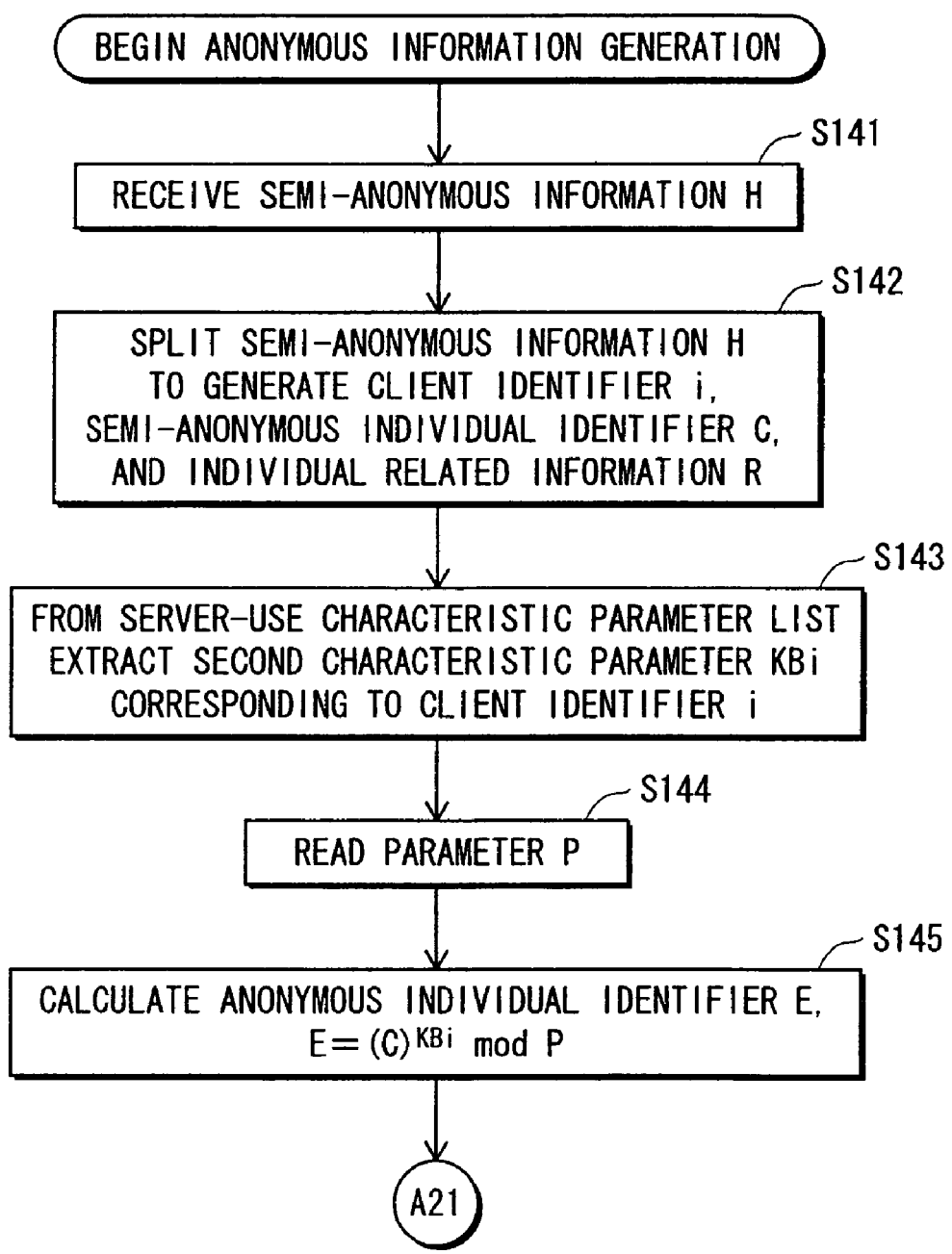
FIG. 13 is a flow-chart showing operations for generating semi-anonymous information using an anonymity server device 30, the flow-chart being continued in FIG. 14.
Figure 14:
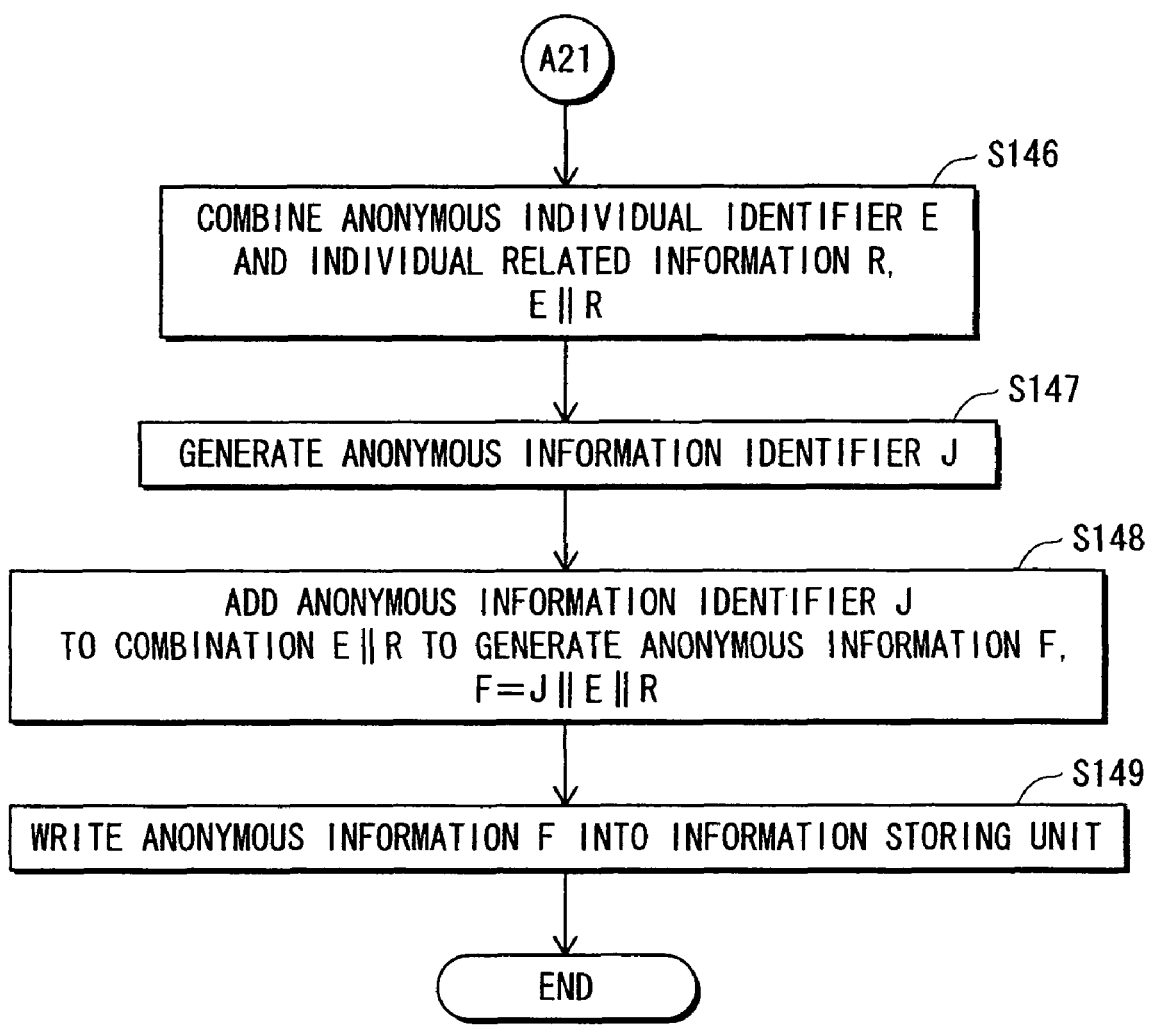
FIG. 14 is continued from FIG. 13, and is a flow-chart showing operations for generating semi-anonymous information using an anonymity server device 30.

Here, the operations of anonymous information generation using the anonymity server device 30 are described with reference to the flow chart shown in FIG. 13 and FIG. 14.

The communications unit 319 of the anonymity server device 30 receives a piece of semi-anonymous information H from one of the information providing devices (Step S141), the data splitting unit 311 splits the received piece of semi-anonymous information H and generates the client identifier i, the semi-anonymous individual identifier C, and the individual related information R (Step S142). The second converting unit 314 extracts a piece of server-use parameter information that includes the client identifier i from the server-use characteristic parameter list 331, and extracts the second characteristic parameter $KB_i$ from the extracted piece of server-use parameter information (Step S143). Further, the second converting unit 314 reads the parameter P 341 from the system parameter storing unit 313 (Step S144), and using the read parameter P, the extracted second characteristic parameter $KB_i$, and the received semi-anonymous information identifier C, calculates the anonymous individual identifier E according to the following expression: $E = (C)^{KB_i} \mod P$ (Step S145).

Next, the combining unit 315, combines the anonymous individual identifier E and the individual related information R in the stated order to obtain the combination $E \| R$ (Step S146). The identifier adding unit 316 then generates an anonymous information identifier J that uniquely identifies the combination $E \| R$ (Step S147), and combines the generated anonymous information identifier J and the received combination $E \| R$ in the stated order to generated the anonymous information $F = J \| E \| R$ (Step S148).

Next, the identifier adding unit 316 writes the generated anonymous information F into the information storing unit 317 (Step S149).

(4) Operations of Anonymous Information Search

Figure 15:
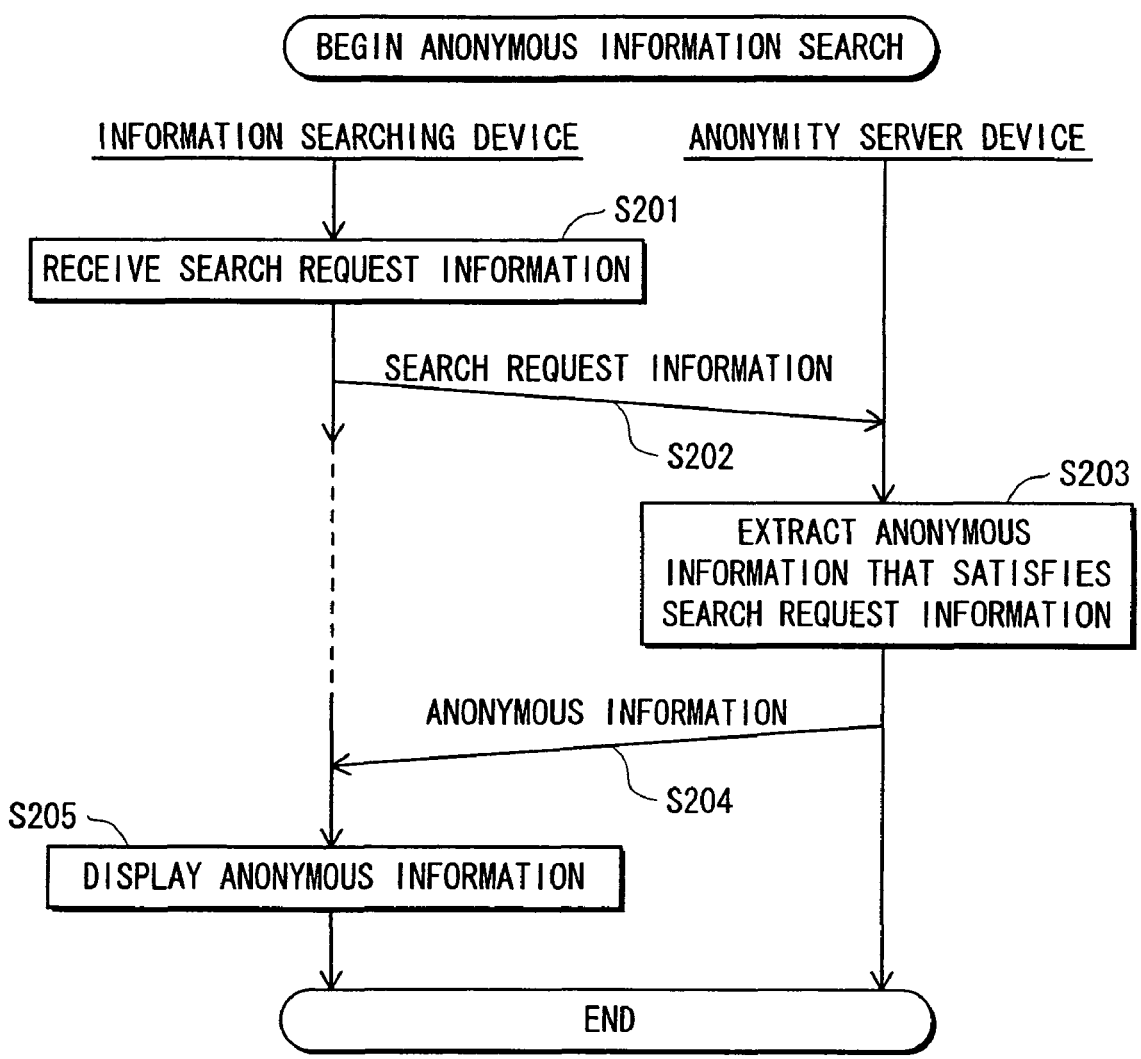
FIG. 15 is a flow-chart showing anonymous information search operations using the anonymous information system 1.

Here, the operations of the anonymous information search using the anonymous information system 1 are described with reference to the flow chart shown in FIG. 15.

The input unit 401 of the information searching device 41 receives input of a piece of search request information from the operator of the information searching device (Step S201), and the communications unit 402 transmits the inputted piece of search request information via the network 2 to the anonymity server device 30 (Step S202).

The search unit 318 of the anonymity server device 30 receives the piece of search request information (Step S202), and extracts, from the information storing unit 317, the anonymous information that meets the conditions indicated in the received piece of search information (Step S203). The communications unit 318 transmits the extracted anonymous information via the network 2 to the information searching unit 41 (Step S204).

The communications unit 402 of the information searching device 41 receives the anonymous information (Step S204), and the display unit 403 displays the anonymous information (Step S205).

1.6 Relationship Between Semi-Anonymity Processing Using First Converting Unit 205 and Anonymity Processing Using Second Converting Unit 314

The relationships among the encoded individual information D generated by the encoding unit 202, the semi-anonymous individual identifier C generated by the first converting unit 205, and the anonymous individual identifier E generated by the second converting unit 314 are described below.

Figure 16:
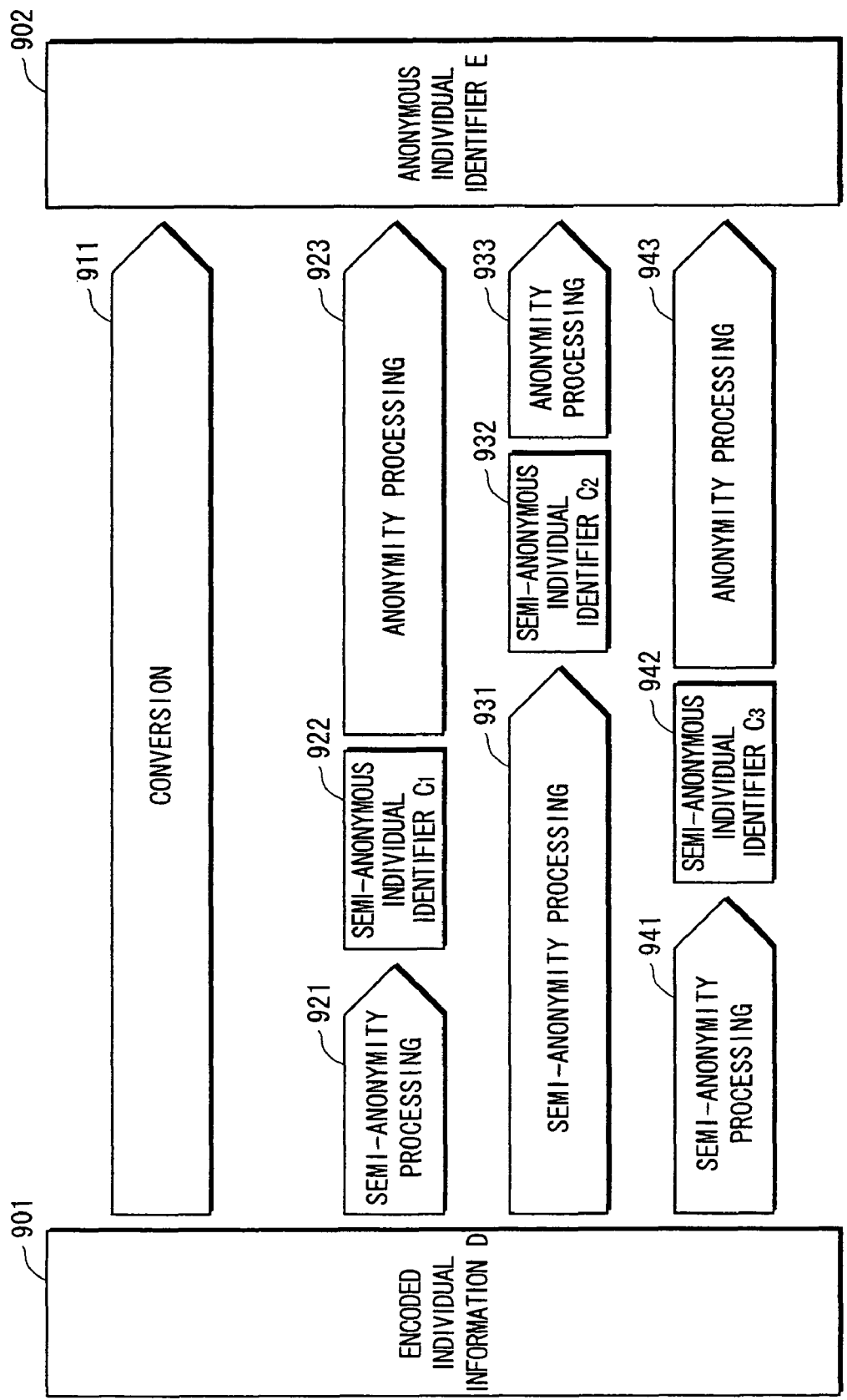
FIG. 16 shows conceptually a relationship among encoded individual information D, a semi-anonymous individual identifier C, and an anonymous individual identifier E.

The relationships among the encoded individual information D, the semi-anonymous individual identifier C and the anonymous individual identifier E are shown conceptually in FIG. 16.

In the prior art, a conversion 911 is performed on encoded individual information D 901 to generate an anonymous individual identifier E 902. The conversion 911 is performed by one of the information providing device and the anonymity server device, and the obtained anonymous individual identifier E is stored in a database of the anonymity server device. However, when the prior art of this kind is used, the following problems arises.

Firstly, consider the case in which the conversion 911 is performed at the information providing device. In this case, the information providing device knows the algorithm for the conversion 911, and can therefore find the anonymous individual identifier E by performing the conversion 911 on any of the pieces of encoded individual information.

Now, consider, for example, the case in which there is a user who maintains a terminal that functions both as an information providing device and an information searching device and the user uses the information providing device function, the algorithm of the conversion 911 in other words, to calculate the anonymous individual identifier E for a piece of encoded individual information D belonging to a specific person A. The user then uses the information searching device function to perform a search for a new piece of anonymous information having the anonymous individual identifier E. In this case, the user knows that the searched-for new piece of anonymous information relates to the person A, and the anonymity of the new piece of anonymous information is therefore lost. This is a problem.

Secondly, consider the case in which the conversion 911 is performed at the anonymity server device. In this case, since the information providing device does not know the conversion 911, problems of the type described above do not occur. However, in this case, the information providing device has to transmit the individual specifying information accompanied by the individual related information to the anonymity server device, and there is therefore a risk that a third party will be listening in when the individual specifying information is being transmitted from the information providing device to the anonymity server. Further, there is a risk that individual specifying information will be illegitimately added to the anonymity server device 30. These risks are a problem.

In the present invention, on the other hand, the conversion 911 is split, as shown in FIG. 16, into semi-anonymity processing 921 and anonymity processing 923, the semi-anonymity processing 921 being performed by the information providing device 21, and the anonymity processing 923 being performed by the anonymity server device 30.

With this method, the information providing device 21 can only execute a portion of the conversion 911, and consequently, cannot find the anonymous individual identifier from the encoded individual information. Hence the problems that arise due to the conversion 911 being performed at the information providing device do not occur.

Further, since it is the semi-anonymous identifier C obtained by performing semi-anonymity processing on the encoded individual information D that is transmitted to the anonymity server device 30, the problems that arise due to the conversion 911 being performed at the anonymity server do not occur.

1.7 Relationships Among Semi-Anonymity Processes at Plurality of Information Providing Devices In the present invention a higher level of safety is realized by varying the way in which the conversion 911 is split between the semi-anonymity processing and the anonymity processing for each information providing device.

For example, in FIG. 16, the information providing device 21 performs semi-anonymity processing 921 on the encoded information D to calculate semi-anonymous individual identifier C1 922, and transmits the obtained semi-anonymous individual identifier C1 to the anonymity server device 30. In this case, the anonymity server device 30 performs anonymity processing 923 on the semi-anonymous individual identifier C1 922 transmitted from the information providing device to find the anonymous individual identifier E.

Further, the information providing device 22 performs semi-anonymity processing 931 on the encoded information D to calculate semi-anonymous individual identifier C2 932, and transmits the obtained semi-anonymous individual identifier C2 to the anonymity server device 30. In this case, the anonymity server device 30 performs anonymity processing 933 on the semi-anonymous individual identifier C2 932 transmitted from the information providing device to find the anonymous individual identifier E.

Moreover, the information providing device 23 performs semi-anonymity processing 941 on the encoded information D to calculate semi-anonymous individual identifier C3 942, and transmits the obtained semi-anonymous individual identifier C3 to the anonymity server device 30. In this case, the anonymity server device 30 performs anonymity processing 943 on the semi-anonymous individual identifier C3 942 transmitted from the information providing device to find the anonymous individual identifier E.

Here, the semi-anonymity processing 921, semi-anonymity processing 931, and semi-anonymity processing 941 each use a different first characteristic parameter. Consequently, the information providing device 21 cannot find the characteristic first parameter used by the information providing device 22 from the first characteristic parameter used by itself. Thus, an information providing device cannot discover what semi-anonymity processing is being performed by the other information providing devices from the content of its own semi-anonymity processing.

Though, with the above arrangement, the semi-anonymity processing performed by each information processing device is different, corresponding anonymity processing is used for each of the information providing devices is used, and consequently, when taken as whole this method is equivalent to performing the single conversion 911. This is to say that if the pieces of encoded information D are the same, even if they pass through different information devices, the anonymous individual identifiers E obtained at the end of the process will be idenitical.

Using other semi-anonymity processing for each information providing device in the manner described above has the following advantages.

Suppose that the semi-anonymity processing were common to all the information providing devices and that the algorithm for the semi-anonymity processing had leaked from one of the information providing devices, and had thereby been disclosed. While it is true that provided the anonymity processing stored by anonymity server device 30 were not disclosed the anonymity of the anonymous information would not be lost immediately, the anonymity of the information in the anonymity server device would be entirely dependent on the secrecy of the anonymity processing. It would therefore be desirable for the semi-anonymity processing and the anonymity processing to be updated. However, since the semi-anonymity processing would be common to all the information processing devices, the semi-anonymity processing would have to be updated in all the information processing devices, and were the number of information providing devices to be very large, this update would require a great deal of time and effort.

However, if the semi-anonymity processing is varied for each information providing device as in the present invention, even if the semi-anonymity processing of one of the information providing devices is exposed, only the semi-anonymity processing for that information device need be updated. Moreover, only the anonymity processing that corresponds to this semi-anonymity processing need be updated. Thus, compared with the case described above, the time and effort required for the update is greatly reduced.

1.8 Considerations Concerning Semi-Anonymity Processing and Anonymity Processing.

Certain advantages of the semi-anonymity processing and anonymity processing disclosed in the embodiment of the present invention are described below.

Advantage 1: The semi-anonymity processing differs for each device, and consequently it is not possible, from the semi-anonymity processing of one information processing device, to discover the semi-anonymity processing of any of the other information processing devices.

Advantage 2: Using its own semi-anonymity processing, the information providing device cannot find either the anonymity processing corresponding to itself in the anonymity server device, nor the anonymity processing corresponding to any of the other information providing devices in the anonymity server device.

Advantage 3: Provided the semi-anonymity processing and anonymity processing are performed in turn, the results of the conversion process will be the same whichever information providing device is used.

Firstly, Advantage 1 can be explained by the following.

The semi-anonymity processing is executed by calculating an output C from an input D according to the following expression:

$$C = (KA)\hat{} D \bmod P$$

Here P is a common value throughout the system, but KA is calculated using Expression 8 and Expression 9 for each information providing device.

$$X_i \times X_{inv} = 1 \bmod q \qquad \text{(Expression 8)}$$

$$KA = G\hat{}(X_{inv}) \bmod q \qquad \text{(Expression 9)}$$

Here, in Expression 8, since X is generated randomly for each information providing device, $X_{inv}$ is also determined randomly. In Expression 9, P and G are values that are common throughout the system, but since $X_{inv}$ is determined randomly it is clear that KA will also be determined randomly. Further, it is arranged that no two or more information providing devices use the same X. Further, KA is determined such that there is no overlap among the information providing devices. The above description has shown how the properties of Advantage 1 are realized.

Secondly, for Advantage 2 can be realized provided that it is very difficult for an information providing device find the parameter KB, which is necessary in the anonymity processing, from the pieces of information KA and G held by information providing device itself.

$$KB = X \qquad \text{(Expression 10)}$$

It is clear from Expression 10 that KB is X, and to find X it is necessary to know $X_{inv}$ from Expression 8. According to Expression 9, $X_{inv}$ can be found from KA and G, and P. However, to find $X_{inv}$ in this way is computationally infeasible as it is necessary to solve a discrete algorithm problem in GF(P). Further, the value of KA is calculated from a randomly selected X based on Expression 8 and Expression 9 and there is therefore no predetermined relationship among the values of KA stored by the various information providing devices. Consequently, one information providing device cannot, from the value of KA it is holding itself, find the value of KA held by other information providing devices. The above description has shown how Advantage 2 is realized.

Thirdly, Advantage 3 is realized as follows.

The semi-anonymous individual identifier C is calculated from the encoded individual information D as follows using Expression 11.

$$C = (KA)\hat{} D \bmod P \qquad \text{(Expression 11)}$$

Moreover, anonymous individual identifier E is calculated from the semi-anonymous individual identifier C as follows using Expression 12.

$$E = C\hat{}(KB) \bmod P \qquad \text{(Expression 12)}$$

From Expression 11 and Expression 12 it can be seen that $$E = \{(KA) \wedge D\} \wedge (KB) \bmod P$$
$$= (KA) \wedge (D \times KB) \bmod P$$

holds true. Here, using Expression 8 and Expression 9 it is further possible to transform the above expression to give $$E = \{G \wedge (X_{inv})\} \wedge (D \times X) \bmod P$$
$$= G \wedge (X_{inv} \times X \times D) \bmod P$$

and Expression 8 gives the relationship $$E = G\hat{} D \bmod P$$

The above expression holds true for all values of KA and KB that satisfy Expression 8 through Expression 10, and therefore Advantage 3 is realized.

From the above, it is clear that Advantage 1, Advantage 2 and Advantage 2 can be realized.

1.9 Characteristic Parameter Update Example (1)

To say that the semi-anonymity processing used by the first converting unit 205 of the information providing device 21 has been exposed is to mean that the first characteristic parameter KA, which is being stored in the information providing device 21, has been exposed.

Here, an order of operations is described for updating semi-anonymity processing of an information providing device when the semi-anonymity processing at the same information processing device has been exposed.

(1) Construction of Parameter Generating Device 10

In addition to the functions described above, the input unit 101 further receives, from the operator of the parameter generating device 10, input consisting of a parameter generation instruction that indicates parameters are to be generated for a specific information providing device, and a client identifier that identifies the information providing device that has been exposed, and outputs the inputted parameter generation instruction and client identifier to the control unit 104.

In addition to the functions described above, the control unit 104 receives the parameter generation instruction and the client identifier. On receiving the parameter generation instruction and the client identifier, the control unit 104 outputs (i) a parameter regeneration instruction that indicates a base characteristic parameter, a first characteristic parameter, and a second characteristic parameter are to be newly generated and put in correspondence with the client identifier, and (ii) the client identifier.

In addition to the functions described above, the parameter generating unit 103 receives the parameter generating instruction and the client identifier. On receiving the parameter generating instruction and the client identifier, the parameter generating unit 103 again generates a base characteristic parameter, a first characteristic parameter, and a second characteristic parameter for the received client identifier in the way described above. Further, the parameter generating unit 103 deletes the piece of generation-use parameter information that includes the client identifier from the generation-use characteristic parameter list 131, and adds to the generation-use characteristic parameter list 131 a piece of generation-use parameter information composed of the client identifier, the regenerated base characteristic parameter, the regenerated first characteristic parameter and the regenerated second characteristic parameter. The parameter generating unit 103 then outputs the regenerated first characteristic parameter and the regenerated second characteristic parameter to the control unit 104.

The control unit 104 further receives the regenerated first characteristic parameter and the regenerated second characteristic parameter, outputs the client identifier, the first characteristic parameter, the second characteristic parameter, and a piece of device designating information that indicates the information providing device indicated by the client identifier to the communications unit 106. Further the control unit 104 outputs to the communications unit (i) a first update instruction indicating that the parameter update instruction and the first characteristic parameter are to be transmitted to the information providing device designated by the piece of device designation information and (ii) a second update instruction indicating that the parameter update instruction, the client identifier, and the second characteristic parameter are to be transmitted to the anonymity server device 30.

In addition to the functions described above, the communications unit 106 receives the client identifier, the first characteristic parameter, the second characteristic parameter and the piece of device designating information from the control unit 104. Further the communications unit 106 receives the first update instruction and the second update instruction from the control unit 104.

On receiving the first update instruction and the second update instruction, the communications unit 106 transmits an update instruction that indicates a parameter update and the first characteristic parameter via the network 2 to the information providing device indicated by the piece of device designation information. Next, the communications unit 106 transmits an update instruction that indicates a parameter update, the client identifier, and the second individual parameter via the network 2 to the anonymity server device 30.

(2) Construction of Information Providing Device 21

The communications unit 208 receives the update instruction that indicates a parameter update and the first characteristic parameter. On receiving the update instruction and the first characteristic parameter, the communications unit 208 outputs the received first characteristic parameter, as a piece of update information, to the update unit 202.

The update unit 202 receives the first characteristic parameter, as a piece of update information, from the update unit 202. On receiving the first characteristic parameter, the update unit 202 deletes the first characteristic parameter $KA_i$ that is being stored in the characteristic parameter storing unit 204, and adds the newly received first characteristic parameter by writing the newly received first characteristic parameter into the characteristic parameter storing unit 204.

(3) Construction of Anonymity Server Device 30

The communications device 319 receives the update instruction indicating parameter update, the client identifier, and the second characteristic parameter via the network 2 from the parameter generating device 10. On receiving the update instruction, the client identifier, and the second characteristic parameter, the communications unit 319 outputs the received client identifier and second characteristic parameter to the update unit 320.

The update unit 320 receives the client identifier and the second characteristic parameter as update information from the communications unit 319. On receiving the client identifier and the second characteristic parameter, the update unit 320 deletes the piece of server-use parameter information that includes the received client identifier from the server-use characteristic parameter list 331 being stored in the characteristic parameter list storing unit 312, and adds the newly received client identifier and second characteristic parameter to the server-use characteristic parameter list 331

(4) Operations after Parameters Have Been Updated

After the parameters have been updated, the first converting unit 205 of the information providing device 21 uses the updated first characteristic parameter in the manner described above to generate the semi-anonymous individual identifier C from the encoded individual information D.

After the parameters have been updated, the second converting unit 314 of the anonymity sever device 30 uses the updated second characteristic parameter in the manner described above to generate the anonymous individual identifier E from the semi-anonymous individual identifier C.

1.10 Characteristic Parameter Update Example (2)

The above is a description of a method for restoring safety of the anonymity system 1 in the unlikely event that the first characteristic parameter being held secretly in the information providing device 21 is exposed by theft, or the like. This method involves updating the exposed first characteristic parameter with a new characteristic parameter.

However, if both the first characteristic parameter being held secretly in the information providing device 21 and the second characteristic parameter corresponding to the information providing device 21 and being held in the anonymity server device 30 are exposed, the entire process for converting from the encoded individual information to the anonymous individual information will be exposed, and the anonymity of the anonymous information stored in the anonymity server device 30 will be lost. Consequently, it will not be possible to restore the safety of the anonymous information system 1 using the type of parameter update method described above.

Moreover, even the first and second characteristic parameters are not exposed in the way described, the safety of anonymous information system 1 will depends on the number of bits used for the parameter P. Consequently, the same problem would occur if due to some improvement in computational performance a sufficient level of safety could no longer be guaranteed using the current parameter P. In this case, the process for converting from the encoded individual information to the anonymous individual identifier, in other words the conversion process itself, is updated in the manner described below.

(1) Construction of Parameter Generating Device 10

In addition to the functions described above, the input unit 101 further receives, from the operator of the parameter generating device 10, an instruction indicating an update of the conversion processing and of the parameters across the whole of the anonymous information system 1. On receiving the instruction, the input unit 105 receives input of a new parameter P', a new parameter G' and a new parameter q', and outputs the parameter P', the parameter G' and the parameter q' to the control unit 104.

Here the parameter P', the parameter G' and the parameter q' have the same properties as, but different values to, the parameter P, the parameter G, and the parameter q respectively.

The control unit 104 further receives the parameter P', the parameter G', and the parameter q' from the input unit and writes the received parameter P', parameter G' and parameter q' into the information storing unit 105.

Further, in addition to the functions described above, the control unit 104 reads all the pieces of generation-use parameter information from the generation-use characteristic parameter list 131, and outputs, to the parameter generating unit 103, a parameter regeneration instruction instructing that new characteristic parameters are to be generated for each of the information providing devices identified by the client identifiers included in the read pieces of generation-use parameter information.

Next, for each information providing device identified by the client identifiers, the control unit 104 further receives a new first characteristic parameter $JA_i$ and a new second characteristic parameter $JB_i$ from the parameter generating unit 103. On receiving the first characteristic parameter $JA_i$ and the second characteristic parameter $JB_i$, the control unit 104 outputs, to the communications unit 106, a client identifier i, the first characteristic parameter $JA_i$, the second characteristic parameter $JB_i$, and a device designation that indicates the corresponding information providing device. Further the control unit 104 outputs to the communications unit 106 (a) a first transmission instruction indicating that the parameter G, the parameter P', the client identifier i, and the first characteristic parameter $JA_i$ are to be transmitted to the information providing device of the device designation and (b) a second transmission instruction indicating that the client identifier i and the second characteristic parameter $JB_i$ are to be transmitted to the anonymity server device 30.

Here, The parameter generating device 10 discloses parameter G, but conceals G'.

The parameter generating unit 103 receives the parameter generating instruction from the control unit 104.

On receiving the parameter generating instruction, the parameter generating unit 103 reads, for a given information providing device, the parameter P', the parameter G', and the parameter q' from the storing unit 105.

Next, the parameter generating unit 103 generates a random number that is greater than "1" but less than q'. In other words it generates a random number that satisfies: $2 \leq$ random number $\leq q'-1$. Next the parameter generating unit 103 judges whether or not the generated random number exists, as a base characteristic parameter, in the generation-use characteristic parameter list 131 of the information storing unit 105. If the generated random number exists, the parameter generating unit 103 again generates a random number. If the generated random number does not exist in the generation-use characteristic parameter list 131, the parameter generating unit 103 sets generated random number to be a base characteristic parameter $Y_i$, and calculates $Y_{inv}$ to satisfy:

$$Y_i \times Y_{inv} = 1 \bmod q' \quad \text{(Expression 13)}.$$

Next, the parameter generating unit 103 calculates a first characteristic parameter $JA_i$ according to:

$$JA_i = G'Y_{inv} \bmod q' \quad \text{(Expression 14)}.$$

Next the parameter generating unit 103 calculates a second characteristic parameter $JB_i$ according to:

$$JB_i = Y_i \quad \text{(Expression 15)}$$

Next the parameter generating unit 103 writes the generation-use parameter information, which is constructed from the generated client identifier i, base characteristic parameter $Y_i$, first characteristic parameter $JA_i$, and second characteristic parameter $JB_i$, into the generation-use characteristic parameter list 131.

On completing the writing of the generation-use parameter information, the parameter generating unit 103 outputs to the control unit 104 the first characteristic parameter $JA_i$, and second characteristic parameter $JB_i$.

Note that the generation of the first and second characteristic parameters is performed separately for each information providing device. Thus, the first and second characteristic parameters will have different values for each information providing device. The client identifiers for identifying the information providing devices and second characteristic parameters are stored as a list in the characteristic parameter list storing unit 312 in the anonymity server device 30.

The communications unit 106 receives, from the control unit 104, the client identifier i, the first characteristic parameter $JA_i$, the second characteristic parameter $JB_i$, and the device designation, and further receives the first transmission instruction and the second transmission instruction.

On receiving the first transmission instruction and the second transmission instruction, the communications unit 106 reads the parameter G and the parameter P' from the information storing unit 105, and transmits the read parameter G and the read parameter P', and the received client identifier i and first characteristic parameter $JA_i$, via the network 2 to the information providing device indicated by the device designation. Next, the communications unit 106 transmits the read parameter P', the received client identifier i, and the second characteristic parameter $JB_i$ via the network 2 to the anonymity server device 30.

(2) Construction of Information Providing Device 21

The system parameter storing unit 203 further includes a region for storing the parameter P'.

The characteristic storing unit 204 further includes a region for storing the first characteristic parameter $JA_i$.

The communications unit 208 further receives the parameter G, the parameter P', and the first characteristic parameter $JA_i$ via the network 2 from the parameter generating device 10. On receiving the parameter G, the parameter P', and the first characteristic parameter $JA_i$, the communications unit 208 writes the received parameter G and the received parameter P' into the system parameter storing unit 203, and writes the received first characteristic parameter $JA_i$ into the characteristic parameter storing unit 204.

The input unit 201 further receives input of the individual specifying information S and the individual related information R from the operator of the information providing device 21.

The encoder unit 202 further converts the individual specifying information S into the encoded individual information D.

In addition to the functions described above, on receiving the encoded individual information D, the first converting unit 205 reads the parameter G, the parameter P 231, and the parameter P' from the system parameter storing unit 203, and reads the first characteristic parameter Jai from the characteristic parameter storing unit 204. Using the encoded individual information D, the parameter G, and the parameter P231, the first converting unit 205 then calculates the anonymous individual identifier E.

$$E = G^D \bmod P \quad \text{(Expression 16)}$$

Next, using the calculated parameter E, the read parameter P', and the read first characteristic parameter $JA_i$, the first converting unit 205 generates a semi-anonymous individual identifier C' by performing semi-anonymity processing according to the following expression.

$$C' = (JA_i)^E \bmod P' \quad \text{(Expression 17)}$$

The first converting unit 205 then outputs the generated semi-anonymous identifier C' to the combining unit 207.

The combining unit 207 receives the individual related information R from the input unit 201, and receives the semi-anonymous individual identifier C' from the first converting unit 205, reads the client identifier i 251 from the identifier storing unit 206, and combines the read client identifier i, the received semi-anonymous individual identifier C', and the received individual related information R in the stated order to generate the semi-anonymous information H'.

$$H' = i \| C' \| R \quad \text{(Expression 18)}$$

The communications unit 208 transmits the semi-anonymous information H' via the network 2 to the anonymity server device 30.

(3) Construction of Anonymity Server Device 30.

The system parameter storing unit 313 further includes a region for storing the parameter P'.

The communications unit 319 further receives the parameter P' via the network 2 from the parameter generating device 10, and writes the received parameter P' into the system parameter storing unit 313. Further, the communications unit 319 receives the client identifier i and the second characteristic parameter $JB_i$ via the network 2 from the parameter generating device 10, and the received client identifier i and corresponding second characteristic parameter $JB_i$, as a piece of server-use parameter information, to the server-use characteristic parameter list 331 that is held by the characteristic parameter list storing unit 312. Further, the communications unit 319 outputs semi-anonymous information H' received from any of the information providing devices to the data splitting unit 311.

The data splitting unit 311 further receives the semi-anonymous information H' from the communications unit 319. On receiving the semi-anonymous information H', the data splitting unit 311 splits the received semi-anonymous information H' to generate the client identifier i, the semi-anonymous individual identifier C', and the individual related information R. The data splitting unit 311 then outputs the generated client identifier i and semi-anonymous individual identifier C' to the second converting unit 314, and outputs the generated individual related information R to the combining unit 315.

The second converting unit 314 further receives the client identifier i and the semi-anonymous individual identifier C' from the data splitting unit 311. On receiving the client identifier i and the semi-anonymous individual identifier C', the second converting unit 314 extracts the piece of server-use information including the received client identifier i from the server-use parameter list 331, and extracts the second characteristic parameter $JB_i$ from the extracted piece of server-use parameter information. Further, the second converting unit 314 reads the parameter P' from the system parameter storing unit 313.

Next, using the read parameter P', the extracted second characteristic parameter $JB_i$, and the received semi-anonymous individual identifier C', the second converting unit 314 calculates an anonymous individual identifier E' by performing anonymity processing to according to the following expression:

$$E' = (C')^{JB_i} \bmod P' \quad \text{(Expression 19)}$$

Next, the second converting unit 314 outputs the generated anonymous individual identifier E' to the combining unit 315.

The combining unit 315 further receives the anonymous individual identifier E' from the second converting unit 314, and receives the individual related information R from the data splitting unit 311. On receiving the anonymous individual identifier E' and the individual related information R, the combining unit 315 combines the received anonymous individual identifier E' and individual related information R in the stated order to obtain the combination E'||R. The combining unit 315 then outputs the combination E'||R to the identifier adding unit 316.

The identifier adding unit 316 further receives the combination E'||R from the combining unit 315, and on receiving the combination E'||R, generates an anonymous individual identifier J' that uniquely identifies the received combination E'||R. Next, the identifier adding unit 316 combines the generated anonymous individual identifier J' and the received combination E'||R in the stated order to generate a piece of anonymous information F'.

$$F' = J' \| E' \| R \quad \text{(Expression 20)}$$

The identifier adding unit 316 then writes the generated anonymous information F' into the information storing unit 317.

Figure 17:
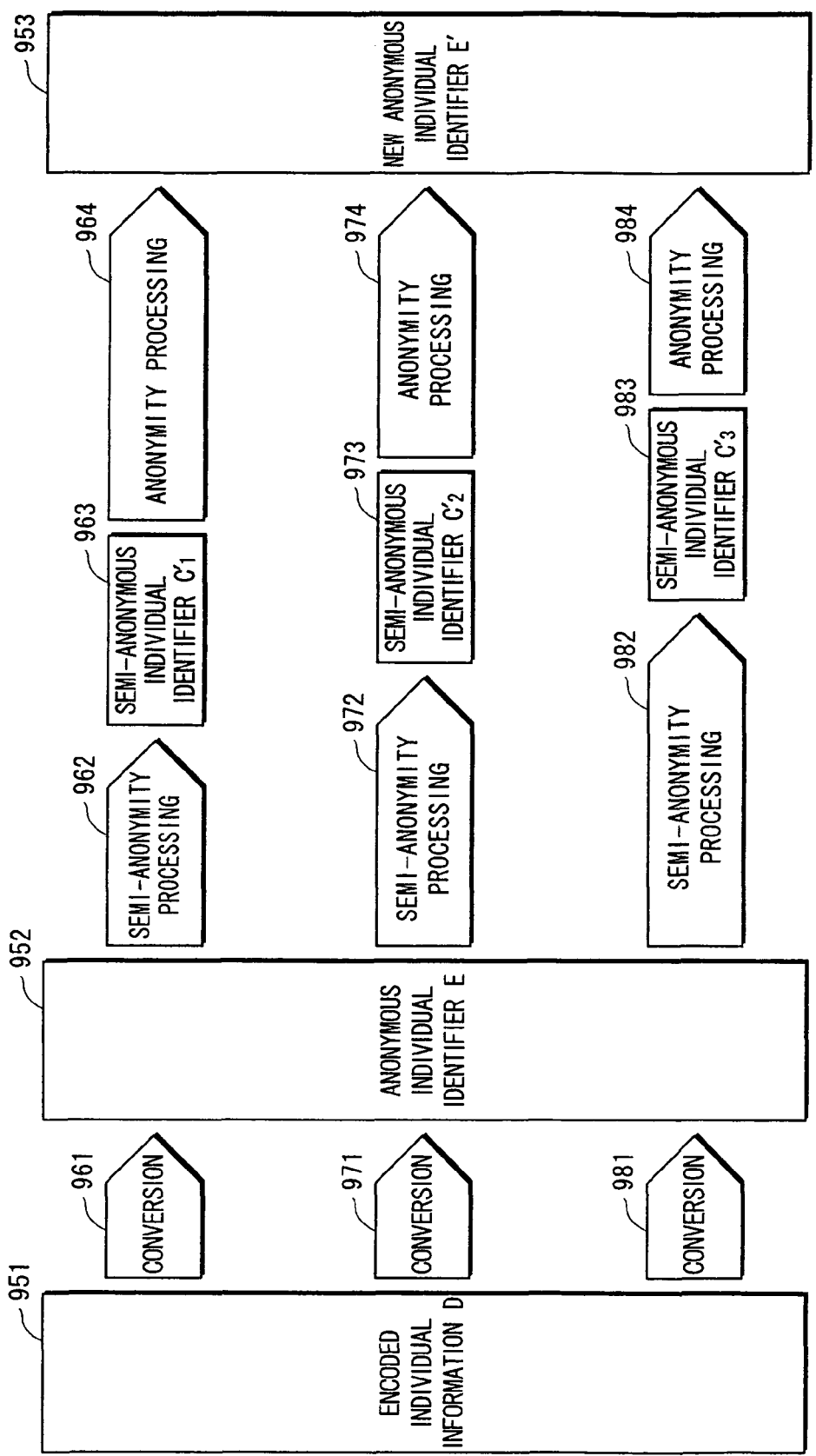
FIG. 17 shows conceptually a relationship among encoded individual information, an anonymous individual identifier, a new semi-anonymous individual identifier, and a new anonymous individual identifier in the case when conversion processing for converting from the encoded individual information to the anonymous individual identifier has been updated.

(4) Update of Conversion Processing for Converting from Encoded Individual Information to Anonymous Information The relationships among pieces of encoded individual information, anonymous individual identifiers and new anonymous individual identifiers is shown conceptually in FIG. 17.

When the conversion processing for converting from the encoded information to the anonymous individual identifier is itself to be updated, the information providing device 21 first performs conversion processing 961 to convert from the encoded individual identifier D to the anonymous individual identifier E. Using the conversion processing 961, the same result is obtained as when the semi-anonymity processing and the anonymity processing of the above embodiment are performed in the stated order.

Next, the information providing device 21 performs semi-anonymity processing 962, which is described in the embodiment, on the anonymous individual identifier E obtained in this way, and obtains a new semi-anonymous individual identifier C'1.

Next, the anonymity server device 30 performs anonymity processing 964, which is described in the above embodiment, on the semi-anonymous individual identifier C'1 to generate a new anonymous individual identifier E'.

Further, the information providing device 22 first performs the conversion processing 971 to convert from the coded individual identifier D to the anonymous individual identifier E. Next, the information providing device 22 performs semi-anonymity processing 972 on the anonymous individual identifier E that has been obtained in this way, and obtains a new semi-anonymous individual identifier C'2. Next, the anonymity server device 30 performs anonymity processing 974, which is described in the above embodiment, on the semi-anonymous individual identifier C'2 to generate a new anonymous individual identifier E'.

Moreover, the information providing device 23 first performs the conversion processing 981 to convert from the encoded individual identifier D to the anonymous individual identifier E. Next, the information providing device 23 performs semi-anonymity processing 982 on the anonymous individual identifier E that has been obtained in this way, and obtains a new semi-anonymous individual identifier C' 3. Next, the anonymity server device 30 performs anonymity processing 984, which is described in the above embodiment, on the semi-anonymous individual identifier C' 3 to generate a new semi-anonymous individual identifier E'.

(5) Operations of Conversion Processing Update in Anonymity System 1

The operations of conversion processing update in anonymity system 1 are described below.

(a) Operations of Parameter Update

Figure 18:
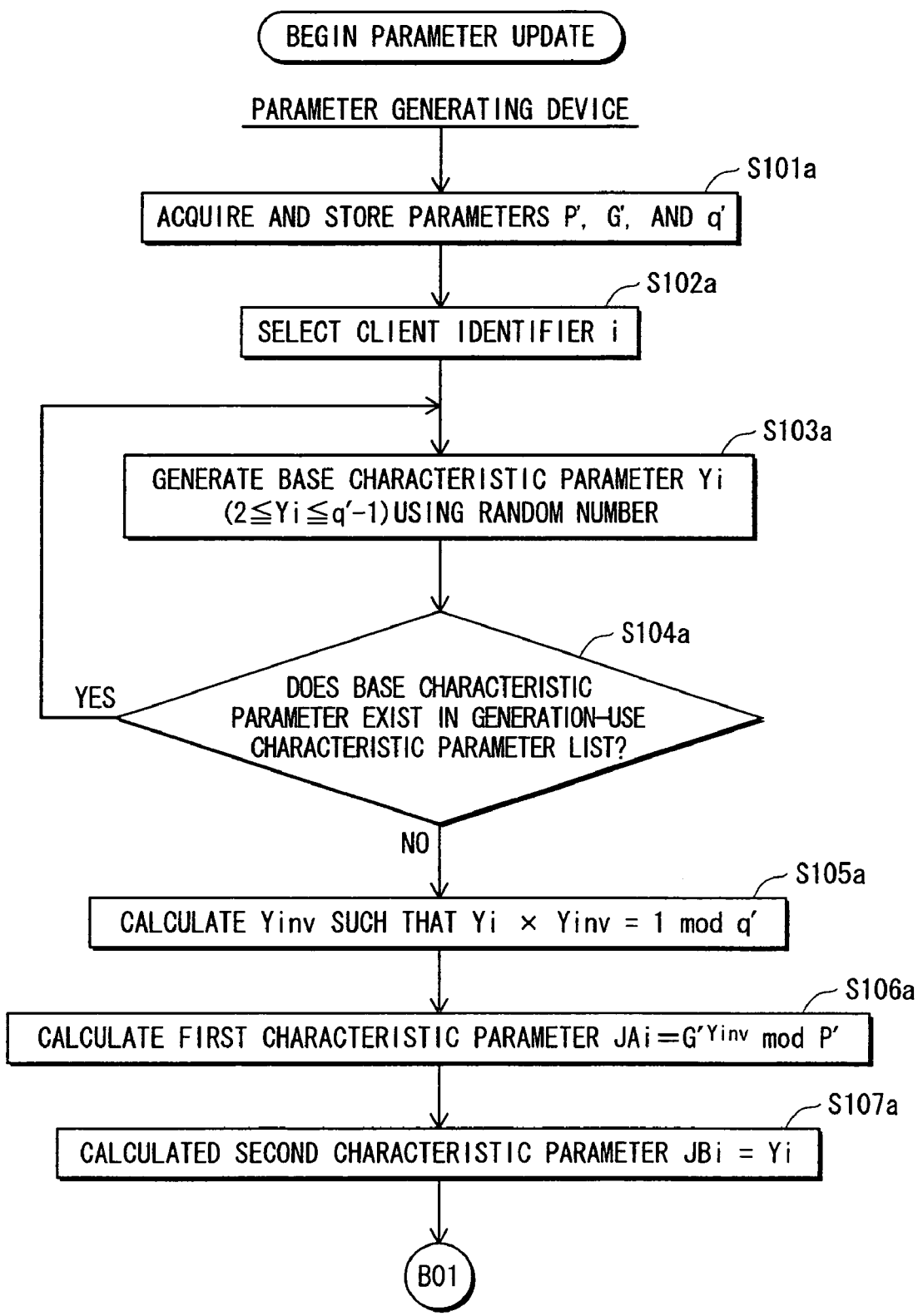
FIG. 18 is a flow-chart showing operations of parameter update in an anonymous information system 1, the flow-chart being continued in FIG. 19.
Figure 19:
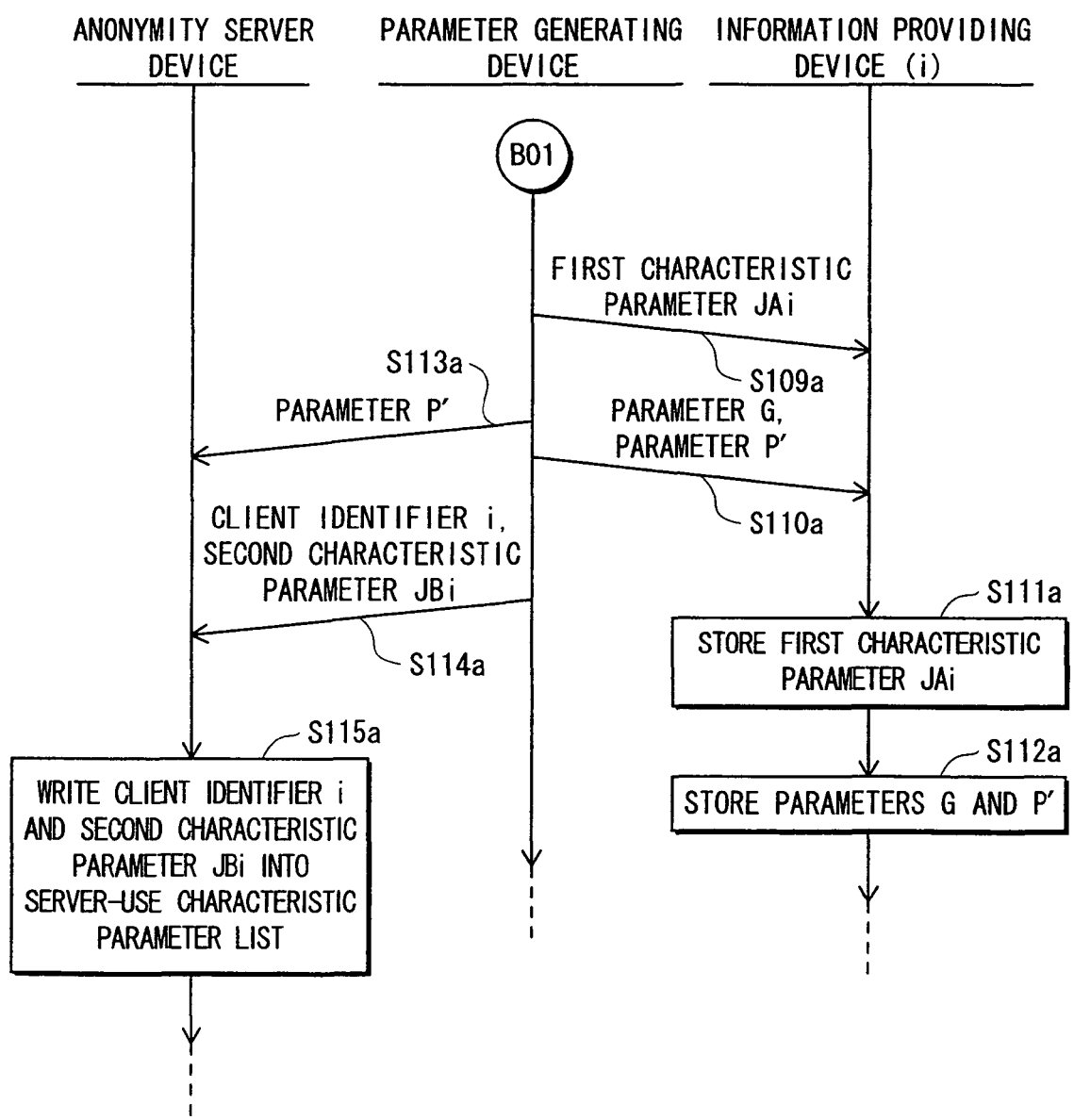
FIG. 19 is continued from FIG. 18, and is a flow-chart showing operations of parameter update in the anonymous information system 1.

The operations of parameter update in anonymous information system 1 are described with reference to the flow chart shown in FIG. 18 and FIG. 19.

The input unit 101 of the parameter generating device 10 receives, from the operator of the parameter generating device 10, an instruction indicating an update of the conversion processing and of the parameters across the whole of the anonymous information system 1, and further receives input of a new parameter P', a new parameter G' and a new parameter q', and the control unit writes the received parameter P', parameter G' and parameter q' into the information storing unit 105 (Step S101a).

Next, the control unit 104 reads all the pieces of generation-use parameter information from the generation-use characteristic parameter list 131, and selects a client identifier i from the client identifiers included in the read pieces of generation-use parameter information (Step S102a).

Next, the parameter generating unit 103 generates a random number that satisfies $2 \leq$ random number $\leq q'-1$ (Step S103a), judges whether or not the generated random number exists as a base characteristic parameter in the generation-use characteristic parameter list 131 of the information storing unit 105, and if the generated random number exists (YES in Step S104a), again generates a random number (Step S103a). If the generated random number does not exist in the generation-use characteristic parameter list 131 (NO in Step S104a), the parameter generating unit 103 sets the generated random number to be the base characteristic parameter $Y_i$, calculates $Y_{inv}$ that satisfies $Y_i \times Y_{inv} = 1$ mod q' (Step S105a), calculates the first characteristic parameter $JA_i$ using $JA_i = G'^{Y_{inv}}$ mod P' (Step S106a), and calculates the second characteristic parameter $JB_i$ using $JB_i = Y_i$ (Step S107a).

The communications unit 106 reads the parameter G and the parameter P' from the information storing unit 105, and transmits the read parameter G and the read parameter P' to the information providing devices, and transmits each first characteristic parameters $JA_i$ to the corresponding information providing device (Step S109a to Step S110a). Next, the communications unit 106 transmits the read parameter P' to the anonymity server device 30 (Step S113a), and transmits each client identifier i, and each second characteristic parameter $JB_i$ via the network 2 to the anonymity server device 30 (Step S114a).

The communications device 208 of each information providing device writes the first characteristic parameter $JA_i$ into the individual parameter storing unit 204 (Step S111a), and writes the parameter G and the parameter P' into the system parameter storing unit 203 (Step S112a).

The communications unit 319 of the anonymity server device 30 writes the parameter P' into the system parameter storing unit 313, and writes each client identifier i and each second characteristic parameter $JB_i$ into the server-use characteristic parameter list 331 (Step S115a).

(b) Operations of Semi-Anonymous Information Generation

Figure 20:
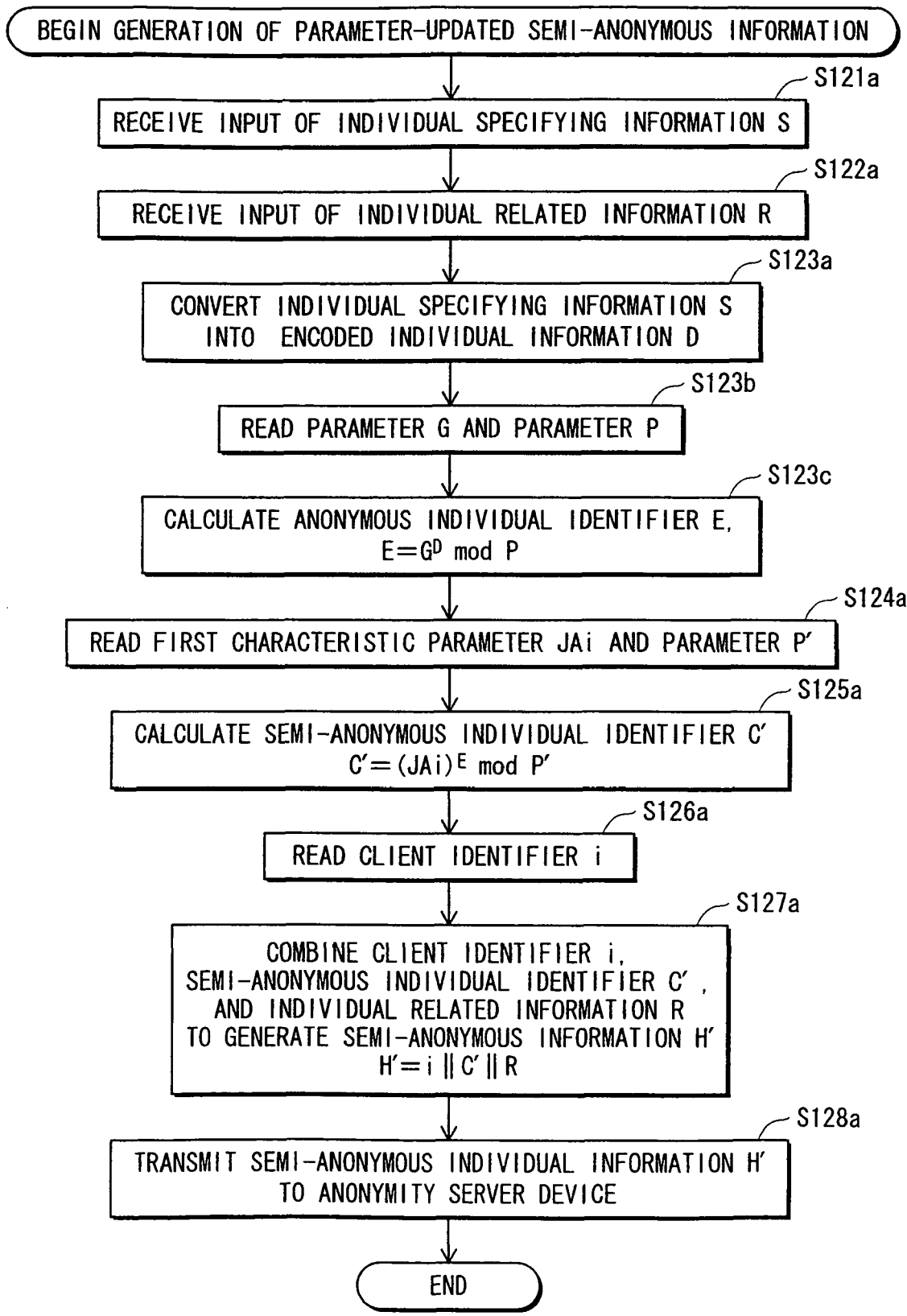
FIG. 20 a flow-chart showing operations for generating the semi-anonymous information using an information provision device 21 in the case when the parameters have been updated.

The operations for generating semi-anonymous information using the information providing device 21 are described with reference to the flowchart shown in FIG. 20.

The input unit 201 receives input consisting of the individual specifying information S and the individual related information R from the operator of the information providing device 21 (Step S121a to Step S122a).

Next, the encoder unit 202 converts the individual specifying information S into the encoded individual information D (Step S123a).

Next, the first converting unit 205 reads the parameter G, the parameter P 231, and the parameter P' from the system parameter storing unit 203 (Step S123b), and using the encoded individual information D, the parameter G, and the parameter P 231, calculates the anonymous individual identifier E according to $E = G^D$ mod P (Step S123c).

Next, the first converting unit 205 reads the parameter P' and the first characteristic parameter $JA_i$ (Step S124a), and using the calculated anonymous individual identifier E, the read parameter P', and first characteristic parameter $JA_i$ 241, generates the semi-anonymous individual identifier C' according to $C' = (JA_i)^E$ mod P' (Step S125a).

Next, the combining unit 207 reads the client identifier i 251 from the identifier storing unit 206 (Step S126a), and combines the read client identifier i, the received semi-anonymous individual identifier C', and the received individual related information R in the stated order to generate the semi-anonymous information H', such that H'=i||C'||R (Step S127a).

Next, the communications unit 208 transmits the semi-anonymous information H' via the network 2 to the anonymity server device 30 (Step S128a).

(c) Operations of Anonymous Information Generation

Figure 21:
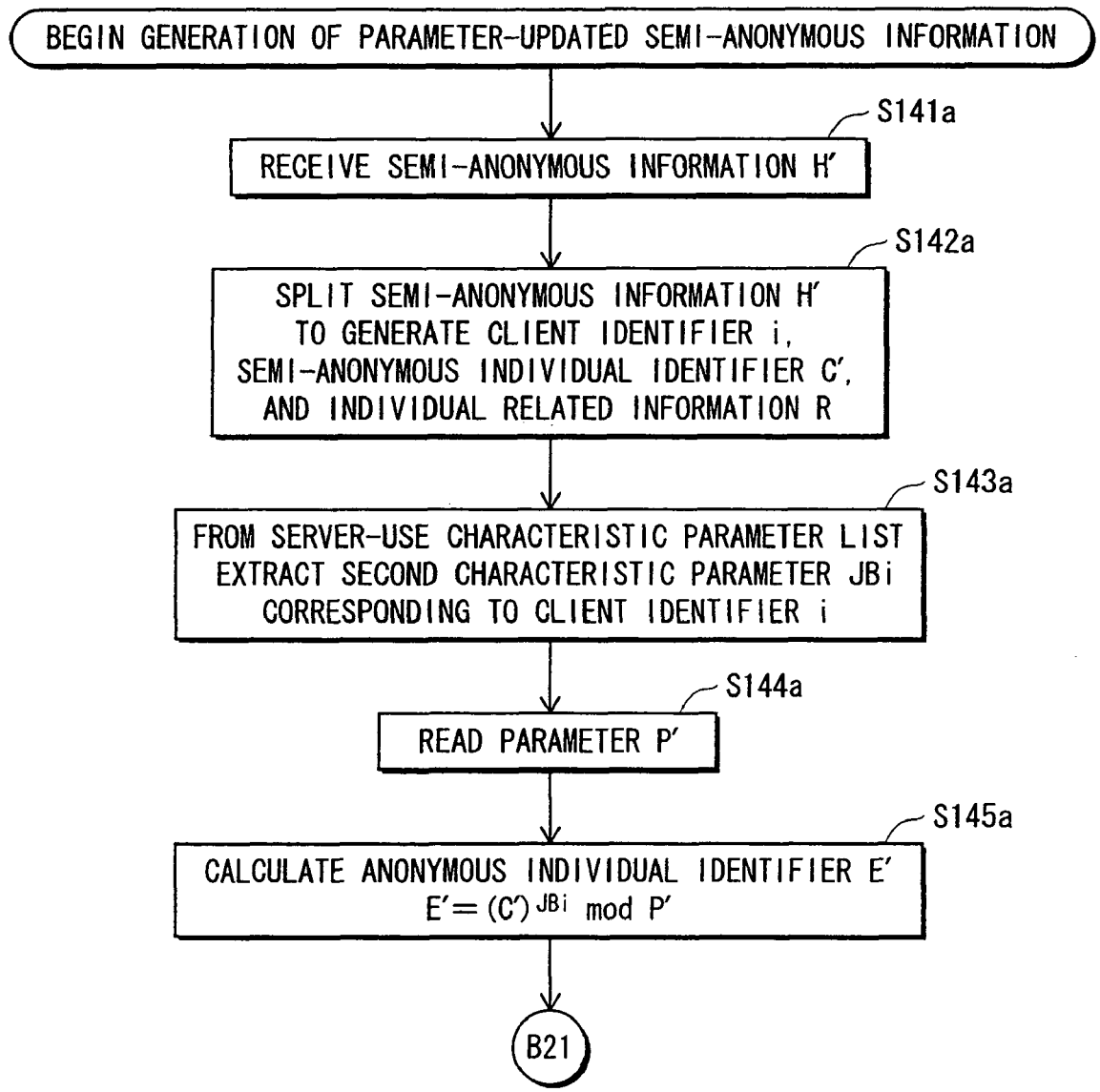
FIG. 21 is a flow-chart showing operations for generating the anonymous information using the anonymity server device 30 in the case when the parameters have been updated, the flow-chart being continued in FIG. 22.
Figure 22:
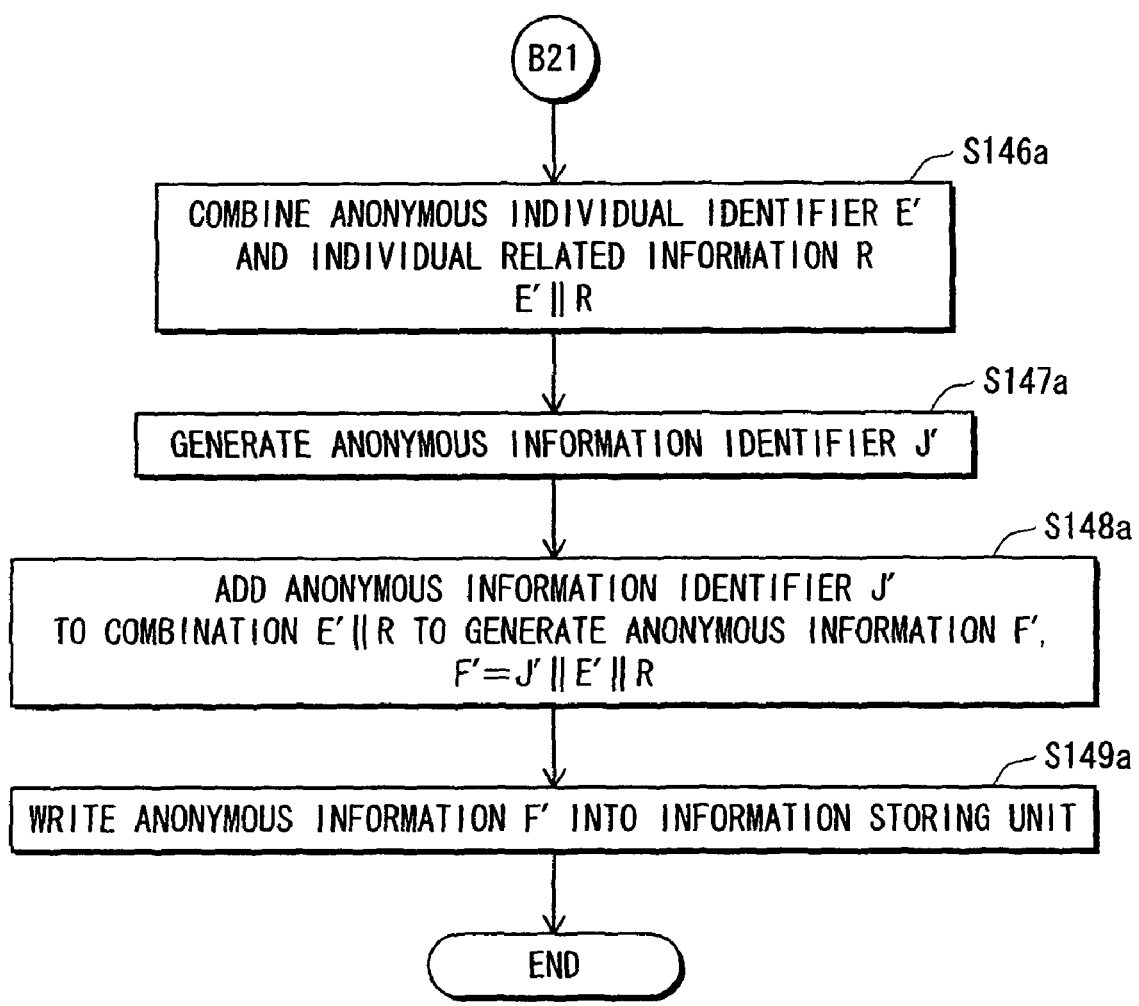
FIG. 22 is continued from FIG. 21, and is a flow-chart showing operations for generating the anonymous information using the anonymity server device 30 in the case when the parameters have been updated.

Here, the operations of anonymous information generation using the anonymity server device 30 are described with reference to the flow-chart shown in FIG. 21 and FIG. 22.

The communications unit 319 receives the semi-anonymous information H' from the information providing device 21 (Step S141a).

Next, the data splitting unit 311 splits the received semi-anonymous information H' and generates the client identifier i, the semi-anonymous individual identifier C' and the individual related information R (Step S142a).

The second converting unit 314 extracts the piece of server-use parameter information that includes the received client identifier i from the server-use characteristic parameter list 331, and extracts the second characteristic parameter $JB_i$ from the extracted piece of server-use parameter information (Step S143a). Further, the second converting unit 314 reads the parameter P' from the system parameter storing unit 313 (Step S144a).

Next, using the read parameter P', the extracted second characteristic parameter $JB_i$, and the received semi-anonymous information identifier C', the second converting unit calculates the anonymous individual information identifier $E'=(C')^{\wedge}JB_i \bmod P'$ (Step S145a).

Next, the combining unit 315, combines the anonymous individual information identifier E' and the individual related information R in the stated order (Step S146a), the identifier adding unit 316 generates an anonymous individual identifier J' (Step S147a), and combines the anonymous individual identifier J' and the received combination E'||R in the stated order to generate the anonymous information F'=J'||E'||R (Step S148a). The identifier adding unit 316 then writes the generated anonymous information F' into the information storing unit 317 (Step S149a).

2. Modifications (1)

An anonymous information system 1a (not shown in the drawings) is described as a modified example of the anonymous information system 1.

The anonymous information system 1a is constructed from a parameter generating device 10a, information providing devices 21a, 22a, 23a . . . , an anonymity server device 30a, and information searching devices 41, 42 . . . . The parameter generating device 10a, the information providing devices 21a, 22a, 23a . . . , the anonymity server device 30a, and the information searching devices 41, 42 . . . are interconnected via a network 2a.

The parameter generating device 10a, the information providing devices 21a, 22a, 23a, . . . and the anonymity server 30a have constructions that resemble the parameter generating device 10, the information providing devices 21, 22, 23, . . . and the anonymity server 30 respectively, and the information searching devices 41, 42, . . . of the anonymous information system 1a have constructions that are identical to the information searching devices 41, 42, . . . respectively.

The description below is focused on aspects of the anonymous information system 1a that differ from the anonymous information system 1.

2.1 Construction of Parameter Generating Device 10a

The parameter generating device 10a (not shown in the drawings) is constructed from an input unit 101a, a display unit 102a, a parameter generating unit 103a, a control unit 104a, an information storing unit 105a, and a communications unit 106a.

The input unit 101a, the display unit 102a, the parameter generating unit 103a, the control unit 104a, the information storing unit 105a, and the communications unit 106a are identical in construction to the input unit 101, the display unit 102, the parameter generating unit 103, the control unit 104, the information storing unit 105, and the communications unit 106 respectively.

Here, the description is focused on aspects that differ from the parameter generating device 10.

The input unit 101 acquires, from an exterior source, a system characteristic modulus P, which is characteristic to the anonymous information system 1a. Here, the system characteristic modulus P is an integer 192 bits in length. Further, the input unit 101a acquires the coefficients a and b of an elliptic curve $E_0$, where, $E_0$ is expressed according to:

$$y^2 = x^3 + ax + b \pmod{P}$$

Further, the input unit 101a acquires a basepoint G and an order q which are characteristic to the anonymous information system 1a. Here the basepoint G is a point on the elliptic curve $E_0$, and the order of G is q. Further, G is the base parameter in the conversion process in which the semi-anonymity processing and the anonymity processing are performed consecutively.

The input unit 101a writes the acquired system characteristic modulus P, coefficient a, coefficient b, basepoint G, and order q into the information storing unit 105a.

The communications unit 106a discloses the system characteristic modulus P, the coefficient a, and the coefficient b, which are stored in the information storing unit 105a as system parameters characteristic to the anonymous information system 1a. In other words, the communications unit 106a transmits the system characteristic modulus P, the coefficient a, and the coefficient b via the network 2a to the information providing devices 21a, 22a, 23a, . . . , and to the anonymity server device 30a.

The basepoint G and order q stored in the information storing device 105a are concealed as a secret keys characteristic to the system.

The parameter generating unit 103a randomly selects a base characteristic parameter X, which is an integer, in the range $2 \leq X \leq q-1$, and calculates $X_{inv}$ to satisfy:

$$X_i \times X_{inv} = 1 \bmod q \quad \text{(Expression 21)}.$$

Where "x" indicates a multiplication in GF(q).

Next, the parameter generating unit 103a calculates the first characteristic parameter $KA_i$ using:

$$KA_i = X_{inv} * G (\text{over } E_0) \quad \text{(Expression 22)}.$$

Expression 22 indicates a repetitive addition.

Here, "*" is an operator indicating a multiplication on elliptic curve $E_0$, and the first characteristic parameter $KA_i$ is a point on the elliptic curve $E_0$.

Next, the parameter generating unit 103 calculates the second characteristic parameter second $KB_i$ using:

$$KB_i = X_i \quad \text{(Expression 23)}.$$

Note that since $$KB_i * KA_i (\text{over } E_0) = X_i \times X_{inv} * G (\text{over } E_0)$$
$$= G (\text{over } E_0)$$

the first characteristic parameter and the second characteristic parameter are complementary with respect to the basepoint G that is the base parameter.

The communications unit 106a transmits, via the network 2a, the first characteristic parameter $KA_i$ to the information providing device and the second characteristic parameter $KB_i$ to the anonymity server 30a.

2.2 Construction of Information Providing Device 21a

The information providing device 21a (not shown in the drawings) is, in the same way as the information providing device 21, constructed from an input unit 201a, an encoder unit 202a, a system parameter storing unit 203a, a characteristic parameter storing unit 204a, a first converting unit 205a, an identifier storing unit 206a, a combining unit 207a, a communications unit 208a, and an update unit 209a.

The input unit 201a, the encoder unit 202a, the system parameter storing unit 203a, the characteristic parameter storing unit 204a, the first converting unit 205a, the identifier storing unit 206a, the combining unit 207a, the communications unit 208a, and the update unit 209a have the same constructions as the input unit 201a, the encoder unit 202, the system parameter storing unit 203, the characteristic parameter storing unit 204, the first converting unit 205, the identifier storing unit 206, the combining unit 207, the communications unit 208, and the update unit 209 of the information device 21 respectively.

Here, the description is focused on aspects that differ from the information providing device 21.

The communications device 106a receives the system characteristic modulus P, the coefficient a, and the coefficient b via the network 2a from the parameter generating device 10a, and writes the received system characteristic modulus P, coefficient a, and coefficient b into the system parameter storing unit 203a.

Further, the communications unit 106a receives the first characteristic parameter $KA_i$ from the parameter generating device 10a, and writes the received first characteristic parameter $KA_i$ into the characteristic parameter storing unit 204a.

Using the received encoded individual information D, the read parameter P, coefficient a, coefficient b and first characteristic parameter $KA_i$, the first converting unit 205 performs semi-anonymity processing according to the following expression to generate the semi-anonymous individual identifier C.

$$C = D * KA_i (\text{over } E_0) \quad \text{(Expression 24)}$$

Expression 4 indicates a repetitive addition.

Here, the semi-anonymous individual identifier C is a point on the elliptic curve $E_0$.

The combining unit 207a combines the read client identifier i, the x coordinate Cx and the y coordinate Cy of the received semi-anonymous individual identifier C, and the received individual related information R in the stated order to generate the semi-anonymous information H.

$$H = i \| Cx \| Cy \| R \quad \text{(Expression 25)}$$

The communications unit 208a transmits the semi-anonymous information H via the network 2a to the anonymity server 30a.

2.3 Anonymity Server Device 30a

The anonymity server device 30a (not shown in the drawings) is, in the same way as the anonymity server device 30, constructed from a data splitting unit 311a, a characteristic parameter list storing unit 312a, a system parameter storing unit 313a, a second converting unit 314a, a combining unit 315a, an identifier adding unit 316a, an information storing unit 317a, a search unit 318a, a communications unit 319a, and an update unit 320a.

The data splitting unit 311a, the characteristic parameter list storing unit 312a, the system parameter storing unit 313a, the second converting unit 314a, the combining unit 315a, the identifier adding unit 316a, the information storing unit 317a, the search unit 318a, the communications unit 319a, and the update unit 320a have the same constructions as the data splitting unit 311, the characteristic parameter list storing unit 312, the system parameter storing unit 313, the second converting unit 314, the combining unit 315, and the information storing unit 317, the search unit 318, the communications unit 319, and the update unit 320 respectively of the anonymity server device 30.

The communications unit 319a receives the system characteristic modulus P, the coefficient a, and the coefficient b via the network 2a from the parameter generating device 10a, and writes the received system characteristic modulus P, coefficient a and coefficient b into the system parameter storing unit 313a.

Further, the communications unit 319a receives the second characteristic parameter $KB_i$ and writes the received the second characteristic parameter $KB_i$ into the characteristic parameter list storing unit 312a.

Using the system characteristic modulus P, the coefficient a, the coefficient b, the second characteristic parameter $KB_i$, and the semi-anonymous individual identifier C, the second converting unit 314a calculates the anonymous individual identifier E by performing anonymous processing according to the following expression:

$$E = KB_i * C (\text{over } E_0) \quad \text{(Expression 26)}$$

In Expression 26, C is added to itself $KB_i - 1$ times. In other words, Expression 26 indicates a repetitive addition.

Here, the anonymous individual identifier E is a point on the elliptic curve $E_0$.

The combining unit 315a combines the x-coordinate Ex and the y coordinate Ey of the anonymous individual identifier E, and the individual related information R in the stated order to obtain the combination $Ex \| Ey \| R$.

The identifier adding unit 316a combines the anonymous information identifier J and the combination $Ex \| Ey \| R$ in the stated order to generate anonymous information F.

$$F = J \| Ex \| Ey \| R \quad \text{(Expression 27)}$$

Next the identifier adding unit 316a writes the generated anonymous information F into the information storing unit 317a.

2.4 Supplementary Description

The semi-anonymous individual identifier calculated by the information providing device 21a is $$C = D * KA_i (\text{over } E_0)$$
$$= (D \times X_{inv}) * G (\text{over } E_0)$$

and the anonymous individual identifier E calculated by the anonymity server device 30a is $$E = KB_i * C (\text{over } E_0)$$
$$= (D \times X \times X_{inv}) * G (\text{over } E_0)$$
$$= D * G (\text{over } E_0)$$

Thus, when the semi-anonymity processing $D * KA_i$ (over $E_0$) is performed on the encoded individual information D, and the anonymity processing $KA_i*C$ (over $E_0$) is performed on the result of the semi-anonymity processing, the result will always be $D*G$ (over $E_0$)

3. Modifications (2)

Anonymous information system $1b$ (not shown in the drawings) is described as a modified example of anonymous information system $1$.

The anonymous information system $1b$ is constructed from a parameter generating device $10b$, information providing devices $21b$, $22b$, $23b$ . . . , an anonymity server device $30b$, and information searching devices $41$, $42$ . . . . The parameter generating device $10b$, the information providing devices $21b$, $22b$, $23b$ . . . , the anonymity server device $30b$, and the information searching devices $41$, $42$ . . . are interconnected via a network $2b$.

The parameter generating device $10b$, the information providing devices $21b$, $22b$, $23b$, . . . and the anonymity server $30b$ have constructions that resemble the parameter generating device $10$, the information providing devices $21$, $22$, $23$, . . . and the anonymity server $30$ respectively, and the information searching devices $41$, $42$, . . . of the anonymous information system $1b$ have constructions that are identical to the information searching devices $41$, $42$, . . . respectively.

The description below is focused on aspects of the anonymous information system $1b$ that differ from the anonymous information system $1$.

3.1 Construction of Parameter Generating Device $10b$

The parameter generating device $10a$ (not shown in the drawings) is constructed from an input unit $101b$, a display unit $102b$, a parameter generating unit $103b$, a control unit $104b$, an information storing unit $105b$, and a communications unit $106b$.

The input unit $101b$, the display unit $102b$, the parameter generating unit $103b$, the control unit $104b$, the information storing unit $105b$, and the communications unit $106b$ are identical in construction to the input unit $101$, the display unit $102$, the parameter generating unit $103$, the control unit $104$, the information storing unit $105$, and the communications unit $106$ respectively.

Here, the description is focused on aspects that differ from the parameter generating device $10$.

The input unit $101$ acquires a system characteristic modulus N, which is characteristic to the anonymous information system $1b$, from an exterior source. Here, the system characteristic modulus N is an integer 1024 bits in length, and satisfies N=P×Q where each of P and Q is prime. Further, the input unit $101b$ acquires a system characteristic secret value X, which is characteristic to the anonymous information system $1b$, from an exterior source. The system characteristic secret parameter X is an integer 1024 bits in length, and satisfies $$2 \leq X \leq \lambda(N)-1 \quad \text{(Expression 28)}$$

where $\lambda(N)$ and X are relatively prime, $\lambda(N)$ is a Carmichael function, and when each of P and Q is prime, $\lambda(N)$ LCM (P−1, Q−1). Here, LCM (A, B) is the least common multiple of A and B.

Here, N is disclosed as a public system parameter, and X, P, Q, and $\lambda(N)$ are not disclosed, but are concealed as secret values characteristic to the system.

The input unit $101b$ writes the system characteristic modulus N, the system characteristic secret value X, and $\lambda(N)$ into the information storing unit $105b$.

The reception unit $101b$ discloses the system characteristic modulus N stored in the information storage unit $105b$ as a system parameter characteristic to the anonymous information system $1b$. In other words, the communications unit $106b$ transmits the system characteristic modulus N via the network $2b$ to the information providing devices $21b$, $22b$, $23b$, . . . , and to the anonymity server device $30b$.

The system characteristic secret values X and $\lambda(N)$ are concealed as secret keys characteristic to the system.

The parameter generating unit $103b$ randomly selects the second characteristic parameter $KB_i$ such that:

$$2 \leq KB_i \leq \lambda(N)-1 \quad \text{(Expression 29)}$$

is satisfied and $\lambda(N)$ and $KB_i$ are relatively prime.

Further, the parameter generating unit calculates a $KA_i$ to satisfy:

$$KA_i \times KB_i = X \bmod \lambda(N) \quad \text{(Expression 30)}.$$

Here X is the base parameter in the conversion process in which the semi-anonymity processing and the anonymity processing are performed consecutively. Further, according to Expression 30, the first characteristic parameter and the second characteristic parameter are complementary with respect to the basic parameter that is X.

The communications unit $106b$ transmits, via the network $2b$, the first characteristic parameter $KA_i$ to the information providing device, and the second characteristic parameter $KB_i$ to the anonymity server $30b$.

3.2 Construction of Information Providing Device $21b$

The information providing device $21b$ (not shown in the drawings) is, in the same way as the information providing device $21$, constructed from an input unit $201b$, an encoder unit $202b$, a system parameter storing unit $203b$, a characteristic parameter storing unit $204b$, a first converting unit $205b$, an identifier storing unit $206b$, a combining unit $207b$, a communications unit $208b$, and an update unit $209b$.

The input unit $201b$, the encoder unit $202b$, the system parameter storing unit $203b$, the characteristic parameter storing unit $204b$, the first converting unit $205b$, the identifier storing unit $206b$, the combining unit $207b$, the communications unit $208b$, and the update unit $209b$ have the same constructions as the input unit $201$, the encoder unit $202$, the system parameter storing unit $203$, the characteristic parameter storing unit $204$, the first converting unit $205$, the identifier storing unit $206$, the combining unit $207$, the communications unit $208$, and the update unit $209$ respectively of the information device $21$.

Here, the description is focused on aspects that differ from the information providing device $21$.

The communications device $106b$ receives the system characteristic modulus N, via the network $2b$ from the parameter generating device $10b$, and writes the received system characteristic modulus N into the system parameter storing unit $203b$.

Further, the communications unit $106b$ receives the first characteristic parameter $Ka_i$ from the parameter generating device $10b$, and writes the received first characteristic parameter $KA_i$ into the characteristic parameter storing unit $204b$.

Using the system characteristic modulus N, the encoded individual information D, and the first characteristic parameter $KA_i$, the first converting unit $205b$ generates the semi-anonymous individual identifier C by performing semi-anonymity processing according to the following expression.

$$C = D\char`\^ KA_i \bmod N \quad \text{(Expression 31)}$$

In Expression 31, D is multiplied by itself D−1 times. In short, Expression 31 indicates a repetitive multiplication.

The combining unit 207b combines the read client identifier i, the received semi-anonymous individual identifier C, and the received individual related information R in the stated order to generate the semi-anonymous information H.

$$H=i\|C\|R \quad \text{(Expression 32)}$$

The communications unit 208b transmits the semi-anonymous information H via the network 2b to the anonymity server 30b.

2.3 Anonymity Server Device 30b

The anonymity server device 30b (not shown in the drawings) is, in the same way as the anonymity server device 30, constructed from a data splitting unit 311b, a characteristic parameter list storing unit 312b, a system parameter storing unit 313b, a second converting unit 314b, a combining unit 315b, an identifier adding unit 316b, an information storing unit 317b, a search unit 318b, a communications unit 319b, and an update unit 320b.

The data splitting unit 311b, the characteristic parameter list storing unit 312b, the system parameter storing unit 313b, the second converting unit 314b, the combining unit 315b, the identifier adding unit 316b, the information storing unit 317b, the search unit 318b, the communications unit 319b, and the update unit 320b have the same constructions as the data splitting unit 311, the characteristic parameter list storing unit 312, the system parameter storing unit 313, the second converting unit 314, the combining unit 315, and the information storing unit 317, the search unit 318, the communications unit 319, and the update unit 320 of the anonymity server device 30 respectively.

The communications unit 319b receives the system characteristic modulus N via the network 2b from the parameter generating device 10b, and writes the received system characteristic modulus N into the system parameter storing unit 313b.

Further, the communications unit 319b receives the second characteristic parameter $KB_i$, and writes the received the second characteristic parameter $KB_i$ into the characteristic parameter list storing unit 331b.

Using the system characteristic modulus N, the second characteristic parameter $KB_i$, and the semi-anonymous individual identifier C, the second converting unit 314a calculates the anonymous individual identifier E by performing anonymous processing according to the following expression:

$$E=C\char`\^KB_i \bmod N \quad \text{(Expression 33)}$$

In Expression 33, C is multiplied by itself $KB_i-1$ times. In other words, Expression 33 indicates a repetitive multiplication.

The combining unit 315b combines the anonymous individual identifier E and the individual related information R in the stated order to obtain the combination E∥R.

The identifier adding unit 316b combines the anonymous information identifier J and the combination E∥R in the stated order to generate the anonymous information F.

$$F=J\|E\|R \quad \text{(Expression 34)}$$

Next the identifier adding unit 316b writes the generated anonymous information F into the information storing unit 317a.

3.4 Supplementary Description

The semi-anonymous individual identifier calculated by the information providing device 21b is $$C=D\char`\^KA_i \bmod N$$

and the anonymous individual identifier E calculated by the anonymity server device 30b is $$\begin{aligned} E &= C \char`\^ KB_i \bmod N \quad \text{(Expression 35)} \\ &= D \char`\^ (KA_i \times KB_i) \bmod N \\ &= D \char`\^ X \bmod N \end{aligned}$$

Thus, when the semi-anonymity processing $D\char`\^KA_i \bmod N$ is performed on the encoded individual information D, and the anonymity processing $C\char`\^KA_i \bmod N$ is performed on the result of the semi-anonymity processing, the result will always be $D\char`\^X \bmod N$.

4. Modifications (3)

An anonymous information system 1c (not shown in the drawings) is described as a modified example of anonymous information system 1.

The anonymous information system 1c is constructed from a parameter generating device 10c, information providing devices 21c, 22c, 23c . . . , an anonymity server device 30c, and information searching devices 41, 42 . . . . The parameter generating device 10c, the information providing devices 21c, 22c, 23c . . . , the anonymity server device 30a, and the information searching devices 41, 42 . . . are interconnected via a network 2c.

The parameter generating device 10c, the information providing devices 21c, 22c, 23c, . . . and the anonymity server 30c have constructions that resemble the parameter generating device 10, the information providing devices 21, 22, 23, . . . and the anonymity server 30 respectively, and the information searching devices 41, 42, . . . of the anonymous information system 1c have constructions that are identical to the information searching devices 41, 42, . . . respectively.

The description below is focused on aspects of the anonymous information system 1c that differ from the anonymous information system

4.1 Construction of Parameter Generating Device 10c

The parameter generating device 10c is constructed from an input unit 101c, a display unit 102c, a parameter generating unit 103c, a control unit 104c, an information storing unit 105c, and a communications unit 106c (and is not shown in the drawings).

The input unit 101c, the display unit 102c, the parameter generating unit 103c, the control unit 104c, the information storing unit 105c, and the communications unit 106c are identical in construction to the input unit 101, the display unit 102, the parameter generating unit 103, the control unit 104, the information storing unit 105, and the communications unit 106 respectively.

Here, the description is focused on aspects that differ from the parameter generating device 10.

On receiving a parameter generation instruction, the parameter generating unit 103c, generates, for one of the information providing devices, a client identifier i that uniquely identifies said information providing device.

The input unit 101c acquires an overall number of repetitions $k_i$ of an encryption algorithm AES (Advanced Encryption Algorithm) for the information providing device, and writes the overall number of repetitions into the information storing device 105c.

Here, the overall number of repetitions $k_i$ is the base parameter of the conversion processing in which the semi-anonymity processing and the anonymity processing are performed consecutively.

The parameter generating unit 103 selects a first number of repetitions $n_i$ randomly from values that satisfy $$1 \leq n_i \leq k_i - 1 \quad \text{(Expression 36)}$$

Furthermore, the parameter generating unit 103c calculates a second number of repetitions according to the following expression.

$$m_i = k_i - n_i \quad \text{(Expression 36)}$$

The communications unit 106c transmits, via the network 2c, the first number of repetitions $n_i$ to the information providing device and the second number of repetitions to the anonymity server 30.

Note that the since $m_i + n_i = k_i$ the first number of repetitions and the second number of repetitions are complementary with respect to the total number of repetitions $k_i$.

4.2 Construction of Information Providing Device 21c

The information providing device 21c (not shown in the drawings) is, in the same way as the information providing device 21, constructed from an input unit 201c, an encoder unit 202c, a system parameter storing unit 203c, a characteristic parameter storing unit 204c, a first converting unit 205c, an identifier storing unit 206c, a combining unit 207c, a communications unit 208c, and an update unit 209c.

The input unit 201c, the encoder unit 202c, the system parameter storing unit 203c, the characteristic parameter storing unit 204c, the first converting unit 205c, the identifier storing unit 206c, the combining unit 207c, the communications unit 208c, and the update unit 209c have the same constructions as the input unit 201, the encoder unit 202, the system parameter storing unit 203, the characteristic parameter storing unit 204, the first converting unit 205, the identifier storing unit 206, the combining unit 207, the communications unit 208, and the update unit 209 respectively of the information device 21.

Here, the description is focused on aspects that differ from the information providing device 21.

The communications unit 208 receives the first number of repetitions $n_i$ from the parameter generating unit 10c, and writes the received first number of repetitions $n_i$ into the characteristic parameter storing unit 204c.

The first converting unit 205c holds the AES encryption algorithm, and reads the first number of repetitions $n_i$ from the characteristic parameter storing unit 204.

Next, using a designated key $KEY_1$, the first converting unit 205 performs the encryption algorithm AES on the encoded personal information received from the encoder unit 202c to generate first encrypted individual information $C_1$.

Next, using a designated key $KEY_2$, the first converting unit 205c performs the encryption algorithm AES on the generated first encrypted individual information to generate second encrypted individual information $C_2$.

As shown below, the first converting unit 205 then repeats the encryption algorithm AES the number of times indicated by the first number of repetitions $n_i$ to generate the $n^{th}$ encrypted individual information $C_n$. The $n^{th}$ encrypted individual information generated in this way is the semi-anonymous individual identifier C.

$C_1 = \text{AES}(KEY_1, D)$
$C_2 = \text{AES}(KEY_2, C_1)$
$C_3 = \text{AES}(KEY_3, C_2)$
$C_4 = \text{AES}(KEY_4, C_3)$
$C_5 = \text{AES}(KEY_5, C_4)$
...
$C_{n-1} = \text{AES}(KEY_{n-1}, C_{n-2})$
$C = C_n = \text{AES}(KEY_n, C_{n-1})$ Here AES (A, B) indicates performing encryption algorithm AES on plain text B using an encryption key A to generate a cryptogram.

The combining unit 207c the combining unit 207 combines the read client identifier i, the received semi-anonymous individual identifier C, and the received individual related information R in the stated order to generate the semi-anonymous information H.

$$H = i \| C \| R \quad \text{(Expression 38)}$$

The communications unit 208c transmits the semi-anonymous information H via the network 2 to the anonymity server device 30c 4.3 Anonymity Server Device 30c The anonymity server device 30c (not shown in the drawings) is, in the same way as the anonymity server device 30, constructed from a data splitting unit 311c, a characteristic parameter list storing unit 312c, a second converting unit 314c, a combining unit 315c, an identifier adding unit 316c, an information storing unit 317c, a search unit 318c, a communications unit 319c, and an update unit 320c.

The data splitting unit 311c, the characteristic parameter list storing unit 312c, the second converting unit 314c, the combining unit 315c, the identifier adding unit 316c, the information storing unit 317c, the search unit 318c, the communications unit 319c, and the update unit 320c have the same constructions as the data splitting unit 311, the characteristic parameter list storing unit 312, the second converting unit 314, the combining unit 315, and the information storing unit 317, the search unit 318, the communications unit 319, and the update unit 320 respectively of the anonymity server device 30.

The communications unit 319c receives second number of repetitions $m_i$ and the client identifier i via the network 2c from the parameter generating device 10c, associates the second number of repetitions $m_i$ and the client identifier i in a one-to-one correspondence, and writes the associated second number of repetitions $m_i$ and the client identifier i into the characteristic parameter list storing unit 312c.

The second converting unit 314c holds the encryption algorithm AES, and reads the second number of repetitions $m_i$ from the characteristic parameter list storing unit 312c.

Further, the communications unit 319b receives the second characteristic parameter $KB_i$, and writes the received the second characteristic parameter $KB_i$ into the characteristic parameter list storing unit 312b.

Next, using the designated encryption key $KEY_{n+1}$, the second converting unit 314c performs encryption algorithm AES on the semi-anonymous individual identifier C received from the data splitting unit 311c to generate the $(n+1)^{th}$ encrypted individual information $C_{n+1}$.

Next, the second converting unit 314c performs encryption algorithm AES on the generated $(n+1)^{th}$ encrypted individual information $C_{n+1}$ using the designated encryption key $KEY_{n+2}$ to generate the $(n+2)^{th}$ encrypted individual information $C_{n+2}$.

As shown below, the second converting unit 314c then repeats the encryption algorithm the number of times indicated by the second number of repetitions $m_i$ to generate the $(n+m)^{th}$ encrypted individual information $C_{n+m}$. The $(n+m)^{th}$ encrypted individual information generated in this way is anonymous individual identifier E.

$C_{n+1}$=AES (KEY$_{n+1}$, C)
$C_{n+2}$=AES (KEY$_{n+2}$, $C_{n+1}$)
$C_{n+3}$=AES (KEY$_{n+3}$, $C_{n+2}$)
$C_{n+4}$=AES (KEY$_{n+4}$, $C_{n+3}$)
$C_{n+5}$=AES (KEY$_{n+5}$, $C_{n+4}$)
...
$C_{n+m-1}$=AES (KEY$_{n+m-1}$, $C_{n+m-2}$)
E=$C_{n+m}$=AES (KEY$_{n+m}$, $C_{n+m-1}$)

Next, the combining unit 316c combines the anonymous information identifier J and the combination E∥R in the stated order to generate the anonymous information F.

$$F=J\|E\|R \quad \text{(Expression 39)}$$

Next the identifier adding unit 326c writes the generated anonymous information F into the information storing unit 317c.

4.4 Operations of Anonymous Information System 1c

The operations of the anonymous information system 1c are described below.

(1) Operations of Parameter Generating Device 10c

Figure 23:
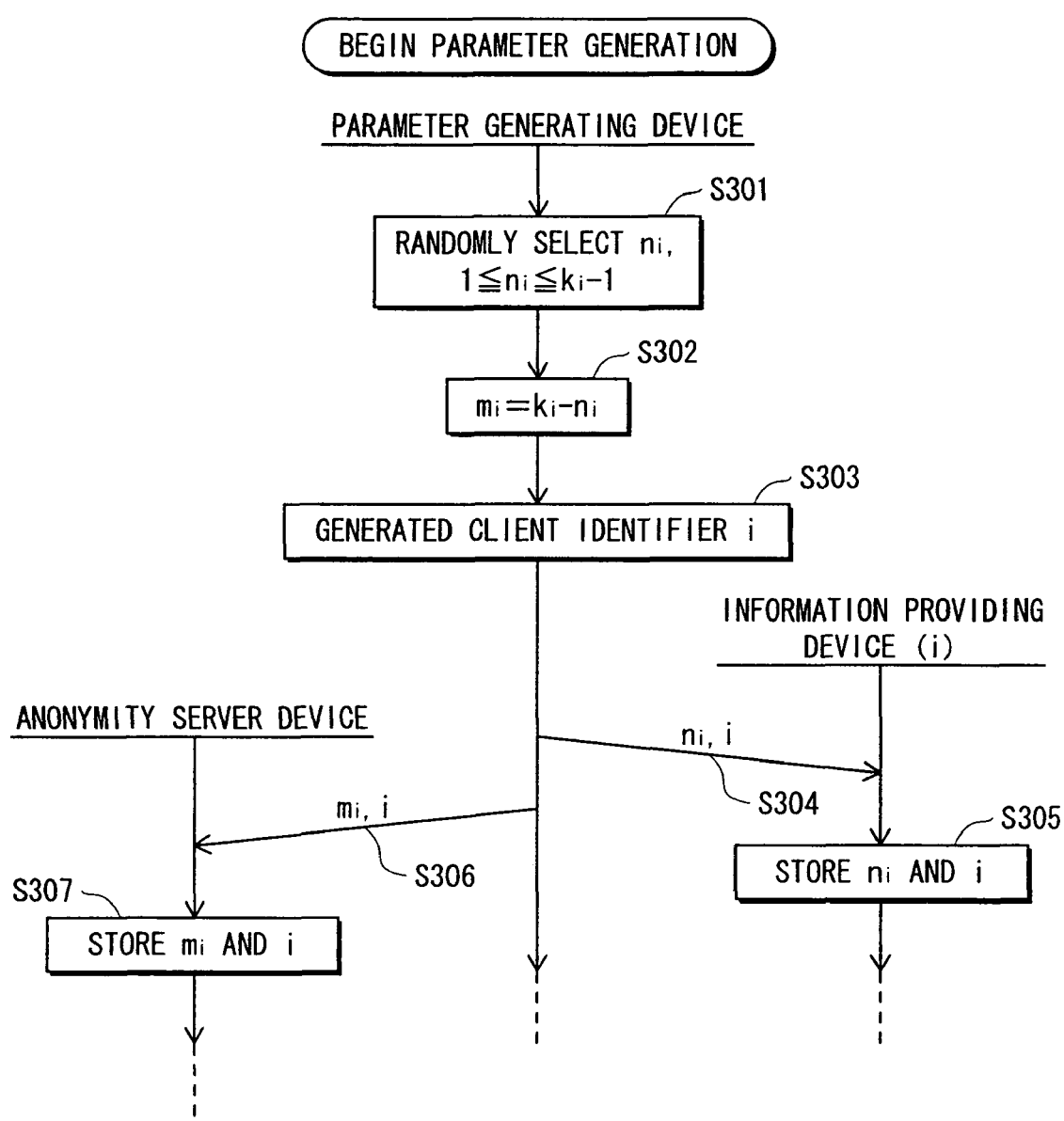
FIG. 23 is a flow-chart showing the operations of a parameter generating device $10c$ of an anonymous information system $1c$, which is one of the modified examples.
Figure 24:
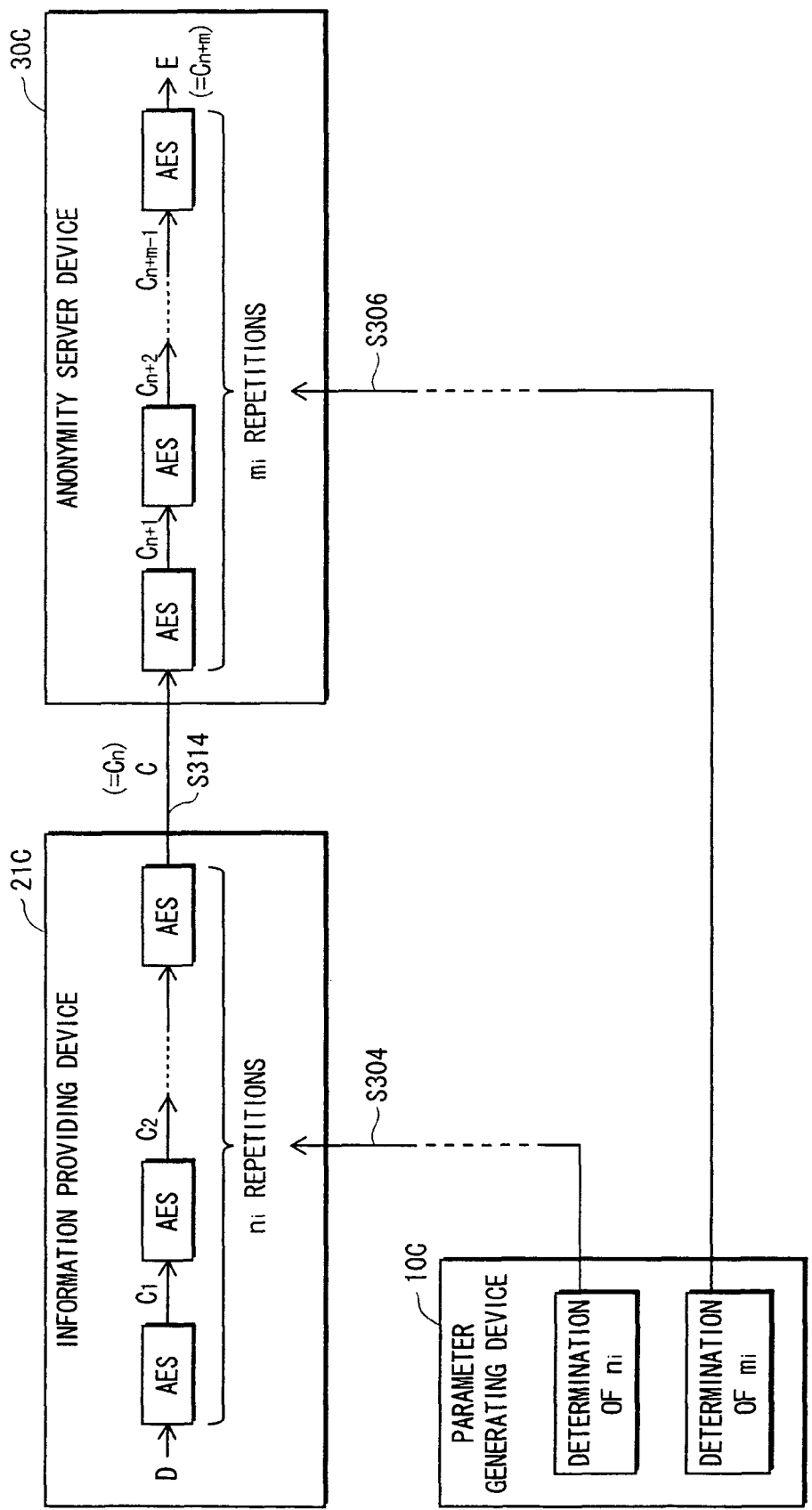
FIG. 24 is a process chart showing the operations of the parameter generating device $10c$ of the anonymous information system $1c$, which is one of the modified examples.

The operations of the parameter generating device 10c are described with reference to the flowchart in FIG. 23 and FIG. 24.

The parameter generating unit 103c randomly selects the first number of repetitions $n_i$ such that $1 \leq n_i \leq k_i-1$ (Step S301), calculates the second number of repetition $m_i=k_i-n_i$ (Step S302), generates a client identifier that uniquely identifies said information providing device (Step S303). The parameter generating unit 103c then transmits the first number of repetitions $n_i$ and the client identifier i to the information providing device (Step S304), and transmits the second number of repetitions $m_i$ and the client identifier to the anonymity server 30c (Step S306).

The characteristic parameter storing unit 204c of the information providing device stores the first number of repetitions $n_i$, and the identifier storing unit 206c stores the client identifier i (Step S305).

Further, the parameter list storing unit 312c of the anonymity server device 30 stores the second number of repetitions $m_i$ and the client identifier i in correspondence with each other (Step S307).

(2) Operations of Information Providing Device 21c and Anonymity Server Device 30.

The operations of the information providing device 21c and the anonymity server device 30 are described with reference to the process chart of FIG. 24.

The first converting unit 205 of the information providing device performs the encryption algorithm AES on the encoded personal information received from the encoder unit 202c, using the designated key KEY$_1$, to generate the first encrypted individual information $C_1$ (Step S311).

Next, the first converting unit 205c performs the encryption algorithm AES on the generated first encrypted individual information $C_1$, using a designated key KEY$_2$, to generate the second encrypted individual information $C_2$ (Step S312).

In the same way, the first converting unit 205 repeats the encryption algorithm AES the number of times indicated by the first number of repetitions $n_i$ to generate the $n^{th}$ encrypted individual information $C_n$, which is the semi-anonymous individual identifier C (Step S313).

The generated semi-anonymous individual identifier C undergoes a change in form and is then transmitted from the information providing device 21c to the anonymity server device 30 (Step S314).

The second converting unit 314c of the anonymity server performs the encryption algorithm AES on the semi-anonymous identifier C, using the designated encryption key KEY$_{n+1}$, to generate the $(n+1)^{th}$ encrypted individual information $C_{n+1}$ (Step S315).

Next, the second converting unit 314c performs encryption algorithm AES on the generated $(n+1)^{th}$ encrypted individual information $C_{n+1}$, using the designated encryption key KEY$_{n+2}$, to generate the $(n+2)^{th}$ encrypted individual information $C_{n+2}$ (Step S316).

Then, in the same way, the second converting unit 314c repeats the encryption algorithm the number of times indicated by the second number of repetitions $m_i$ to generate the $(n+m)^{th}$ encrypted individual information $C_{n+m}$ (Step S317). The $(n+m)^{th}$ encrypted individual information generated in this way is the semi-anonymous individual identifier E.

4.5 Supplementary Description

The semi-anonymous individual identifier C calculated by the information providing device 21c is generated by performing the encryption algorithm AES on the encoded personal information D the number of times indicated by the first number of repetitions $n_i$. Further, the anonymous individual identifier E is generated by performing the encryption algorithm AES on the semi-anonymous individual identifier C the number of times indicated by the second number of repetitions $m_i$. Since $n_i+m_i=k_i$, the result of these operations is always the result generated by performing the encryption algorithm AES on the encoded personal information D the number of times indicated by the total number of repetitions $k_i$.

5. Summary

As described above, the present invention relates to a system for providing information of highly private nature, such as medical information including results from consultations and examinations, grades from various types of test, personal assessments, survey responses, and the like, for purposes such as statistical analysis and academic research, while keeping this information in an anonymous format so that it is impossible to specify to whom the information relates.

The present invention is an anonymous information providing system for providing information containing individual information, the information being provided as anonymous information with the individual information concealed, the anonymous information providing system including: an information registration device having a first anonymity processing unit for performing first conversion processing on the individual information included in the information to generate first anonymous individual information, and a first anonymous information transmitting unit for transmitting the first anonymous information containing the first anonymous individual information; an information storing device having a second anonymity processing unit for performing second conversion processing on the first anonymous individual information included in the first anonymous information to generate second anonymous individual information, and a storing unit for storing, in a searchable or perusable state, the second anonymous information that includes the second anonymous individual information; and a searching device for transmitting, to the information storing device, a request to peruse, or search for, the second anonymous information being stored in the storing unit, and for receiving anonymous information corresponding to the request.

Here, the anonymous information providing system may include at least two information registration devices, and in each information registration device, the first conversion processing in the first anonymous processing unit may be different from the first conversion processing in the one or more other information registration devices.

Here, the anonymous information providing system may include at least two information registration devices, and in the second anonymity processing unit in the storing device, the second conversion processing information may differ according to the information registering device that is the transmission source of the first anonymous information.

Further, the present invention is an information registration device in an anonymous information providing system for providing information containing individual information as anonymous information with the individual information concealed, the information registration device including: a first anonymity processing unit for performing first conversion processing on the individual information contained in the information to generate first anonymous individual information; and a first anonymous information transmitting unit for transmitting first anonymous information containing the first anonymous individual information.

Here, the first anonymity processing unit may include: a first parameter storing unit for storing a first parameter; and a first conversion processing unit for performing the first conversion processing on the individual information based on the first parameter.

Here, the first parameter may be different for each information registration device.

Here, the information registration device may further include a first parameter update unit for updating the first parameter stored in the first parameter storing unit.

Further, the present invention is an information storing device in an anonymous information providing system that provides information containing individual information as anonymous information with the individual information concealed, the information storing device including: a second anonymity processing unit for performing second conversion processing on first anonymous individual information contained in received first anonymous information to generate second anonymous individual information, and a storing unit for storing second anonymous information that includes the second anonymous individual information in a searchable or perusable state.

Here, the second anonymity processing unit may include: a second parameter storing unit for storing a second parameter; and a second conversion processing unit for performing second conversion processing on the first anonymous individual information based on the second parameter.

Here, the second parameter storing unit may store at least two second parameters, the second conversion processing unit may include a second parameter selecting unit for selecting, depending on an information registration device that transmitted the first anonymous individual information, one of the at least two second parameters stored in the second conversion processing unit, and the second conversion processing unit may perform the second conversion processing on the first anonymous individual information based on the second parameter selected by the second parameter selecting unit.

Here, the information storing device may further include a second parameter updating unit for selecting and updating one of the two or more second parameters stored in the second parameter storing unit.

As described above, according to this construction of the present invention, the process for converting secret information to anonymous information can be divided up and performed in parts by the information registration device and the information storing device respectively.

In this way, by splitting the conversion process for converting from the individual information to the anonymous ID between the side for providing information for the database and the side managing the database, the anonymous information providing system of the present invention has the effect of maintaining the anonymity of the database, even if the conversion processing on one side is hacked.

6. Other Modifications

The present invention has been described based on the above embodiment but is not of course limited to the above embodiment. The following types of case are further included in the present invention.

(1) When a new information providing device is added to the anonymous information system 1, as explained above, the parameter generating device 10 generates a client identifier and first and second characteristic parameters for use by said information providing device, and transmits this information to said information providing device and to the anonymity server 30 as appropriate. In this case, the information providing device stores the client identifier and the first characteristic parameter, and the anonymity server device 30 stores the client identifier and the second characteristic parameter.

(2) Though, in the above embodiment, the input unit 201 of the information providing device 21 receives the input of the individual specifying information S and the individual related information R from the operator of the information providing device 21, the present invention is not limited to this method. Instead, the individual specifying information S and/or the individual related information R may be stored in advance on an external storage unit such as a memory card, an IC card, or a hard disk drive, and the individual specifying information S and/or individual related information R read from this external storage unit. Moreover, the individual specifying information S and/or the individual related information R may be stored in advance in internal memory inside the information providing device 21, and the individual specifying information S and/or individual related information R read from this internal memory.

(3) Some other examples of individual specifying information and individual related information are indicated below.

An example of individual specifying information is information that specifies the students of a school. In this case the corresponding individual related information may be information indicating the grades from tests which have taken place at the school.

A further example of individual specifying information is information that specifies the respondents to a survey, in which case the corresponding individual related information may be the content of the respondents' survey responses.

(4) Data being transmitted among the parameter generating device 10, the information providing devices 21, 22, 23, . . ., the anonymity server device 30, and the information searching devices 41, 42, 43, . . ., may be protecting using an encryption method such as an SSL (Secure Socket Layer).

(5) Client terminal devices having the functions of both the information providing device and the information search device may be connected to the network 2.

(6) Specifically, each of the above devices is constructed from a microprocessor, ROM, RAM, a hard disk unit, a display unit, a keyboard, a mouse, and the like. A computer program is stored in the RAM or the hard disk unit. Here, in order to realize a predetermined function, the computer program is constructed from a combination of instruction codes, each of which indicates an instruction to the computer. The microprocessor operates according to the computer program, and each device thereby realizes its predetermined function. In other words, the microprocessor reads the instruction codes included in the computer program one at a time, decodes the read instructions, and operates according to the results of this decoding.

(7) A part or all of the components that make up the above devices may be constructed from a single system LSI (a Large Scale Integrated circuit). System LSI is super-multifunctional LSI, which is produced by integrating a plurality of components into a single chip. Specifically, system LSI is a computer system constructed from a microprocessor, ROM, RAM, and the like. A computer program is stored in the RAM. The system LSI realizes its function by the microprocessor operating according to the computer program.

Further, a part or all of the components that make up the above devices may be distributed across a number of separate chips or included on a single chip. Moreover, though it has been called LSI here, this type construction is variously called IC, system LSI, super LSI, and ultra LSI depending on the level of integration.

Further, the method for forming the integrated circuit is not limited to LSI, and integration may alternatively be achieved using a special purpose circuit or general purpose processor. Further, a FPGA (Field Programmable Gate Array), a reconfigurable processor whose LSI internal circuit cell settings and connections can be reconfigured post-LSI production, or the like may be used.

(8) Further a part or all of the components that make up the above devices may be constructed from removable IC cards or unit modules. These IC cards or modules are computer systems constructed from microprocessors, ROM, RAM, and the like. The IC cards or modules may include super-multifunctional LSI. The IC card or module realizes its function by a microprocessor operating according to a computer program. The IC cards or modules may be tamper-resistant.

(9) The present invention may be the methods described above. Further, it may be computer programs for realizing the methods by means of one or more computers, or be the digital signals composing the computer programs.

Further, the present invention may be content recorded on a recording medium, such as a flexible disk, a hard disk, CD-ROM, MO, DVD, DVD-ROM, DVD-RAM, BD (Blu-ray Disk), a semiconductor memory, or the like, from which a computer can read the computer programs or the digital signals. Further, the present invention may be the computer program or digital signals recorded on any of these recording media.

Further, the present invention may be the computer programs or digital signals transmitted by means of an electronic communications circuit, a wired or wireless communications circuit, a network such as the internet, a data broadcast, or the like.

Further, the present invention may be a computer system that includes a microprocessor and memory, the memory storing the computer program and the microprocessor operating according to the computer program.

Further, the present invention may be implemented in another independent computer system by recording the programs or the digital signals on a recording medium and conveying the recording medium between systems, or by transmitting the programs, or the digital signals, by way of a network, or the like.

(10) The present invention may be any combination of the embodiment and the modifications.

(11) As described above, the anonymous information system of the present invention not only realizes the high-performance search function of searching for information belonging to the same person while protecting the anonymity of the provided information, but also solves the problem of the prior art, which is the exposure of secret information by a specified institution resulting in a loss in anonymity of the provided information. Moreover, even in the worst case scenario in which part of the secret information has been exposed, the anonymous information system of the present invention has the advantage of providing a means for recovering secrecy in the system without a great deal of trouble. Consequently, the anonymous information system of the current invention is of use in database systems that demand a high level of anonymity.

INDUSTRIAL APPLICABILITY

The devices which compose the present invention can be applied continuously, or intermittently and repeatedly, in any industry that deals with anonymous information. Further, the devices which compose the present invention can be made and sold continuously, or intermittently and repeatedly, by the electronic industry.

Although the present invention has been fully described by way of examples with reference to the accompanying drawings, it is to be noted that various changes and modifications will be apparent to those skilled in the art. Therefore, unless otherwise such changes and modifications depart from the scope of the present invention they should be construed as being included therein.

What is claimed is:

1. An anonymous information system that performs anonymity conversion processing on original individual specifying information D that specifies an individual, to generate anonymous individual specifying information E, the anonymous information system comprising:

a conversion splitting device configured to generate a first parameter KA and a second parameter KB based on a base parameter, the anonymity conversion processing being split into two portions to generate first conversion processing that is one of the two portions and second conversion processing that is the other one of the two portions, the first parameter KA being utilized for the first conversion processing and the second parameter KB being utilized for the second conversion processing;

a first converting device configured to receive from said conversion splitting device the first parameter KA, to perform the first conversion processing on the original individual specifying information using a parameter P and the received first parameter KA according to a first expression, and to generate semi-anonymous individual specifying information, the first expression being represented as, $C = (KA)^D \bmod P$; and a second converting device configured to receive from said conversion splitting device the second parameter KB, to receive from said first converting device the generated semi-anonymous individual specifying information C and to perform the second conversion processing on the received semi-anonymous individual specifying information C using the parameter P and the received second parameter KB according to a second expression, and to generate the anonymous individual specifying information E from the generated semi-anonymous individual specifying information C, the second expression being represented as, $E = (C)^{KB} \bmod P$.

wherein said first converting device comprises an information providing device that provides the original individual specifying information D, and provides individual related information relating to the individual, said second converting device comprises an information storing device that stores the anonymous individual specifying information E, and stores the anonymous individual specifying information E in correspondence with the individual related information, and the conversion splitting device generates a random number $X_i$ as a base parameter, wherein the first parameter $KA=G^{X_{inv}}$ mod q, and the second parameter $KB=X_i$, where $X_i \times = X_{inv}$ mod q, and q and G are constants.

2. The anonymous information system of claim 1, wherein the anonymity conversion processing generates, from the original individual specifying information D, the anonymous individual specifying information E from which the individual cannot be specified, said conversion splitting device comprises:

a first parameter generating unit configured to randomly generate the first parameter KA based on the base parameter;

a second parameter generating unit configured to generate, based on the base parameter, the second parameter KB that is complementary to the first parameter KA with respect to the base parameter; and a first transmission unit configured to transmit the first parameter KA to said first converting device, and to transmit the second parameter KB to said second converting device, said first converting device comprises:

a first receiving unit configured to receive the first parameter KA;

an inputting unit configured to input the original individual specifying information D into said first converting device;

a first converting unit configured to perform, as the first conversion processing, a repetitive calculation using the received first parameter KA and the input original individual specifying information, to generate the semi-anonymous individual specifying information C;

a second transmission unit configured to transmit the generated semi-anonymous individual specifying information C to said second converting unit, and said second converting device comprises:

a storing unit having a region for storing the anonymous individual specifying information E;

a second receiving unit configured to receive the second parameter KB from said conversion splitting device and to receive the semi-anonymous individual specifying information C from said first converting device; and a second converting unit configured to perform, as the second conversion processing, a repetitive calculation using the received second parameter KB and the received semi-anonymous individual specifying information C to generate the anonymous individual specifying information E information, and to store the generated anonymous individual specifying information E into said storing unit.

3. The anonymous information system of claim 2, further comprising:

an information searching device configured to acquire, from said second converting device, the anonymous individual specifying information E and the individual related information which are desired by an operator of said information searching device.

4. The anonymous information system of claim 2, wherein said conversion splitting device further generates a third parameter and a fifth parameter based on the base parameter, the anonymity conversion processing being split into two portions to generate third conversion processing and fourth conversion processing, the third conversion processing being one of the two portions and different from the first conversion processing, and the fourth conversion processing being the other one of the two portions and different from the second conversion processing, the third parameter being utilized for the third conversion processing and the fourth parameter being utilized for the fourth conversion processing, said anonymous information system further comprises:

a third converting device configured to receive from said conversion splitting device the third parameter and to perform the third conversion processing on the original individual specifying information D using the third parameter to generate other semi-anonymous individual specifying information from the original individual specifying information; and said second converting device further receives from the conversion splitting device the fourth parameter, receives from said third converting device the generated other semi-anonymous individual specifying information and performs the fourth conversion processing on the received other semi-anonymous individual specifying information using the fourth parameter to generate the anonymous individual specifying information from the received other semi-anonymous individual specifying information.

5. The anonymous information system of claim 4, wherein the third parameter is distinct from the first parameter KA, and the fourth parameter differing from the second parameter KB.

6. The anonymous information system of claim 2, wherein said conversion splitting device further generates a third parameter and a fourth parameter based on the base parameter, other anonymity conversion processing being split into two portions to generate third conversion processing and fourth conversion processing, the other anonymity conversion processing being distinct from the anonymity conversion processing, the third conversion processing being one of the portions and different from the first conversion processing and, fourth conversion processing being the other of the portions and different from the second conversion processing, the third parameter being utilized for the third conversion processing and the fourth parameter being utilized for the fourth conversion processing, instead of the first conversion processing, said first conversion device receives from said conversion splitting device the third parameter and performs the third conversion processing on the original individual specifying information using the third parameter to generate other semi-anonymous individual specifying information from the original individual specifying information D, and instead of the second conversion processing, said second conversion device receives from said conversion splitting device the fourth parameter, receives from said first conversion device the generated other semi-anonymous individual specifying information and performs the fourth conversion processing on the generated other semi-anonymous individual specifying information using the fourth parameter to generate other anonymous individual specifying information from the received other semi-anonymous individual specifying information.

7. The anonymous information system of claim 6, wherein
said first parameter generating unit randomly generates based on the base parameter the third parameter that is different to the first parameter KA;
said second parameter generating unit generates, based on the base parameter, the fourth parameter that is complementary to the third parameter with respect to the base parameter;
said first transmission unit further transmits the third parameter to said first converting device, and transmits the fourth parameter to said second converting device;
said first receiving unit further receives the third parameter from said first parameter generating unit;
said first converting unit performs, as the third conversion processing, a repetitive calculation using the received third parameter and the input original individual specifying information D to generate other semi-anonymous individual specifying information;
said second transmission unit transmits the generated other semi-anonymous individual specifying information to said second converting unit;
said storing unit has a region for storing other anonymous individual specifying information;
said second receiving unit receives the fourth parameter from said first transmission unit and receives from said second transmission unit the other semi-anonymous individual specifying information; and
said second converting unit performs, as the fourth conversion processing, a repetitive calculation using the received fourth parameter and the received other semi-anonymous individual specifying information to generate the other anonymous individual specifying information, and stores the generated other anonymous individual specifying information into said storing unit.

8. The anonymous information system of claim 2, wherein
said conversion splitting device further generates a third parameter and a fourth parameter based on the base parameter, other anonymity conversion processing being split into two portions to generate third conversion processing and fourth conversion processing, the other anonymity conversion processing being distinct from the anonymity conversion processing, the third conversion processing being one of the portions and different from the first conversion processing and, fourth conversion processing being the other of the portions and different from the second conversion processing, the third parameter being utilized for the third conversion processing and the fourth parameter being utilized for the fourth conversion processing,
instead of performing the first conversion processing, said first conversion device performs the anonymity conversion processing on the original individual specifying information D to generate the anonymous individual specifying information, receives from said conversion splitting device the third parameter and performs the third conversion processing on the generated anonymous individual specifying information using the third parameter to generate other semi-anonymous individual specifying information from the anonymous individual specifying information, and
instead of performing the second conversion processing, said second conversion device receives from said conversion splitting device the third parameter, receives from said first conversion device the generated other semi-anonymous individual specifying information, and performs the fourth conversion processing on the generated other semi-anonymous individual specifying information using the fourth parameter to generate other anonymous individual specifying information from the received other semi-anonymous individual specifying information.

9. The anonymous information system of claim 8, wherein
said first parameter generating unit randomly generates based on the base parameter the third parameter that is different from the first parameter KA;
said second parameter generating unit generates, based on the base parameter, the fourth parameter that is complementary to the third parameter with respect to the base parameter;
said first transmission unit further transmits the third parameter to said first converting device, and transmits the fourth parameter to said second converting device;
said first receiving unit further receives the third parameter from said first parameter generating unit;
said first converting unit performs the anonymity conversion processing on the original individual specifying information D to generate the anonymous individual specifying information, and as the third conversion processing, performs a repetitive calculation using the received third parameter and the generated anonymous individual specifying information to generate the other semi-anonymous individual specifying information;
said second transmission unit transmits the generated other semi-anonymous individual specifying information to said second converting unit;
said storing unit has a region for storing other anonymous individual specifying information;
said second receiving unit receives the fourth parameter from said first transmission unit and receives from the second transmission unit the other semi-anonymous individual specifying information; and
said second converting unit performs, as the fourth conversion processing, a repetitive calculation using the received fourth parameter and the received other semi-anonymous individual specifying information to generate the other anonymous individual specifying information, and stores the generated other anonymous individual specifying information into said storing unit.

10. A parameter generating device in an anonymous information system that includes an information providing device and an information storing device, and that performs anonymity conversion processing on original individual information D specifying an individual, to generate anonymous individual specifying information E, the anonymity conversion processing generating, from the original individual specifying information D and based on a base parameter, the anonymous individual specifying information E from which the individual cannot be specified, the anonymity conversion processing being split into two portions to generate first conversion processing that is one of the two portions and second conversion processing that is the other one of the two portions, first parameter KA being utilized for the first conversion processing and second parameter KB being utilized for the second conversion processing, the parameter generating device comprising:
a first parameter generating unit configured to randomly generate the first parameter KA based on the base parameter;
a second parameter generating unit configured to generate, based on the base parameter, the second parameter KB that is complementary to the first parameter KA with respect to the base parameter; and a first transmission unit configured to transmit the first parameter KA to the information providing device, and transmit the second parameter KB to the information storing device, wherein the information providing device receives the first parameter KA from said first transmission unit, inputs the original individual specifying information D into a first converting device, performs, as the first conversion processing according to a first expression, a repetitive calculation using a parameter P and the received first parameter KA and the input original individual specifying information D, to generate the semi-anonymous individual specifying information C, and transmits the generated semi-anonymous individual specifying information C to a second converting unit, the first expression being represented as, $C=(KA)^{\wedge}D \bmod P,$ wherein said information storing device receives the second parameter KB from said first transmission unit, receives the semi-anonymous individual specifying information C from the information providing device, performs, as the second conversion processing according to a first expression, a repetitive calculation using the parameter P and the received second parameter KB and the received semi-anonymous individual specifying information C to generate the anonymous individual specifying information E, and stores the generated anonymous individual specifying information E into the information storing device, the second expression being represented as, $E=(C)^{\wedge}KB \bmod P,$ wherein the first converting device comprises the information providing device that provides the original individual specifying information D, and provides individual related information relating to the individual, the second converting device comprises the information storing device that stores the anonymous individual specifying information E, and stores the anonymous individual specifying information E in correspondence with the individual related information, and a conversion splitting device generates a random number $X_i$ as a base parameter, wherein the first parameter $KA=G^{\wedge}X_{inv} \bmod q$, and the second parameter $KB=X_i$, where $X_i \times X_{inv}=1 \bmod q$, and q and G are constants.

11. The parameter generating device of claim 10, wherein said first parameter generating unit and said second parameter generating unit are constructed from one or more large scale integrated circuits.

12. An information providing device in an anonymous information system that includes a parameter generating device and an information storing device, and that performs anonymity conversion processing on original individual information specifying an individual D, to generate anonymous individual specifying information E, the anonymity conversion processing generating, from the original individual specifying information D and based on a base parameter, the anonymous individual specifying information E from which the individual cannot be specified, the anonymity conversion processing being split into two portions to generate first conversion processing that is one of the two portions and second conversion processing that is the other one of the two portions, a first parameter KA being utilized for the first conversion processing and a second parameter KB being utilized for the second conversion processing, the parameter generating device randomly generating the first parameter KA based on the base parameter, generating, based on the base parameter, the second parameter KB that is complementary to the first parameter KA with respect to the base parameter, transmitting the first parameter KA to the information providing device, and transmitting the second parameter KB to the information storing device, the information providing device comprising:

a first receiving unit configured to receive the first parameter KA from the parameter generating device, an inputting unit configured to input the original individual specifying information D into the information providing device;

a first converting unit configured to perform, as the first conversion processing according to a first expression, a repetitive calculation using a parameter P and the received first parameter KA and the input original individual specifying information D to generate the semi-anonymous individual specifying information C, the first expression being represented as, $C=(KA)^{\wedge}D \bmod P$; and a second transmission unit configured to transmit the generated semi-anonymous individual specifying information C to the information storing device, wherein the information storing device receives the second parameter KB from a first transmission unit, receives the semi-anonymous individual specifying information C from the information providing device, performs, as the second conversion processing according to a second expression, a repetitive calculation using the parameter P and the received second parameter KB and the received semi-anonymous individual specifying information C to generate the anonymous individual specifying information E, and stores the generated anonymous individual specifying information E into the information storing device, the second expression being represented as, $E=(C)^{\wedge}KB \bmod P,$ wherein said first converting unit comprises the information providing device that provides the original individual specifying information D, and provides individual related information relating to the individual, a second converting unit comprises the information storing device that stores the anonymous individual specifying information E, and stores the anonymous individual specifying information E in correspondence with the individual related information, and a conversion splitting device generates a random number $X_i$ as a base parameter, wherein the first parameter $KA=G^{\wedge}X_{inv} \bmod q$, and the second parameter $KB=X_i$, where $X_i \times X_{inv}=1 \bmod q$, and q and G are constants.

13. The information providing device of claim 12, wherein said first converting unit is constructed from one or more large scale integrated circuits.

14. An information storing device of an anonymous information system that further includes a parameter generating device and an information providing device, and that performs anonymity conversion processing on original individual information D specifying an individual, to generate anonymous individual specifying information E, the anonymity conversion processing generating, from the original individual specifying information D and based on a base parameter, the anonymous individual specifying information E from which the individual cannot be specified, the anonymity conversion processing being split into two portions to generate first conversion processing that is one of the two portions and second conversion processing that is the other one of the two portions, first parameter KA being utilized for the first conversion processing and second parameter KB being utilized for the second conversion processing, the parameter generating device randomly generating the first parameter KA based on the base parameter, generating, based on the base parameter, the second parameter KB that is complementary to the first parameter KA with respect to the base parameter, transmitting the first parameter KA to the information providing device, transmitting the second parameter KB to the information storing device, the information providing device receiving the first parameter KA, inputting the original individual specifying information D into the information providing device, performing, as the first conversion processing according to a first expression, a repetitive calculation using a parameter P, the received first parameter KA and the input original individual specifying information D to generate the semi-anonymous individual specifying information C, and transmitting the generated semi-anonymous individual C specifying information to the information storing device, the first expression being represented as, $C=(KA)\hat{}D \bmod P$, the information storing device comprising:
a storing unit having a region for storing the anonymous individual specifying information E;
a second receiving unit configured to receive the parameter P and the second parameter KB from the parameter generating device and to receive the semi-anonymous individual specifying information C from the information providing device; and
a second converting unit configured to perform, as the second conversion processing according to a second expression, a repetitive calculation using the parameter P, the received second parameter KB and the received semi-anonymous individual specifying information C to generate the anonymous individual specifying information E, and to store the generated anonymous individual specifying information E into the storing unit, the second expression being represented as, $E=(C)\hat{}KB \bmod P$ wherein a first converting device comprises the information providing device that provides the original individual specifying information D, and provides individual related information relating to the individual,
said second converting unit comprises the information storing device that stores the anonymous individual specifying information E, and stores the anonymous individual specifying information E in correspondence with the individual related information, and
a conversion splitting device generates a random number Xi as a base parameter, wherein the first parameter $KA=G\hat{}X_{inv}$ mod q, and the second parameter $KB=X_i$, where
$X_i \times X_{inv}=1$ mod q, and q and G are constants.

15. The information storing device of claim 14, wherein said second converting unit is constructed from one or more large scale integrated circuits.

16. A method used by an anonymous information system that performs anonymity conversion processing on original individual specifying information D that specifies an individual, to generate anonymous individual specifying information E, the method comprising:
generating, via a conversion splitting device, a first parameter KA and a second parameter KB based on a base parameter, the anonymity conversion processing being split into two portions to generate first conversion processing that is one of the two portions and second conversion processing that is the other one of the two portions, the first parameter KA being utilized for the first conversion processing and the second parameter KB being utilized for the second conversion processing;
receiving, via a first converting device, the generated first parameter KA;
performing the first conversion processing on the original individual specifying information D using a parameter P and the received first parameter KA according to a first expression, the first expression being represented as, $C=(KA)\hat{}D \bmod P$;

generating semi-anonymous individual specifying information C from the original individual specifying information D;
receiving, via a second converting device, the generated second parameter KB;
receiving the generated semi-anonymous individual specifying information C; and
performing the second conversion processing on the received semi-anonymous individual specifying information C using the parameter P and the received second parameter KB according to a second expression; and
generating the anonymous individual specifying information E from the generated semi-anonymous individual specifying information C, the second expression being represented as, $E=(C)\hat{}KB \bmod P$, wherein said first conversion provides the original individual specifying information D, and provides individual related information relating to the individual,
a second conversion stores the anonymous individual specifying information E, and stores the anonymous individual specifying information E in correspondence with the individual related information, and
generating a random number Xi as a base parameter, wherein the first parameter $KA=G\hat{}X_{inv}$ mod q, and the second parameter $KB=X_i$, where
$X_i \times X_{inv}=1$ mod q, and q and G are constants.

17. A computer-readable recording medium storing a program used by an anonymous information system that performs anonymity conversion processing on original individual specifying information D that specifies an individual, to generate anonymous individual specifying information E, the program comprising:
generating a first parameter KA and a second parameter KB based on a base parameter, the anonymity conversion processing being split into two portions to generate first conversion processing that is one of the two portions and second conversion processing that is the other one of the two portions, the first parameter KA being utilized for the first conversion processing and the second parameter KB being utilized for the second conversion processing;
receiving the generated first parameter KA;
performing the first conversion processing on the original individual specifying information D using a parameter P and the received first parameter KA according to a first expression, the first expression being represented as, $C=(KA)^D \bmod P;$ generating semi-anonymous individual specifying information C from the original individual specifying information D;
receiving the generated second parameter KB;
receiving the generated semi-anonymous individual specifying information C; and
performing the second conversion processing on the received semi-anonymous individual specifying information C using the parameter P and the received second parameter KB according to a second expression; and
generating the anonymous individual specifying information E from the generated semi-anonymous individual specifying information C, the second expression being represented as, $E=(C)^{KB} \bmod P,$ wherein said first conversion provides the original individual specifying information D, and provides individual related information relating to the individual, a second conversion stores the anonymous individual specifying information E, and stores the anonymous individual specifying information E in correspondence with the individual related information, and generating a random number Xi as a base parameter, wherein the first parameter $KA=G^{X_{inv}} \bmod q$, and the second parameter $KB=X_i$, where $X_i \times X_{inv}=1 \bmod q$, and q and G are constants.

* * * * *

UNITED STATES PATENT AND TRADEMARK OFFICE
CERTIFICATE OF CORRECTION

PATENT NO. : 7,747,491 B2  Page 1 of 1
APPLICATION NO. : 11/281577
DATED : June 29, 2010
INVENTOR(S) : Kaoru Yokota et al.

It is certified that error appears in the above-identified patent and that said Letters Patent is hereby corrected as shown below:

In column 49, claim 1, line 13, "$X_i x = X_{inv}$ mod q" should read --$X_i x \ X_{inv} = 1$ mod q--.

Signed and Sealed this

Second Day of November, 2010

David J. Kappos
*Director of the United States Patent and Trademark Office*